(12) United States Patent
Arculus-Meanwell et al.

(10) Patent No.: US 11,633,419 B2
(45) Date of Patent: Apr. 25, 2023

(54) METHODS OF TREATING, REDUCING THE INCIDENCE OF, AND/OR PREVENTING ISCHEMIC EVENTS

(71) Applicant: Chiesi Farmaceutici S.p.A., Parma (IT)

(72) Inventors: Clive Arthur Arculus-Meanwell, Bernardsville, NJ (US); Simona Skerjanec, Basel (CH); Jayne Prats, Carlisle, MA (US)

(73) Assignee: CHIESI FARMACEUTICI S.P.A., Parma (IT)

( * ) Notice: Subject to any disclaimer, the term of this patent is extended or adjusted under 35 U.S.C. 154(b) by 0 days.

(21) Appl. No.: 16/452,770

(22) Filed: Jun. 26, 2019

(65) Prior Publication Data

US 2019/0321386 A1    Oct. 24, 2019

Related U.S. Application Data

(63) Continuation of application No. 14/050,266, filed on Oct. 9, 2013, now Pat. No. 10,376,532, which is a continuation-in-part of application No. 13/792,056, filed on Mar. 9, 2013, now Pat. No. 9,427,448, which is a continuation-in-part of application No. 12/943,717, filed on Nov. 10, 2010, now Pat. No. 9,925,265, said application No. 16/452,770 is a continuation of application No. 14/050,266, filed on Oct. 9, 2013, now Pat. No. 10,376,532, which is a continuation-in-part of application No. 12/943,717, filed on Nov. 10, 2010, now Pat. No. 9,925,265.

(60) Provisional application No. 61/260,361, filed on Nov. 11, 2009.

(51) Int. Cl.
| | |
|---|---|
| *A61K 9/00* | (2006.01) |
| *A61K 31/7076* | (2006.01) |
| *A61K 38/10* | (2006.01) |
| *A61K 31/4365* | (2006.01) |
| *A61K 45/06* | (2006.01) |
| *A61K 47/02* | (2006.01) |
| *A61K 47/26* | (2006.01) |
| *A61K 9/19* | (2006.01) |

(52) U.S. Cl.
CPC ........ *A61K 31/7076* (2013.01); *A61K 9/0019* (2013.01); *A61K 9/19* (2013.01); *A61K 31/4365* (2013.01); *A61K 38/10* (2013.01); *A61K 45/06* (2013.01); *A61K 47/02* (2013.01); *A61K 47/26* (2013.01)

(58) Field of Classification Search
CPC ................ A61K 38/10; A61K 31/7076; A61K 31/4365; A61K 47/26
See application file for complete search history.

(56) References Cited

U.S. PATENT DOCUMENTS

| | | | |
|---|---|---|---|
| 4,529,596 | A | 7/1985 | Aubert et al. |
| 5,196,404 | A | 3/1993 | Maraganore et al. |
| 5,288,726 | A | 2/1994 | Koike et al. |
| 5,721,219 | A | 2/1998 | Ingall et al. |
| 5,955,447 | A | 9/1999 | Ingall |
| 6,114,313 | A | 9/2000 | Bland et al. |
| 6,130,208 | A | 10/2000 | Broadhead |
| 6,693,115 | B2 | 2/2004 | Asai et al. |
| 6,861,424 | B2 | 3/2005 | Bryant |
| 7,026,323 | B2 | 4/2006 | Bryant et al. |
| 8,680,052 | B1 | 3/2014 | Arculus-Meanwell et al. |
| 8,716,261 | B2 | 5/2014 | Ruderman Chen et al. |
| 8,759,316 | B2 | 6/2014 | Ruderman Chen |
| 8,871,736 | B2 | 10/2014 | Chen et al. |
| 9,427,448 | B2 | 8/2016 | Arculus-Meanwell |

(Continued)

FOREIGN PATENT DOCUMENTS

| | | |
|---|---|---|
| EP | 2105137 A1 | 9/2009 |
| WO | 199418216 A1 | 2/1994 |

(Continued)

OTHER PUBLICATIONS

Greenbaum et al. "Initial experience with an intravenous P2Y12 platelet receptor antagonist in patients undergoing percutaneous coronary intervention: Results from a 2-part, phase II, multicenter, randomized, placebo- and active-controlled trial", America Heart Journal, 2006, pp. 689.e1-689e.10 (Year: 2006).*

Lincoff et al. "Bivalirudin with planned or provisional abciximab versus low-dose heparin and abciximab during percutaneous coronary revascularization: Results of the Comparison of Abciximab Complications with Hirulog for Ischemic Events Trial (CACHET)", American Heart Journal, 2002, pp. 847-853 (Year: 2002).*

Akers et al. "Pharmacokinetics and Pharmacodynamics of a Bolus and Infusion of Cangrelor: A Direct, Parenteral P2Y12 Receptor Antagonist", J Clin Pharmacol 2010; pp. 27-35 (Year: 2010).*

(Continued)

*Primary Examiner* — Lianko G Garyu
(74) *Attorney, Agent, or Firm* — Vorys, Sater, Seymour and Pease LLP; Maryellen Feehery Hank

(57) ABSTRACT

Methods of treating, reducing the incidence of, and/or preventing an ischemic event in a patient undergoing percutaneous coronary intervention (PCI), comprising administering to the patient a pharmaceutical composition comprising cangrelor. The method may further comprise administering an additional therapeutic agent to the patient, the additional therapeutic agent comprising bivalirudin or a $P2Y_{12}$ inhibitor. Pharmaceutical compositions useful for treating, reducing the incidence of, and/or preventing an ischemic event in a patient undergoing PCI. The pharmaceutical compositions comprise cangrelor, and optionally bivalirudin. Methods of preparing a pharmaceutical composition for treating, reducing the incidence of, and/or preventing an ischemic event in a patient undergoing PCI, comprising admixing cangrelor with one or more pharmaceutically acceptable excipients. An ischemic event may include stent thrombosis, myocardial infarction, ischemia-driven revascularization, and mortality.

14 Claims, 18 Drawing Sheets

(56) References Cited

U.S. PATENT DOCUMENTS

| | | | |
|---|---|---|---|
| 9,925,265 B2* | 3/2018 | Arculus-Meanwell | A61K 45/06 |
| 10,376,532 B2* | 8/2019 | Arculus-Meanwell | A61K 31/519 |
| 2002/0123791 A1 | 9/2002 | Harrison | |
| 2006/0121086 A1 | 6/2006 | Boyer et al. | |
| 2006/0270607 A1 | 11/2006 | Dixon et al. | |
| 2007/0082840 A1 | 4/2007 | Porter et al. | |
| 2007/0093423 A1* | 4/2007 | Tovi | A61K 38/58 530/350 |
| 2007/0254324 A1 | 11/2007 | Rechner | |
| 2007/0276460 A1 | 11/2007 | Davis et al. | |
| 2009/0043380 A1 | 2/2009 | Blaha et al. | |
| 2009/0048216 A1 | 2/2009 | Gretter et al. | |
| 2009/0088834 A1 | 4/2009 | Wang | |
| 2009/0156632 A1* | 6/2009 | Brandt | A61P 9/10 514/301 |
| 2009/0247465 A1 | 10/2009 | Baldo et al. | |
| 2009/0304770 A1 | 12/2009 | Lewis et al. | |
| 2010/0041587 A1 | 2/2010 | Porter et al. | |
| 2010/0120718 A1 | 5/2010 | Perzborn | |
| 2010/0292268 A1 | 11/2010 | Mosher et al. | |
| 2011/0112030 A1 | 5/2011 | Arculus-Meanwell et al. | |
| 2011/0178594 A1 | 7/2011 | Kim et al. | |
| 2011/0276123 A1 | 11/2011 | Davies et al. | |
| 2011/0288043 A1 | 11/2011 | Chen et al. | |
| 2012/0009172 A1 | 1/2012 | Gretler et al. | |
| 2012/0141468 A1 | 6/2012 | Chen et al. | |
| 2012/0184504 A1 | 7/2012 | Strony et al. | |
| 2013/0040898 A1 | 2/2013 | Johansson et al. | |
| 2013/0141468 A1 | 6/2013 | Coon | |
| 2013/0190265 A1 | 7/2013 | Arculus-Meanwell et al. | |
| 2013/0303477 A1 | 11/2013 | Ruderman Chen et al. | |
| 2013/0303478 A1 | 11/2013 | Ruderman Chen et al. | |
| 2013/0316968 A1 | 11/2013 | Ruderman Chen et al. | |
| 2013/0324492 A1 | 12/2013 | Ruderman Chen et al. | |
| 2014/0107032 A1 | 4/2014 | Arculus-Meanwell et al. | |
| 2015/0038449 A1 | 2/2015 | Ruderman Chen et al. | |

FOREIGN PATENT DOCUMENTS

| | | | |
|---|---|---|---|
| WO | 200139781 A1 | 6/2001 | |
| WO | 2005097814 A2 | 10/2005 | |
| WO | 2006119507 A2 | 11/2006 | |
| WO | 2007024472 A2 | 3/2007 | |
| WO | 2008052671 A3 | 7/2008 | |
| WO | 2008127682 A2 | 8/2008 | |
| WO | 2009140092 A1 | 11/2009 | |
| WO | 2011060066 A2 | 5/2011 | |
| WO | 2011134478 A2 | 11/2011 | |
| WO | 2013025476 A1 | 2/2013 | |

OTHER PUBLICATIONS

Lehman et al. "Bivalirudin in percutaneous coronary intervention", Vascular Health and Risk Management 2006:2(4) 357-363) (Year: 2006).*

Stone et al. "Bivalirudin in patients with acute coronary syndromes undergoing percutaneous coronary intervention: a subgroup analysis from the Acute Catheterization and Urgent Intervention Triage strategy (ACUITY) trial", The Lancet, 2007, pp. 907-919 (Year: 2007).*

Group. 2022 In Merriam-Webster.com.Retrieved Jul. 15, 2022, from https://www.merriam-webster.com/dictionary/group (Year: 2022).*

Mortality. 2022. In Merriam-Webster.com.Retrieved Jul. 7, 2022, from https://www.merriam-webster.com/dictionary/mortality (Year: 2022).*

Death. 2022 In Merriam-Webster.com.Retrieved Jul. 7, 2022, from https://www.merriam-webster.com/dictionary/death (Year: 2022).*

Ravnefjord A, Delavaux P, Tornvall J, et al., Ongoing treatment with cangrelor, but not ticagrelor, is associated with a significant reduction in the efficacy of clopidogrel in an ex-vivo canine model, J Thromb Haemost, 2009, p. 349, vol. 7(Suppl 2).

Ravnefjord A, Weilitz J, Emanuel Sson Bm, et al., Evaluation of ticagrelor phannacodynamic interactions with reversibly binding or non-reversibly binding P2Y12 antagonists in an ex-vivo canine, Thromb Res, 2012, pp. 622-628, vol. 130.

Sabatine MS, Novel antiplatelet strategies in acute coronary syndromes, Clev Clin J Med, 2009, pp. S8-S15, vol. 76(suppl 1).

Siddique A, Butt M, Shantsila E, et al., New antiplatelet drugs: beyond aspirin and clopidogrel, Int J Clin Pract, 2009, pp. 776-789, vol. 63.

Van Giezen JJ, Humphries RG, Preclinical and clinical studies with selective reversible direct P2Y12 antagonists, Semin Thromb Hemost, 2005, pp. 195-204, vol. 31, No. 2.

Van Giezen JJ, Optimizing platelet inhibition, Eur Heart J, 2008, pp. D23-D29, vol. 10(Suppl D).

Vasiljev KS, Uri A, Laitinen JT, 2-Alkylthio-substituted platelet P2Y12 receptor antagonists reveal phannacological identity between the rat brain Gi-linked ADP receptors and P2Y12, Neurophanncol, 2003, pp. 145-154, vol. 45, No. 1.

Wang K, Zhou X, Zhou Z, et al., Blockade of the platelet P2Y12 receptor by AR-C69931MX sustains coronary artery recanalization and improves the myocardial tissue perfusion in a canine thrombosis model, Arterioscler Thromb Vasc Biol, 2003, pp. 357-362, vol. 23, No. 1.

Wang K, Zhou X, Zhou Z, et al., Sustained coronary artery recanalization with adjunctive infusion of a novel P2T-receptor antagonist AR-C69931 in a canine model, JACC, 2000, pp. 281A-82A, vol. 35(2 Suppl).

Wang K, Zhou X, Zhou Z, et al., Blockade of the ADP P2T receptor sustains coronary artery recanalization and improves the myocardium tissue perfusion in the canine thrombosis model, Circulation, 2001, p. 96, vol. 104 (17 Suppl).

Weaver WD, Becker R, Harrington R, et al., Safety and efficacy of a novel direct P2T receptor antagonist, AR C6991MX, in patients undergoing percutaneous coronary intervention, Eur Heart J, 2000, p. 382, vol. 21 (Suppl).

Weaver WD, Harrington RA, Grines CL, et al., Intravenous AR C69931MX, a novel P2T platelet receptor antagonist, in patients undergoing percutaneous coronary interventions preliminary results from a placebo or active controlled trial, JACC, 2000, pp. 36A-37A, vol. 35 (2SupplA).

Wiviott SD, De Lemos JA, Antiplatelet agents make a comeback in ST-elevation myocardial infarction, Am Heart J, 2007, pp. 603-606, vol. 154.

Wiviott SD, Michelson AD, Berger PB, et al., Therapeutic goals for effective platelet inhibition: a consensus document, Rev Cardiovasc Med, 2006, pp. 214-225, vol. 7.

Firstenberg, M.S., et al., P4-Safety and Efficacy of Cangrelor, An Intravenous, Short-Acting Platelet Inhibitor in Patients Requiring Cardiac Surgery, American Association for Thoracic Surgery, 2012.

Becker, R.C., et al., Management of Platelet-Directed Phannacotherapy in Patients With Atherosclerotic Coronary Artery Disease Undergoing Elective Endoscopic Gastrointestinal Procedures, JACC, 2009, pp. 2261-2276, vol. 54, No. 24.

Bassand, J-P, Unmet needs in antiplatelet therapy, EHJ Supplements, 2008, pp. D3-D11, vol. 10, Supp. D.

Krajewski, S., et al., Short-acting P2Y12 blockade to reduce platelet dysfunction and coagulopathy during experimental extracorporeal circulation and hypothermia, BJA, 2012, pp. 912-921, vol. 108, No. 6.

Xiang, B., et al., The P2Y12 Antagonists, 2Me SAMP and Cangrelor, Inhibit Platelet Activation through P2Y12/Gr-Dependent Mechanism, PLOS One, 2012, pp. 1-10, vol. 7, Issue 12.

Straub, A., et al., Evidence of Platelet Activation at Medically Used Hypothermia and Mechanistic Data Indicating ADP as a Key Mediator and Therapeutic Target, JAHA, 2011, pp. 1607-1016.

Bhatt, D.L., et al., Effect of platelet inhibition with cagrelor during PCI on ischemic events, 2013, N Engl J Med, pp. 1-15. Supplementary Appendix, Champion Phoenix.

Porter, et al. (eds ), a portion of "Coronary Artery Disease," Chapter 210 in The Merck Manual of Diagnosis and Therapy, 19th Edition, Merck & Co., Inc., Rahway, NJ, 2011, title pages and text pp. 2087-2110.

(56) References Cited

OTHER PUBLICATIONS

Beers, et al., (eds.) "Coronary Artery Disease," Chapter 73 in the Merck Manual of Diagnosis and Therapy, 18th Edition, Merck & Co., Inc., Rahway, NJ, Jan. 2006, title pages and text pp. 626-652.
Storey, R.F., et al., Inhibition of Platelet Aggregation by AZD6140, A Reversible Oral P2Y12 Receptor Antagonist, Compared with Clopidogrel in Patients with Acute Coronary Syndromes, JACC, 2007, pp. 1852-1856, vol. 50, No. 19.
Gurbel, P., et al., Oral Dosing of PRT060128, a Novel Direct-Acting, Reversible-P2Y(12) Antagonist Overcomes High Platelet Reactivity in Patients Non-Responsive to Clopidogrel Therapy, Circulation, 2008, p. S972, vol. 118, No. 18.
Lepantalo A., et al., Antiplatelet Effect of Clopidogrel in Patients with Aspirin Therapy Undergoing Percutaneous Coronary Interventions—Limited Inhibition of the P2Y12 Receptor, Thromb. Res., 2009, pp. 193-198, vol. 124, No. 2.
Brilakis et al., Perioperative Management of Patients with Coronary Stents, JACC, 2007, pp. 2145-2150, vol. 49.
Bonello, et al., Consensus and Future Directions on the Definition of High On-Treatment Platelet Reactivity to Adenosine Diphosphate, JACC, 2010, pp. 919-933, vol. 56.
Price, et al., Standard- vs High-Dose Clopidogrel Based on Platelet Function Testing After Percutaneous Coronary Intervention, JAMA, 2011, pp. 1097-1105, vol. 305, No. 11.
Gurbel, et al., Peri-Operative Platelet Function Testing: The Potential for Reducing Ischaemic and Bleeding Risks, Thromb. Haemost., 2011, pp. 248-252, vol. 106.
Accumetric, LLC, VerifyNow User System User Manual, 2009.
Voisin, et al., Are P2Y12 Reaction Unit (PRU) and % Inhibition Index Equivalent for the Expression of P2Y12 Inhibition by the VerifyNow® Assay? Role of Haematocrit and Haemoglobin Levels, Thromb. Haemost, 2011, pp. 227-229, vol. 106.
International Search Report and Written Opinion by the International Searching Authority, dated Jun. 30, 2009, in the PCT Application No. PCT/IJS09/43820.
International Search Report and Written Opinion by the International Searching Authority, dated Jun. 11, 2009, in the PCT Application No. PCT/IJS09/42681.
Extended European Search Report dated Apr. 11, 2012 in the related European Application No. 09747490.2.
Examination Report dated Aug. 21, 2013 in the related European Application No. 09747490.2.
Office Action dated Jun. 4, 2013 in the related Chinese Application No. 200980126678.1.
Office Action dated Jun. 11, 2013 in the related Japanese Application No. 2011-509659.
International Search Report and Written Opinion by the International Searching Authority, dated Jan. 3, 2014, in the PCT Application No. PCT/US2013/048735.
Angiolillo DJ, et al., Randomized Comparison of a High Clopidogrel Maintenance Dose in Patients with Diabetes Mellitus and Coronary Artery Disease, Circulation, 2007, 708-716, 115.
International Search Report and Written Opinion by the International Searching Authority, dated Feb. 10, 2015, in the PCT Application No. PCT/US2014/059972.
International Search Report and Written Opinion by the International Searching Authority, dated Jun. 2, 2014, in the PCT Application No. PCT/US2013/048741.
Barker CM, Price MJ, Antiplatelet therapy in acute coronary syndromes, Cun-Cardiol Rep, 2008, pp. 327-333, vol. 10, No. 4.
Geisler T, Gawaz M, Steinhubl SR, et al., Current strategies in antiplatelet therapy—Does identification of risk and adjustment of therapy contribute to more effective, personalized medicine in cardiovascular disease?, Pharmacol Ther, 2010, pp. 95-107, vol. 127.
Phillips DR, Conley PB, Sinha U, Andre P, Therapeutic approaches in arterial thrombosis,, J Thromb Haemost, 2005, pp. 1577-1589, vol. 3.

Schneider DJ, Sobel BE, Streamlining the design of promising clinical trials: in-vitro testing of antithrombotic regimens and multiple agonists of platelet activation, Coron Artery Dis, 2009, pp. 175-178, vol. 20, No. 2.
Extended European Search Report dated Apr. 8, 2015 in the related European Application No. 12824414.2.
Office Action dated Jun. 30, 2015 in the related European Application No. 09747490.2.
Leonardi S, et al., Pre-treatment with thienopyridines reduces the amount of myonecrosis in acute coronary syndrome patients invasively managed: insights from the CHAMPION trials, Circulation, 2010, p. A14813, vol. 122, No. 21, Suppl. S.
Lincoff et al., "Bivlirudin with planned or provisional abciximab versus low-dose heparin and abciximab during percutaneous coronary revascularization: Results of the Comparison of Abciximab Complications with Hirulog for Ischemic Events Trial (CACHET)", American Heart Journal, 2002, pp. 847-853 (Year 2002).
Akers eg al., "Pharmacokinetics and Pharmacodynamics of a Bolus and Infusion of Cangrelor: A Direct, Parenteral P2Y12 Receptor Antagonist", J. Clin Pharmacol 2010; pp. 27-35 (Year 2010).
Angiolillo et al., "Clinical overview of promising nonthienopyridine antiplatelet agents", American Heart Journal 2008, S23-S28.
Ansel et al., "Pharmaceutical Dosage Forms and Drug Delivery Systems", Lippincott Williams and Wilkins, 1999, pp. 48-53.
Lehman et al., "Bivalirudin in percutaneous coronary intervention", Vascular Health and Rish Management, 2006, pp. 357-363.
Wallentin, "P2Y12 inhibitors: Differences in properties and mechanisms of action and potential consequences for clinical use"; European Heart Journal, 2009, pp. 1964-1977; published ahead of print Jul. 24, 2009.
Greenbaum et al. (American Heart Journal, V151/N3, Mar. 2006, pp. 689 e 1-e 10).
"What are the risks of percutaneous coronary intervention" (NHLB, NIH, http://www.nih.gov/health/health-topics/topics/angioplasty/risks.html, Aug. 28, 2014).
Souckova et al. Impaired bioavailability and antiplatelet effect of high-dose clopidogrel in patients after cardiopulmonary resuscitation (CPR). Eur J. Clin Pharmacol 2013; 69: 309-17.
Steinhuble et al. Early and sustained dual oral antiplatelet therapy following percutaneous coronary intervention: a randomized controlled trial. JAMA 2002; 288: 2411-20 [Erratum, JAMA 2003; 289: 987].
Surbel P.A. et al. Drug insight: Clopidogrel nonresponsiveness. Nature Clin Pract Cardiovasc Med 3:387-95 (2006).
Festa, L., et al., Current Concepts on Antiplatelet Therapy: Focus on the Novel Thienopyridine and Non-Thienopyridine Agents, Advances in Hematology, 2010, pp. 1-7, vol. 2010, Article ID 595934.
Wallentin L. et al., Ticagrelor versus clopidogrel in patients with acute coronary syndromsyndromes. N. Engl J. Med 361:1045-57 (2009).
Yousuf et al. the evolution of antiplatelet therapy in cardiovascular disease. Nat Rev Cardiol 2011: 8: 547-59.
Yusuf et al. Effects of Clopidogrel in Addition to Aspirin in Patients with Acute Coronary Syndromes without St-Segment Elevation. N Engl J. Med 2001; 345; 494-502.
Bavry A. A. et al., Appropriate use of drug-eluting stents: balancing the reduction in restenosis with the concern of late thrombosis Lancet 371:2134-33 (2008).
Bhatt D. L. Intensifying platelet inhibition—navigating between Scylia and Charybdis. N Engl J. Med 357:2078-81 (2007).
Shaft D.L. Prasugrel in clinical practice. N. Engl J Med 361:940-2 (2009).
Chesebro J.H. et al., Thrombolysis in Myocardial Infarction (TIMI) Trial, Phase I: A comparison between intravenous tissue plasminogen activator and intravenous streptokinase. Clinical findings through hospital discharge. Circulation 76: 142-54(1987).
Collet J.P. et al., Cylochrome P4502C19 polymorphism in young patients treated with clopidogrel after myocardial infarction: a cohort study. Lancet 373:309-17 (2009).
Cullip D.E. et al., Clinical end points in coronary stent trials: a case for standardized definitions. Circulation 115:2344-51 (2007).

(56) References Cited

OTHER PUBLICATIONS

Dovlatova et al., "Competition Between Reversible and Irreversible P2Y12 Antagonists and its iNfluence on ADP-Mediated Platelet Activation," Journal of Thrombosis and Haemostasis, 5(Suppl. 2), Abstract No. S-340 (2007).

Firstenberg, M.S., et al., Safety and Efficacy of Cangrelor, an Intravenous, Short-Acting Platelet Inhibotor in Patients Requiring Coronary Artery Bypass Surgery, The Heart Surgery Forum, 2013, pp. E60-E69, vol. 16, N. 2.

Gruntzig A.R. et al., Nonoperative diatation of coronary-artery stenosis: percutaneous transluminal coronary angioplasty. N. Engl J. Med 301:61-8 (1979).

Gurbel P.A. et al., Drug Insight: Clopidogrel nonresponsiveness. Nature Clin Pract Cardiovasc Med 3:387-95 (2006).

Gurbel P.A. et al., The relation of dosing to clopidogrel responsiveness and the incidence of high post-treatment platelet aggregation in patients undergoing coronary stenting. J Am Coll Cardiol 45: 1392-6 (2005).

International Conference on Harmonization (ICH) Guidance Documents. U.S. Food and Drug Administration Web site. Accessed on Oct. 8, 2009, at the FDA website beginning with "www". and ending with "fda.gov/Regulatoryinformation/Guidances/ucm 122049. htm".

King S.B. 3rd et al., 2007 Focused Update of the ACC/AHA/SCAI 2005 Guideline Update for Percutaneous Coronary Intervention: a report of the American College of Cardiology /American Heart Association Task Force on Practice Guidelines: 2007 Writing Group to Review New Evidence and Update the ACC/AHA/SCA 2005 Guideline Update for Percutaneous Coronary Intervention, Writing on Behalf of the 2005 Writing Committee, Circulation 117:261-95 (2008).

Leonardi S, Koehler ML, Truffa A, et al., A novel approach to implement the universal definition of myocardial infarction in patients undergoing very early invasive management: insights from the CHAMPION Platform trial, AHA Orlando, FL Nov. 12-16, 2011.

Mahaffey K.W., et al., Misreporting of myocardial infarction end points: results of adjudication by a central clinical events committee in the Paragon-B trial, Second Platelet IIb/Ia Antagonist for the Reduction of Acute Coronary Syndrome Events in a Global Organization Network Trial. Am Heart J 143; 242-8 (2002).

Maisel W.H., Unanswered Questions—Drug-Eluting Stents and the Risk of Late Thrombosis N Engl J Med 356:981-4 (2007).

Meadows T.A. et al. Clinical aspects of platelet inhibitors and thrombus formation. Circ Res 100:1261-75 (2007).

Mega J.L. et al., Cytochrome p-450 polymorphisms and response to clopidogrel. N Engl J. Med 360:354-62 (2009.

NCT00305162 Clinical Trials.gov Archive, https://clinicaltrials.gov/ct2/archive/NCT00305162, May 19, 2009.

Popma J.J. et al., Antithrombotic therapy during percutaneous coronary intervention: the Seventh ACCP Conference on Antithrombotic Therapy Chest 126:576S-99S (2004).

Ravnefjord et al. Evaluation of ticagrelor pharmacodynamic interations with reversibly binding or non-reversibly binding P2Y(12) antagonists in an ex-vivo canine model. Thromb Res. Oct. 2012;130(4):622-8.

Schomig A. et al., Ticagrelor—is there need for a new player in the antiplatelet-therapy field? N Engl J. Med 361:1108-11 (2009).

Silber S. et al., Guidelines for percutaneous coronary interventions. The Task Force for Percutaneous Coronary Interventions of the European Society of Cardiology. Eur Heart J. 26:804-47 (2005).

Steg, P.G. et al. Ticagrelor Versus Clopidogrel in Patients With ST-Elevation Acute Coronary Syndromes Intended for Reperfusion With Primary Percutaneous Coronary Intervention A Platelte Inhibition and Patient Outcomes (PLATO) Trial Subgroup Analysis. Circulation, 2010, pp. 2131-2141, vol. 122, No. 3.

Stone G.W. et al., Bivalirudin for patients with acute coronary syndromes. N Engl J Med 355:2203-16 (2006).

Stone G.W. et al., Paclitaxel-eluting stents versus bare-metal stents in acute myocardial infarction. N Engl J Med 360:1946-59 (2009).

The article "What are the risks of percutaneous coronary intervention" (NHLBI, NIH. http://www.nhlbi.nih.gov/health/health-topics/topics/angioplasty/risks html, Aug. 28, 2014.

The GUSTO Investigators. An international randomized trial comparing four thrombolylic strategies for acute myocardial infarction. N Engl J Med 329:673-82 (1993).

Thygesen K. et al., Universal definition of myocardial infarction. Circulation 116:2634-53 (2007).

Trissel et al. Turbidimetric assessment of the compatibility of taxol with 42 other drugs during simulated Y-site injection. Am J Hosp Pharm, 49:1716-9 (1992).

Trissel L.A. et al., Physical compatibility of melphalan with selected drugs during simulated Y-site administration. Am J Hosp Pharm 50:2359-63 (1993).

Windecker S. et al., Late Coronary Stent Thrombosis Circulation 116: 1952-65 (2007).

Wiviott S.D. et al. Prasugrel Versus clopidogrel in patients with acute coronary syndromes. N Engl J.Med 357:2001-15 (2007).

Bavry et al. Benefit of early invasive therapy in acute coronary syndromes: a meta-analysis of contemporary randomized clinical trials. J Am Coll Cardiol. Oct. 3, 2006;48(7):1319-25.

Bhatt DL. To Cath or Not to Cath That is No Longer the Question. JAMA. 2005;293(23):2935-2937.

Bhatt et al. Utilization of early invasive management strategies for high risk patients with non-ST-segment elevation acute coronary syndromes: results from the CRUSADE Quality Improvement Initiative. JAMA. Nov. 3, 2004;292 (17):2096-104.

Chattaraj SC, Cangrelor astra Zeneca, Curr Opin Investig Drugs, 2001, pp. 250-255, vol. 2, No. 2.

Heestermans et al. Impaired bioavailability of clopidogrel in patients with a ST-segment elevation myocardial infarction. Thromb Res 2008; 122: 776-81.

Leonardi S, Stebbins A. Lopes RD, et al., Maintenance therapy with thienopyridines may reduce enzymatic infarct size in patients with acute coronary syndrome undergoing PCI: Insights form the CHAMPION PCI trial AHA Chicago, IL, 2010.

Mehta et al. Effects of pretreatment with clopidogrel and aspirin followed by long-tern therapy in patients undergoing percutaneous coronary intervention: the PCI-CURE study, Lancet 2001; 358:527-33.

Sabatine et al. Addition of clopidogrel to aspirin and fibrinolytic therapy for myocardial infarction with ST-segment elevation. N Engl J Med 2005; 256: 1179-89.

Mehta S R, et al., Routine vs selective invasive strategies in patients with acute coronary syndromes: a collaborative meta-analysis of randomized trials, JAMA 2005; 293:2908-17.

Abbracchio MP, et al., International union of pharmacology LVIII: update on the P2Y G protein-coupled nucleotide receptors: from molecular mechanisms and pathophysiology to therapy, Pharmacol Rev, 2006, pp. 281-341, vol. 58, No. 3.

Aleil B, et al., Flow cytometric analysis of intraplatelet VASP phosphorylation for the detection of clopidogrel resistance in patients with ischemic cardiovascular diseases, J Thromb Haemost, 2005, pp. 85-92.

Angiolillo DJ, ADP Receptor Antagonism. What's in the Pipeline?, Am J Cardiovasc Drugs, 2007, pp. 423-432. vol. 7 No. 6.

Angiolillo DJ, et al., Pharmacology of emerging novel platelet inhibitors, Am Heart J, 2008, pp. S10-S15, vol. 156, No. 2, Supp. 1.

Angiolillo DJ, et al., Clinical overview of promising nonthienopyridine antiplatelet agents, Am Heart J, 2008, pp. S23-S28, vol. 156, No. 2, Supp 1.

Becker RC, Platelet surface physiology and its importance in pharmacotherapy design and development: The adenosine diphosphate receptor antagonists, J Thromb Thrombolysis, 2000, pp. 35-53.

Boeynaems JM, Van Giezen H, Savi P, Herbert JM, P2Y receptor antagonists in thrombosis, Curr Opin Investig Drugs, 2005, pp. 275-282, vol. 6, No. 3.

Cattaneo M, Platelet P2 receptors: old and new targets for antithrombotic drugs, Expert Rev Cardiovasc Ther, 2007, pp. 45-55, vol. 5, No. 1.

(56) References Cited

OTHER PUBLICATIONS

Christensen K, Larsson R, Emanuel Sson H, et al., Effects on blood compatibility in vitro by combining a direct P2Y12 receptor inhibitor and heparin coating of stents, Platelets, 2006, pp. 318-327, vol. 17, No. 5.
Cohen M, Diez J, Levine GN, et al., Pharmacoinvasive management of acute coronaiy syndrome: incorporating the 2007 ACC/AHA Guidelines. The CATH (Cardiac Catherization and Antithrombotic Therapy in the Hospital) Clinical Consensus Panel Report-III, J Invasive Cardiology, 2007, pp. 525-540, vol. 19, No. 12.
Dalal AR, D'Souza S, Shulman MS, Brief review: coronaiy drug-eluting stents and anesthesia, Can J Anaest, 2006, pp. 1230-1243, vol. 53, No. 12.
Diaz-Ricart M, Cangrelor tetrasodium, Drugs of the Future, 2008, pp. 101-110, vol. 33, No. 2.
Ding Z, Kim S, Kunapuli SP, Identification of a potent inverse agonist at a constitutively active mutant of human P2Y12 receptor, Mol Pharmacol, 2005, pp. 338-345, vol. 69, No. 1.
Dovlatova NL, Jakubowski JA, Sugidachi A, et al., The reversible P2Y12 antagonist cangrelor influences the ability of the active metabolites of clopidogrel and prasugrel to produce irreversible inhibition of platelet function, J Thromb Haemost, 2008, pp. 1153-1159, vol. 6.
Dovlatova N, Wijeyeratne YD, Fox SC, et al., Detection of P2Y(14) protein in platelets and investigation of the role of P2Y(14) in platelet function in comparison with the EP(3) receptor, Thromb Haemost, 2008, pp. 261-270, vol. 100.
Fugate SE, Cudd LA, Cangrelor for treatment of coronary thrombosis, Ann Pharmacother, 2006, pp. 925-930, vol. 40.
Gitt AK, Betriu A., Antiplatelet therapy in acute coronary syndromes, Eur Heart J, 2008, pp. A4-AI2, 10 Supp. A.
Greenbaum AB, Ohman EM, Gibson CM, et al., Preliminary experience with intravenous P2Y12 platelet receptor inhibition as an adjunct to reduced-dose alteplase during acute myocardial infarction: Results of the Safety, Tolerability and Effect on Patency in Acute Myocardial Infarction (STEP-AMI) angiographic trial, Am Heart J, 2007 pp. 702-709, vol. 54, No. 4.
Greenbaum AB, Grines CL, Bittl JA, et al., Initial experience with an intravenous P2Y12 platelet receptor antagonist in patients undergoing percutaneous coronary intervention: Results from a 2-part, phase II, multicenter, randomized, placebo- and active-controlled trial, Am Heart J, 2006, pp. 689.e1-689.e10.
Greenbaum AB, Ohman EM, Gibson MS, et al., Intravenous adenosine diphosphate P2T platelet receptor antagonism as an adjunct to fibrinolysis for acute myocardial infarction, JACC, 2002, pp. , vol. 39, Issue 5, Supp. A.
Huang J, Driscoll EM, Gonzales ML, Prevention of arterial thrombosis by intravenously administered platelet P2T receptor antagonist AR-C66931MX in a canine model, J Pharmacol Exp Ther, 2000, pp. 492-499, vol. 295, No. 2.
Humphries RG, Pharmacology of AR-C69931MX and related compounds: from pharmacological tools to clinical trials, Haematologica, 2000, pp. 66-72, 85(the Platelet ADP Receptors Supp.).
Ingall AH, P2T receptor antagonists: novel inhibitors of platelet aggregation, Arch Pharm, 1999, pp. 11-12, Supp. 1.
Ingall AH, Dixon J, Bailey A, et al., Antagonists of the platelet P2T receptor: a novel approach to antithrombotic therapy, J Med Chem, 1999, pp. 213-220, vol. 42.
Jacob Sson F, Swahn E, Wallentin L, et al., Safety profile and tolerability of intravenous AR C69931MX, a new antiplatelet drug, in unstable angina pectoris and non Q wave myocardial infarction, Clin Ther, 2002, pp. 752-765, vol. 24, No. 5.
Jacob Sson F, Dellborg M, Swahn E, et al., JACC, 2000, p. 343, vol. 35, Issue, 2, Supp. A.
Jarvis GE, Nassim MA, Humphries RG, et al., The P2T antagonist AR C69931MX is a more effective inhibitor of ADP induced platelet aggregation than clopidogrel. Blood, 1999, p. 194, (10 Supp. pt. 1):22a.
Jarvis GE, Nassim MA, Humphries RG, et al., Superior inhibition of ADP induced human platelet aggregation by AR C69931MX than clopidogrel, Drug Dev Res, 2000, p. 90. vol. 50, No. 1.
Judge HM, Buckland RJ, Holgate CE, et al, Glycoprotein Ith/IIIa and P2Y12 receptor antagonists yield additive inhibition of platelet aggregation, granule secretion, soluble CD4OL release and procoagulant responses, Platelets, 2005, pp. 398-407, vol. 16, No. 7.
Kandzari DE, Evolving antithrombotic treatment strategies for acute ST-elevation myocardial infarction, Rev Cardiovasc Med, 2006, pp. S29-S37, vol. 7, Supp. 4.
Kuijpers MJ, Nieuwenhuys CM, Feijge MA, et al., Regulation of tissue factor-induced coagulation and platelet aggregation in flowing whole blood, Thromb Haemost, 2005; 93, pp. 97-105.
Kunapuli SP, Ding Z, Dorsam RT, et al., ADP receptors target for developing antithrombotic agents, Curr Pharm Des, 2003, vol. 9, pp. 2303-2316.
Leon C, Alex M, Klocke A, et al., Platelet ADP receptors contribute to the initiation of intravascular coagulation, Blood, 2004, pp. 594-600, vol. 103, No. 2.
Mazzucato M, Cozzi MR, Pradella P, et al., Crucial role of the ADP receptor P2Y1 in platelet adhesion and signaling under high flow, Blood, 2002, p. 100, 11.
Michelson AD, P2Y12 Antagonism. Promises and challenges, Arterioscler Thromb Vasc Biol, 2008, pp. S33-S38.
Murugappan S, Kunapuli S, The role of ADP receptors in platelet function, Front Biosci, 2006, pp. 1977-1986, vol. 11.
Nassim MA, Sanderson JB, Clarke C, et al., Investigation of the novel P2T receptor antagonist AR C69931MX on ex vivo adenosine diphosphate induced platelet aggregation and bleeding time in healthy volunteers, JACC, 1999, p. 33, vol. 33 (Supp A).
Niitsu Y, Jakubowski JA, Sugidachi A, et al., Pharmacology of CS-747 (Prasugrel, LY640315), a novel, potent antiplatelet agent with in vivo P2Y12 receptor antagonist activity, Semin Thromb Hemost, 2005, pp. 184-194, vol. 31, No. 2.
Nogard NB, Abu-Fadel M, Future prospects in anti-platelet therapy: A review of potential P2Y12 and thrombin receptor antagonists, Recent Patents Cardiovasc Drug Discovery, 2008, pp. 194-200, vol. 3.
Nurden AT, Nurden P, Advantages of fast-acting ADP receptor blockade in ischemic heart disease (Editorial to K. Wang article p. 357), Arterioscler Thromb Vasc Biol, 2003, pp. 158-159.
Nylander S, Mattsson C, Lindahl TL, Characterisation of species differences in the platelet ADP and thrombin response, Thromb Res, 2003, pp. 65-73, vol. 111.
Park SJ, Lee SW, Optimal management of platelet function after coronary stenting, Curr Treat Options Cardiovasc Med, 2007, pp. 37-45.
Parravicini C, Ranghino G, Abbracchio MP, et al., GPR17: Molecular modeling and dynamics studies of the 3-D structure and purinergic ligand binding features in comparison with P2Y receptors, BMC Bioinformatics, 2008, pp. 1-19, vol. 9, No. 263.
Penz SM, Reininger AJ, Toth 0, et al., Glycoprotein Iba inhibition and ADP receptor antagonists, but not aspirin, reduce platelet thrombus formation in flowing blood exposed to atherosclerotic plaques, Thromb Haemost, 2007, pp. 435-443, vol. 97.
Price MJ, New anti platelet therapies in development, Am J Health-Syst Pharm, 2008, pp. S11-S15, vol. 65.
Raju NC, Eikelboom JW, Hirsh J, Platelet ADP-receptor antagonists for cardiovascular disease: past, present and future, Nat Clin Pract Cardiovasc Med, 2008, pp. 766-780, vol. 5, No. 12.
Rich J, Wivioitt SD, New antiplatelet therapies for acute coronary syndromes, Curr Cardiol Rep, 2007, pp. 303-311, vol. 9.
Steinhubl SR, Oh JJ, Oestreich JH, et al., Transitioning patients from cangrelor to clopidogrel: Pharmacodynamic evidence of a competitive effect, Thromb Res, 2007, pp. 527-534, vol. 121.
Steinhubl S, Roe MT, Optimizing platelet P2Y12 inhibition for patients undergoing PCI, Cardiovasc Drug Rev, 2007, pp. 188-203, vol. 25, No. 2.
Storey RF, Oldroyd KG, Wilcox RG, First clinical study of the novel platelet ADP receptor (P2T) antagonist AR-C69931MX, assessing safety, tolerability and activity in patients with acute coronary syndromes, Circulation, 1999, p. 1-170 vol. 100, No. 18.

(56) References Cited

OTHER PUBLICATIONS

Storey RF, Sanderson HM, White AE, et al., The central role of the P(2T) receptor in amplification of human platelet activation, aggregation, secretion and procoagulant activity, Br J Haematol, 2000, pp. 925-934, vol. 110.

Storey RF, Cameron KE, Pascoe JS, et al., Potential therapeutic effect of the novel platelet adenosine diphosphate receptor (P2T) antagonist, AR C69931MX, as assessed by in vitro studies in human whole blood. A possible adjunct to aspirin therapy?, Eur Heart J, 1998, p. 493, 19(SUPP):54.

Storey RF, Oldroyd KG, Wilcox RG, Open multicentre study of the P2T receptor antagonist AR-C69931MX assessing safety, tolerability and activity in patients with acute coronary syndromes, Thromb Haemost, 2001, pp. 401-407, vol. 85.

Storey RF, Variability of response to antiplatelet therapy, Eur Heart J, 2008, pp. A21-A27, 10(SUPP A).

Storey RF, New developments in antiplatelet therapy, Eur Heart J, 2008, pp. D30-D37, 10 (SUPP D).

Storey RF, Clinical experience with antithrombotic drugs acting on purine receptor pathways, Drug Dev Res, 2001, pp. 202-212, vol. 52.

Storey RF, The P2Y12 receptor as a therapeutic target in cardiovascular disease, Platelets, 2001, pp. 197-209, vol. 12.

Storey RF, Wilcox RG, Heptinstall S, Comparison of the pharmacodynamic effects of the platelet ADP receptor antagonists clopidogrel and AR-C69931MX in patients with ischaemic heart disease, Platelets, 2002, pp. 407-413, vol. 13.

Storey RF, Judge HM, Wilcox RG, et al., Inhibition of ADP-induced p-selection expression and platelet-leukocyte conjugate formation by clopidogrel and the P2Y12 receptor antagonist AR-C69931MX but not aspirin, Thromb Res, 2002, pp. 488-494, vol. 88.

Harrington RA, Stone GW, Mcnulty S, et al., Platelet inhibition with cangrelor in patients undergoing PCI, N Engl J Med, 2009, pp. 2318-2319, vol. 361.

Yu D, Glenn JR, White AE, et al., Mode of action of P2Y12 antagonists as inhibitors of platelet function, Thromb Haemost, 2011, pp. 96-105, vol. 105.

Iyu D, Glenn White et al., Adenosine derived from ADP can contribute to inhibition of platelet aggregation in the presence of a P2Y12 antagonist, Arterioscler Thromb Vasc Biol, 2011, pp. 416-422, vol. 31.

Leonardi S, Mahaffey KW, White HD, et al., Rationale and design of the cangrelor versus standard therapy to acHieve optimal management of platelet inhibitiON PHOENIX trial, Am Heart J, 2012, pp. 768-776.e2, vol. 163.

Leonardi S, Stebbins A, Lopes RD, et al., Maintenance therapy with thienopyridines may reduce enzymatic infarct size in patients with acute coronary syndrome undergoing PCI: Insights from the CHAMPION PCI trial, AHA Chicago, IL, 2010.

Leonardi S, Truffa AA, Neely LM, et al., A novel approach to systematically implement the universal definition of myocardial infarction: insights from the CHAMPION PLATFORM trial, Heart, 2013, pp. 1282-1287, vol. 99.

Testa L, Biondi Zoccai GG, Valgimigli M, et al., Current concepts on antiplatelet therapy: focus on the novel thienopyridine and non-thienopyridine agents, Adv.

Ueno M, Ferreiro JL, Angiolillo DJ, Update on the clinical development of cangrelor, Expert Rev Cardiovasc, 2010, pp. 1069-1077, vol. 8L.

White HD, Chew DP, Dauerman HL, et al., Reduced immediate ischemic events with cangrelor in PCI: A pooled analysis of the CHAMPION trials using the universal definition of myocardial infarction, Am Heart J, 2012, pp. 182-190.e4, vol. 163.

Bhatt DL, Stone GW, Mahaffey KW, et al. Effect of platelet inhibition with cangrelor during PCI on ischemic events. N Engl J Med, 2013, pp. 1303-1313, vol. 368.

Ahrens I, Bode C, Novel antiplatelet therapies following percutaneous coronary interventions, Cun- Opin Investig Drugs, 2009, pp. 902-911, vol. 10.

Akers WS, Oh JJ, Oestreich 111, et al., Pharmacokinetics and Pharmacodynamics of a bolus and infusion of cangrelor: a direct, parenteral P2Y12 receptor antagonist, J Clin Phann, 2010, pp. 27-35, vol. 50.

Angiolillo DJ, Schneider DJ, Bhatt DL, et al., Phannacodynamic effects of cangrelor and clopidogrel: the platelet function sub study from the cangrelor versus standard therapy to achieve optimal management of platelet inhibition (CHAMPION) trials, J Thromb Thrombolysis, 2012, pp. 44-55, vol. 44.

Angiolillo DJ, Firstenberg MS, Price MJ, et al., Bridging antiplatelet therapy with cangrelor in patients undergoing cardiac surgery, JAMA, 2012, pp. 265-274 and Supplemental Online Content, vol. 307, No. 3.

Bellemain-Appaix A, Brieger D, Beygiu F, et al., New P2Y12 inhibitors versus clopidogrel in percutaneous coronary intervention. A meta-analysis, J Am Coll Cardiol, 2010, pp. 1542-1551, vol. 56.

Bhatt DL, Lincoff AM, Gibson CM, et al., Intravenous platelet blockade with cangrelor during PCI, N Engl J Med, 2009, pp. 2330-2341, vol. 361.

Buckland RJ, Judge HM, Sugidachi A, et al., Reversible binding of cangrelor to the P2Y12 receptor prevents the binding of clopidogrel and prasugrel active metabolites, J Thromb Haemost, 2009, p. 942, vol. 7(Suppl 2).

Buckland R, Judge HM, Sugidachi A, et al., Cangrelor inhibits the binding of clopidogrel and prasugrel active metabolites to the P2Y12 receptor, Eur Heart J, 2009, p. 193, vol. 30(Suppl 1).

Desai NR, Bhatt DL, The state of periprocedural antiplatelet therapy after recent trials, J Am Coll Cardiol Intv, 2010, pp. 571-583, vol. 3.

Faxon DP, Cangrelor for ACS lessons from the CHAMPION trials, Nat Rev Cardiol, 2010, pp. 124-125, vol. 7.

Ferreiro JL, Ueno M, Angiolillo DJ, Cangrelor: a review on its mechanism of action and clinical development, Expert Rev Cardiovasc Ther, 2009, pp. 1195-1201, vol. 7.

Fox SC, May JA, Johnson A, et al., Effects on platelet function of an EP3 receptor antagonist used alone and in combination with a P2Y12 antagonist both in-vitro and ex-vivo in human volunteers, Platelets, 2013, pp. 392-400, vol. 24, No. 5.

Oestreich 111, Steinhubl SR, Cangrelor in percutaneous coronary intervention, Expert Rev Clin Phanncol, 2009, pp. 137-145, vol. 2.

Oliphant CS, Doby JB, Blade CL, et al., Emerging P2Y12 receptor antagonists:role in coronary artery disease, Curr Vasc Phannacol, 2010, pp. 93-101, vol. 8.

Hall R, et al., Antiplatelet drugs: a review of their pharmacology and management in the perioperative period, Anesthesia & Analgesia, 2011, pp. 292-318, vol. 112, No. 2.

NCT00767507 Clinical Trials.gov Archive, https://clinicaltrials.gov/archive/NCT00767507/2011_08_08, Aug. 8, 2011.

NCT00767507 Clinical Trials.gov Archive, https://clinicaltrials.gov/archive/NCT00767507/200_10_06, Oct. 6, 2008.'.

Debruyne et al. Fractional Flow Reserve—Guided PCI versus Medical Therapy in Stable Coronary Disease. N. Engl J. Med 2012, 367: 991-1001 [Erratum, N. Engl J Med 2012, 367:1768].

Feldman et al. Impact of Bivalirudin on outcomes after percutaneous coronary revascularization with drug-eluting stents. American Heart Journal. Oct. 2007. vol. 154, No. 4, pp. 695-701.

Gitt AK, Betriu A., Antiplatelet therapy in acute coronary syndromes, Eur Heart J. 2008, pp. A4-A12, 10 Supp. A.

Norgard NB, Cangrelor: A novel P2Y12 receptor antagonist, Expert Opin Investig Drugs, 2009, pp. 1219-1230, vol. 18.

Paikin JS, Eikelboom JW, Cairns JA, et al., New Antithrombotic agents—insights from clinical trials, Nat Rev Cardiol, 2010, pp. 498-509, vol. 7.

Matejtschuk, 2007, Lyophilization of Proteins, Methods in Molecular Biology (eds JG Day and GN Stacey), pp. 69-72.

Schneider et al. (Coronary Artery Disease Mar. 2009, vol. 20, No. 2, pp. 175-178).

Steinhubl et al. (Thrombosis Research 2008, 121, pp. 527-534).

Thygesen et al. Universal definition of myocardial infarction: Kristian Thygesen, Joseph S. Alpert and Harvey D. White on behalf of the Joint ESCIACCF/AHA/WHF Task Force for the Redefinition of Myocardial Infarction. Eur Heart J 2007; 28 (20): 2525-2538.

(56) References Cited

OTHER PUBLICATIONS

Trissel et al., Turbidimetric assessment of the compatibility of taxol with 42 other drugs during simulated Y-site Injection. Am J Hosp Pharm 50:300-4 (1993).

* cited by examiner

METHODS OF TREATING, REDUCING THE INCIDENCE OF, AND/OR PREVENTING ISCHEMIC EVENTS

CROSS REFERENCE TO RELATED APPLICATIONS

This application is a continuation of U.S. application Ser. No. 14/050,266, filed on Oct. 9, 2013, which is a continuation-in-part of U.S. application Ser. No. 13/792,056, filed on Mar. 9, 2013, which has issued on Aug. 30, 2016 as U.S. Pat. No. 9,427,448, and which is a continuation-in-part of U.S. application Ser. No. 12/943,717, filed on Nov. 10, 2010, which has issued on Mar. 27, 2018 as U.S. Pat. No. 9,925,265, and which claims the benefit of U.S. provisional application Ser. No. 61/260,361, filed on Nov. 11, 2009. Additionally, this application is a continuation of U.S. application Ser. No. 14/050,266, filed on Oct. 9, 2013, which is also a continuation-in-part of U.S. application Ser. No. 12/943,717, filed on Nov. 10, 2010, which has issued on Mar. 27, 2018 as U.S. Pat. No. 9,925,265, and which claims the benefit of U.S. provisional application Ser. No. 61/260,361, the contents of each of the above applications are incorporated by reference herein, in their entireties and for all purposes.

FIELD OF THE INVENTION

The present invention relates to methods of treating, reducing the incidence of, and/or preventing an ischemic event in a patient undergoing percutaneous coronary intervention (PCI), comprising administering to the patient a pharmaceutical composition comprising cangrelor. The methods may further comprise administering an additional therapeutic agent to the patient, the additional therapeutic agent comprising bivalirudin or a $P2Y_{12}$ inhibitor. The present invention also relates to pharmaceutical compositions useful for treating, reducing the incidence of, and/or preventing an ischemic event in a patient undergoing PCI. The pharmaceutical compositions comprise cangrelor, and optionally bivalirudin. The present invention further relates to methods of preparing a pharmaceutical composition for treating, reducing the incidence of, and/or preventing an ischemic event in a patient undergoing PCI, comprising admixing cangrelor with one or more pharmaceutically acceptable excipients. An ischemic event may include stent thrombosis, myocardial infarction, ischemia-driven revascularization (IDR), and mortality.

BACKGROUND OF THE INVENTION

PCI is a procedure that opens narrowed arteries that supply heart muscle with blood. PCI with stent implantation is widely used to reduce the risk of mortality or myocardial infarction in patients with acute coronary syndromes and to reduce the burden of angina and improve the quality of life in patients with stable angina.[1] However, thrombotic complications during PCI are a major concern, particularly if the procedure involves implantation of a stent, which can induce platelet adhesion, activation and thrombus formation on or near the stent.[2] Thus, antiplatelet therapies are an important adjunct to PCI.[3]

[1] Mehta S R, et al., JAMA 2005; 293:2908-17; De Bruyne B, et al., N Engl J Med 2012; 367:991-1001 [Erratum, N Engl J Med 2012; 367:1768.]; Bhatt D L, JAMA 2005; 293:2935-7; Bavry A A, et al., J Am Coll Cardiol 2006; 48:1319-25; and Bhatt D L, et al., JAMA 2004; 292:2096-104.
[2] Windecker S, et al., Circulation 2007; 116:1952-65; Maisel W H, N Engl J Med 2007; 356:981-4.
[3] Grüntzig A R, et al., N Engl J Med 1979; 301:61-8.

Inhibition of platelet adenosine diphosphate (ADP) receptor $P2Y_{12}$ through pharmacotherapy has been demonstrated to improve cardiovascular outcomes in patients undergoing PCI.[4] Such antiplatelet therapies reduce the risk of ischemic events, particularly stent thrombosis.[5] Yet, there are several limitations regarding the use of orally administered $P2Y_{12}$-receptor inhibitors. For instance, there is a delayed onset of action when these drugs are administered, even when given with a loading dose,[6] which is particularly problematic for patients who require urgent or periprocedural treatment. In addition, patients in the acute phase of cardiovascular illness may have conditions such as nausea, impaired absorption, or impaired perfusion that can limit drug bioavailability; in such patients the antiplatelet effect of oral antiplatelet agents such as clopidogrel may not be sufficient.[7] Further, multiple studies have now demonstrated that the pharmacokinetic and pharmacodynamic effects of clopidogrel are highly variable[8] and may be influenced by genetic polymorphisms,[9] which translate into differential pharmacodynamic and therapeutic responses that lead to the notion of clopidogrel "non-responders."[10] Moreover, many physicians refrain from administering clopidogrel prior to angiographic definition of coronary anatomy, as this irreversible platelet inhibitor has been associated with an increased risk of perioperative bleeding if coronary artery bypass surgery is required rather than percutaneous revascularization. More potent oral ADP blockers have been tested and found to reduce ischemic outcomes even further, but with increased rates of bleeding.[11]

[4] Yusuf S, et al., N. Eng J Med 2001; 345:494-502; Mehta S R, et al., Lancet 2001; 358:527-33; Sabatine M S, et al., N Engl J Med 2005; 352:1179-89; and Steinhubl S R, et al., JAMA 2002; 288:2411-20 [Erratum, JAMA 2003; 289:987.].
[5] Yousuf O, et al., Nat Rev Cardiol 2011; 8:547-59; Wiviott S D, et al., N Engl J Med 2007; 357:2001-15; Wallentin et al., N Engl J Med 2009; 361:1045-57; and Bhatt D L, N Engl J Med 2007; 357:2078-81.
[6] Meadows T A, et al., Circ Res 2007; 100:1261-75.
[7] Součlová L, et al., Eur J Clin Pharmacol 2013; 69:309-17 and Heestermans A A, et al., Thromb Res 2008; 122:776-81.
[8] Gurbel P A, et al., J Am Coll Cardiol 2005; 45:1392-6 and Collet J P, et al., Lancet 2009; 373:309-17.
[9] Mega J L, et al., N Engl J Med 2009; 360:354-62.
[10] Gurbel P A, et al., Nature Clin Pract Cardiovasc Med 2006; 3:387-95.
[11] Wiviott S D, et al., N Engl J Med 2007; 357:2001-15; Bhatt D L, N Engl J Med 2007; 357:2078-81; Bhatt D L, N Engl J Med 2009; 361:940-2; Wallentin L, et al., N Engl J Med 2009; 361:1045-57; and Schomig A, et al., N Engl J Med 2009; 361:1108-11.

Thus, despite advances in adjunctive pharmacotherapy, the concern of ischemic events in a patient undergoing PCI has not been eliminated.[12] Accordingly, there is a continuing need for a potent, fast-acting, reversible antiplatelet agent that effectively treats, reduces the incidence of, and/or prevents ischemic events without an excessive risk of bleeding.

[12] Stone G W, et al., N Engl J Med 2009; 360:1946-59 and Bavry A A, et al., Lancet 2008; 371:2134-33.

SUMMARY OF THE INVENTION

The present invention demonstrates how cangrelor may be utilized in treating, reducing the incidence of, and/or preventing an ischemic event. An ischemic event may include stent thrombosis, myocardial infarction, IDR, and mortality. An ischemic event can occur before, during, or after PCI.

An aspect of the present invention is directed to a method of treating, reducing the incidence of, and/or preventing an ischemic event in a patient undergoing PCI. The method comprises administering to the patient a pharmaceutical composition comprising cangrelor. The pharmaceutical composition may be administered before, during, and/or after PCI, and through various routes of administration. For example, the pharmaceutical composition may be administered intravenously, including as a bolus and/or infusion. In addition, the pharmaceutical composition may be administered to a patient undergoing PCI involving stent implantation. The method of the present invention may treat, reduce the incidence of, and/or prevent an ischemic event during or after PCI. In some instances, the method is not accompanied by a significant increase in severe bleeding or the need for transfusions.

In certain embodiments of the invention, the method may further comprise administering an additional therapeutic agent to the patient. The additional therapeutic agent may be administered separately from the pharmaceutical composition comprising cangrelor, either sequentially or concurrently. Alternatively, the additional therapeutic agent may be administered in the same pharmaceutical composition as cangrelor. In some embodiments, the additional therapeutic agent comprises a $P2Y_{12}$ inhibitor, such as clopidogrel, prasugrel, or ticagrelor. In particular embodiments, the additional therapeutic agent comprises bivalirudin.

Another aspect of the present invention is directed to a pharmaceutical composition useful for treating, reducing the incidence of, and/or preventing an ischemic event in a patient undergoing PCI. The pharmaceutical composition comprises cangrelor and may further comprise one or more pharmaceutically acceptable excipients. In addition, the pharmaceutical composition may further comprise one or more additional therapeutic agents, for example, bivalirudin. The pharmaceutical composition may be a solid, liquid, or suspension. The pharmaceutical composition of the present invention may be useful for treating, reducing the incidence of, and/or preventing an ischemic event that occurs during or after PCI. In some instances, the pharmaceutical composition does not lead to a significant increase in severe bleeding or the need for transfusions when administered to a patient undergoing PCI.

A further aspect of the present invention is directed to a method of preparing a pharmaceutical composition for treating, reducing the incidence of, and/or preventing an ischemic event in a patient undergoing PCI, comprising admixing cangrelor with a pharmaceutically acceptable excipient. The pharmaceutically acceptable excipient may comprise NaCl, dextrose, mannitol, or a combination thereof. In certain embodiments, the method may further comprise admixing one or more additional therapeutic agents, for example, bivalirudin, with cangrelor.

An additional aspect of the present invention is directed to a kit comprising a pharmaceutical composition of cangrelor and a pharmaceutical composition of an additional therapeutic agent, for example, bivalirudin.

DETAILED DESCRIPTION OF THE INVENTION

Figure 1:
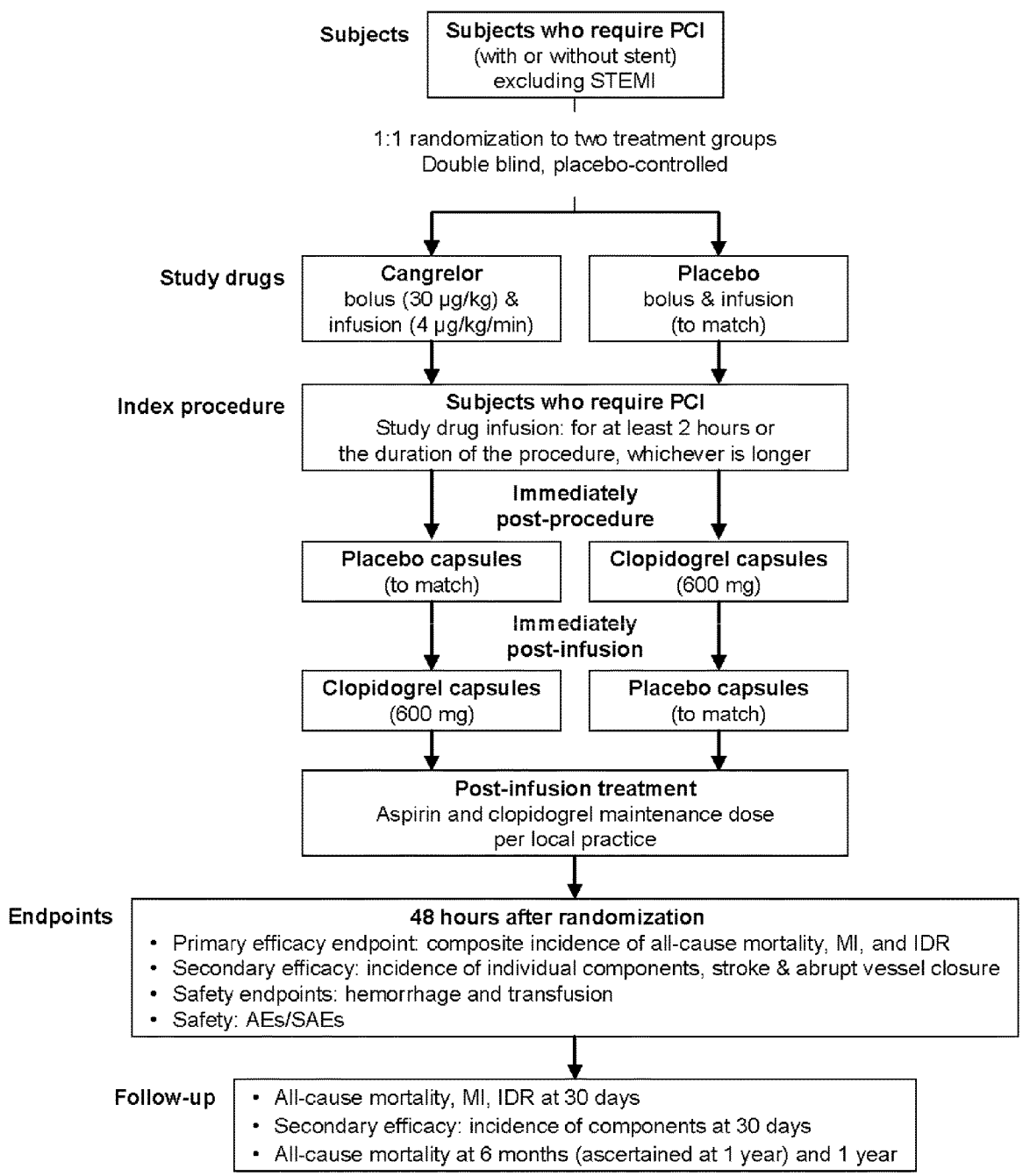
FIG. 1—diagram showing trial design for the study described in Example 1.

The present invention is based on the discovery that cangrelor, a reversible, fast acting, adenosine triphosphate analogue inhibitor of the $P2Y_{12}$ ADP receptor, is effective in treating, reducing the incidence of, and/or preventing an ischemic event. Thus, the present invention is directed to a method of treating, reducing the incidence of, and/or preventing an ischemic event in a patient undergoing PCI, comprising administering to the patient a pharmaceutical composition comprising cangrelor. In some instances, the method may further comprise administering to the patient an additional therapeutic agent, such as bivalirudin. The present invention is also directed to a pharmaceutical composition useful for treating, reducing the incidence of, and/or preventing an ischemic event in a patient undergoing PCI, wherein the pharmaceutical composition comprises cangrelor and may further comprise one or more pharmaceutically acceptable excipients. In some cases, the pharmaceutical composition may further comprise an additional therapeutic agent, such as bivalirudin. Further, the present invention is directed to a method of preparing a pharmaceutical composition for treating, reducing the incidence of, and/or preventing an ischemic event in a patient undergoing PCI, comprising admixing cangrelor with one or more pharmaceutically acceptable excipients. In some instances, the method may further comprise admixing an additional therapeutic agent, such as bivalirudin, with cangrelor.

Cangrelor

Cangrelor is a non-thienopyridine adenosine triphosphate analogue which reversibly binds to and inhibits the $P2Y_{12}$ ADP receptor. Cangrelor is direct-acting, reversible, and selective, and it has a short half-life. It is metabolized through dephosphorylation pathways and has a plasma half-life of 3-5 minutes; platelet function returns to normal within 30-60 minutes of drug termination.[13] When given as a bolus plus infusion, it quickly and consistently inhibits platelets to a high degree with normalization of platelet function shortly after discontinuation. A phase 2 trial in patients undergoing PCI demonstrated dose-dependent platelet inhibition similar to that achieved with abciximab, less bleeding time prolongation, and more rapid return to platelet function.[14] The chemical structure of cangrelor is shown in Formula I.

[13] Storey R F, et al., Br J Haematol 2000; 110:925-34.
[14] Greenbaum A B, et al., Am Heart J 2006; 151:689.e1-10.

Formula I

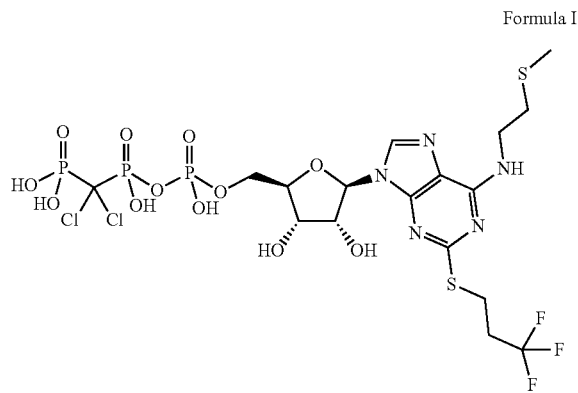 [SMILES: CSCCNc1nc(SCCC(F)(F)F)nc2c1ncn2[C@@H]1O[C@H](COP(=O)(O)OP(=O)(O)C(Cl)(Cl)P(=O)(O)O)[C@@H](O)[C@H]1O]

In each of the embodiments of the present invention, the term "cangrelor" encompasses the compound of Formula I, as well as tautomeric, enantiomeric and diastereomeric forms thereof, and racemic mixtures thereof, and pharmaceutically acceptable salts of these compounds, including a tetrasodium salt. These alternative forms and salts, processes for their production, and pharmaceutical compositions comprising them, are well known in the art and set forth, for example, in U.S. Pat. No. 5,721,219. Additional disclosure relevant to the production and use of cangrelor may be found in U.S. Pat. Nos. 5,955,447, 6,130,208 and 6,114,313, as well as in U.S. Appln. Publication No. 2006/0270607.

Ischemic Events

The present invention demonstrates how cangrelor may be utilized in treating, reducing the incidence of, and/or preventing an ischemic event. An ischemic event may include stent thrombosis, myocardial infarction, IDR, and mortality. An ischemic event can occur before, during, or after PCI.

Stent Thrombosis

In certain embodiments, the present invention relates to treating, reducing the incidence of, and/or preventing stent thrombosis in a patient undergoing PCI. Stent thrombosis may result from any means related to the implantation, presence, or maintenance of the stent in the vasculature of the patient. For example, stent thrombosis may be induced by implantation of a stent into the patient or may develop over time due to the presence of a stent, such as a bare-metal stent, a drug-eluting stent, or other type of stent. In some embodiments, stent thrombosis is defined in accordance with or derived from the Academic Research Consortium definition of stent thrombosis.[15] In certain embodiments of the present invention, stent thrombosis may be intraprocedural stent thrombosis, acute stent thrombosis (<24 hours post implantation), sub-acute stent thrombosis (>24 hours and <30 days post implantation), late stent thrombosis (>30 days and <12 months post implantation) or very late stent thrombosis (>12 months post implantation).

[15] Cutlip D E, et al., Circulation 2007; 115(17):2344-51.

Myocardial Infarction

In certain embodiments, the present invention relates to treating, reducing the incidence of, and/or preventing myocardial infarction in a patient undergoing PCI. Myocardial infarction may be any form of myocardial infarction, including acute myocardial infarction (first few hours to 7 days), healing myocardial infarction (7 to 28 days), healed myocardial infarction (29 days and beyond), acute non-ST-elevated myocardial infarction (NSTEMI), and acute ST-elevated myocardial infarction (STEMI). In some embodiments, myocardial infarction is defined in accordance with or derived from the universal definition of myocardial infarction.[16]

[16] Thygesen K, et al., Eur Heart J 2007; 28:2525-38.

Myocardial infarction may arise during PCI, or may be induced by any mechanism, including implantation of a stent into the patient. Myocardial infarction may also be caused by stent thrombosis or occlusion of a coronary artery.

Ischemia-Driven Revascularization (IDR)

In certain embodiments, the present invention relates to treating, reducing the incidence of, and/or preventing IDR in a patient undergoing PCI. IDR refers to any type of intervention following PCI in which blood flow through a vessel must be increased or re-established. Examples of IDR include, but are not limited to, an additional PCI or surgery.

Mortality

In certain embodiments, the present invention relates to reducing the incidence of and/or preventing mortality in a patient undergoing PCI. In some embodiments, mortality may be associated with other ischemic events. For instance, mortality may be caused by stent thrombosis, occlusion of a coronary artery, and/or myocardial infarction.

Methods of Treating, Reducing the Incidence of, and/or Preventing an Ischemic Event An aspect of the present invention is methods of treating, reducing the incidence of, and/or preventing an ischemic event in a patient undergoing PCI, comprising administering to the patient a pharmaceutical composition comprising cangrelor.

PCI may comprise balloon angioplasty without implantation of a stent, or may also comprise the implantation of a stent. The stent may be a bare-metal stent, or a drug-eluting stent, as known in the art.

Timing, Duration, and Routes of Administration of the Pharmaceutical Composition A method of the present invention comprises administering the pharmaceutical composition before, during, and/or after PCI. The administration may continue for a short period of time, such as less than about an hour, or may be one or more hours. In some embodiments, the administration may continue for at least the duration of the PCI. In other embodiments, the administration may continue after the PCI has concluded. In certain embodiments, the administration may continue for at least about 2 hours or the duration of the PCI procedure, whichever is longer. In an additional embodiment, the administration may continue for about 4 hours or longer.

A method may comprise administering the pharmaceutical composition multiple times before, during, and/or after PCI. For example, administration of the pharmaceutical composition may be for a short period of time before the PCI, and then again once PCI has begun.

In certain embodiments, the method may comprise administering the pharmaceutical composition periodically after the PCI has concluded. For instance, the pharmaceutical composition may be administered once, twice, thrice or more times a day, once every two days, once every three days, etc., and for weeks, months, or even years, after the PCI, particularly if the PCI involved stent implantation.

In additional embodiments, the method may comprise administering the pharmaceutical composition once the ischemic event is recognized or diagnosed, or at the onset of symptoms of the ischemic event. For example, the pharmaceutical composition may be administered if symptoms of a myocardial infarction are observed. The pharmaceutical composition may be administered within a short period of time from the onset of symptoms of the ischemic event. The short period of time may range from about one or two minutes to about one or two hours.

In some embodiments, the method may comprise administering the pharmaceutical composition as a prophylaxis against an ischemic event, such as myocardial infarction. Patients appropriate for such prevention include any patient suspected of having early symptoms of the ischemic event or other disease, or a condition that could lead to the ischemic event against which the pharmaceutical compositions of the invention would be effective. The pharmaceutical composition may be administered to the patient within a short period of time of when early or initial symptoms of the ischemic event are detected.

Methods of the present invention may comprise administering the pharmaceutical composition concurrently or sequentially with at least one additional therapeutic agent. The additional therapeutic agent may be a P2Y$_{12}$ receptor inhibitor, such as clopidogrel, ticagrelor, or prasugrel, or the additional therapeutic agent may be a glycoprotein IIb/IIIa inhibitor. Alternatively, the additional therapeutic agent may be aspirin. In some embodiments, the additional therapeutic agent may be administered after the administration of cangrelor, either immediately after or following a short period of time. For example, when cangrelor is administered as a bolus followed by infusion, the additional therapeutic agent, such as clopidogrel, may be administered after the infusion of cangrelor is complete. In certain embodiments, the additional therapeutic agent may be administered concurrently with cangrelor in the same pharmaceutical composition, or in separate pharmaceutical compositions.

In certain embodiments, the at least one additional therapeutic agent may comprise bivalirudin. Bivalirudin is a potent, reversible inhibitor of the serine protease thrombin. Thrombin is critical in the thrombotic process, cleaving fibrinogen into fibrin monomers and converting Factor XIII to Factor XIIIa, thereby allowing fibrin to develop into a covalently cross-linked framework which leads to clot formation. The chemical structure of bivalirudin is shown in Formula II.

Formula II

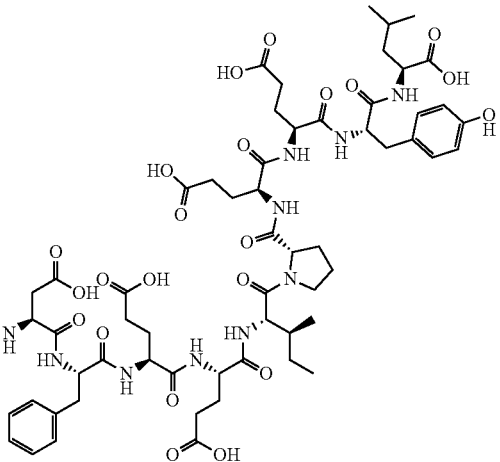

In each of the embodiments of the present invention, the term "bivalirudin" encompasses the compound of Formula II as well as pharmaceutically acceptable salts thereof. Salts of bivalirudin, processes for the production of bivalirudin, and pharmaceutical compositions comprising bivalirudin, are well known in the art and set forth, for example, in U.S. Pat. No. 5,196,404, which is incorporated herein in its entirety by reference.

The routes of administration of the methods of the present invention include, for example, oral, sublingual, intranasal, intraocular, rectal, transdermal, mucosal, topical or parenteral administration. Parenteral modes of administration include without limitation, intradermal, subcutaneous (s.c., s.q., sub-Q, Hypo), intramuscular (i.m.), intravenous (i.v.), intraperitoneal (i.p.), intra-arterial, intramedulary, intracardiac, intra-articular (joint), intrasynovial (joint fluid area), intracranial, intraspinal, and intrathecal (spinal fluids). Any known device useful for parenteral injection or infusion of drug formulations can be used in the methods of the present invention. In noted aspects and embodiments of the present invention, administration is via parenteral administration, preferably intravenous administration, or oral administration.

When administered intravenously, the pharmaceutical composition comprising cangrelor may be administered as a bolus, as a continuous infusion, or as a bolus followed by a continuous infusion. For example, the pharmaceutical composition may be administered prior to PCI as a bolus, and may be administered during PCI as a continuous infusion. In certain embodiments wherein an additional therapeutic agent is administered, the additional therapeutic agent may be administered as a bolus, as a continuous infusion, or as a bolus followed by a continuous infusion.

Doses of cangrelor in the pharmaceutical compositions administered in the methods of the present invention may vary depending upon the stated goals of the methods (treating, reducing the incidence of, and/or preventing), the physical characteristics of the patient, the significance of the ischemic event, existence of related or unrelated medical conditions, the composition of the formulation and the means used to administer the drug to the patient. The dose for a given patient will generally be set by the judgment of the attending physician.

When administered as a bolus, a dose of about 5 to about 100 µg/kg cangrelor, such as between about 20 and about 40 µg/kg cangrelor, or about 30 µg/kg cangrelor, is administered. When administered as a continuous infusion, cangrelor may be administered at about 0.1 to about 30 µg/kg/min, for example, between about 1 and about 10 µg/kg/min, or about 4 µg/kg/min. One of ordinary skill in the art will understand that the dose may differ in the periods before PCI, during PCI and after PCI.

In certain embodiments, the method of the present invention comprises administering a bolus of about 30 µg/kg cangrelor, followed by administering an infusion of about 4 µg/kg/min cangrelor.

When the pharmaceutical composition is administered orally, a dose of between about 0.5 to about 100 mg/kg cangrelor or about 5 to about 30 mg/kg cangrelor is administered per day. Oral administration may occur once a day or multiple times per day.

In certain embodiments of the present invention, an additional therapeutic agent is administered in addition to the pharmaceutical composition comprising cangrelor. When the additional therapeutic agent comprises clopidogrel, it may be administered orally with a dose of clopidogrel from about 75 mg to about 600 mg.

When the additional therapeutic agent comprises bivalirudin, it may be administered intravenously as a bolus and/or a continuous infusion. When administered as a bolus, a dose of about 0.05 to about 50 mg/kg bivalirudin, such as between about 0.1 and about 10 mg/kg bivalirudin, or about 0.75 mg/kg bivalirudin, may be administered. When administered as a continuous infusion, bivalirudin may be administered at about 0.1 to about 30 mg/kg/hr, for example, between about 0.5 and about 10 mg/kg/hr, or about 1.75 mg/kg/hr. One of ordinary skill in the art will understand that the dose may differ in the periods before PCI, during PCI and after PCI.

Patients

As used herein, a "patient" upon which the methods of the present invention may be practiced refers to an animal, such as a mammalian or an avian species, including a human, a non-human primate, a horse, a cow, a sheep, a goat, a dog, and a cat. Such patients may have an ischemic event, such as stent thrombosis, myocardial infarction, IDR, or mortality.

In view of the fact that the patients upon which some of the methods of the present invention are being practiced have underlying health conditions that require PCI, one of ordinary skill in the art will understand that the patients may have various additional physical characteristics related to such underlying health conditions. For example, in each of the embodiments of the present invention, the patient may have a condition selected from the group consisting of STEMI, NSTEMI, stable angina, unstable angina, and acute coronary syndrome. The patient may be of any age, gender, or weight. The patient may have received different therapeutic agents, such as a periprocedural glycoprotein IIb/IIIa inhibitor, periprocedural unfractionated heparin (UFH), periprocedural low-molecular-weight heparin (LMWH), periprocedural bivalirudin, or periprocedural clopidogrel.

To further characterize the patients to which the methods of the present invention may be applied, it is noted that the patient may have suffered a stroke, or may have diabetes mellitus, hypertension, hyperlipidemia, a myocardial infarction, or may have a family history of coronary artery disease (CAD). The patient may have undergone percutaneous transluminal coronary angioplasty (PTCA), PCI, or coronary artery bypass graft (CABG). The patient may have congestive heart failure, peripheral arterial disease (PAD), or stent thrombosis in more than one artery or vein. Further, the patient may be on periprocedural medications such as clopidogrel, bivalirudin, unfractionated heparin, low-molecular-weight heparin, fondaparinux, or aspirin.

Results of the Methods

Each of the methods recited in the present invention may include the additional step of measuring the effectiveness of the administration of the pharmaceutical composition comprising cangrelor, including the timing, duration, and route of administration of the pharmaceutical composition. The measurement may include the effectiveness of the administration of any additional therapeutic agent. In one example, this additional step may be performed about 0.5 to about 24 hours after administration is complete. Characteristics that are representative of effectiveness include, for example, an increase in luminal diameter within a stent, a decrease in the size of the stent thrombus, and a decreased incidence of myocardial infarction.

Pharmaceutical Compositions Useful for Treating, Reducing the Incidence of, and/or Preventing Ischemic Events An aspect of the present invention is directed to a pharmaceutical composition useful for treating, reducing the incidence of, and/or preventing an ischemic event in a patient undergoing PCI. The pharmaceutical composition comprises cangrelor, and may further comprise one or more pharmaceutically acceptable excipients. In addition, the pharmaceutical composition may further comprise an additional therapeutic agent such as bivalirudin. The pharmaceutical composition may be administered according to any of the methods of the present invention described above.

Pharmaceutically Acceptable Excipients

These pharmaceutical compositions may comprise one or more pharmaceutically acceptable excipients including, but not limited to, carriers, diluents, stabilizing agents, solubilizing agents, surfactants, buffers, antioxidants, preservatives, tonicity agents, bulking agents, lubricating agents, emulsifiers, suspending or viscosity agents, fillers, disintegrating agents, binding agents, wetting agents, lubricating agents, antibacterials, chelating agents, sweeteners, perfuming agents, flavouring agents, coloring agents, administration aids, and combinations thereof. Particular excipients include, but are not limited to, cornstarch or gelatin, lactose, sucrose, dextrose, microcrystalline cellulose, kaolin, mannitol, sorbitol, dicalcium phosphate, sodium chloride, alginic acid, croscarmellose sodium, sodium starch glycolate, glycerol, ethanol, propylene glycol, polysorbate 80 (Tween-80™), poly(ethylene)glycol 300 and 400 (PEG 300 and 400), PEGylated castor oil (e.g. Cremophor EL), poloxamer 407 and 188, cyclodextrin or cyclodextrin derivatives (including HPCD ((2-hydroxypropyl)-cyclodextrin) and (2-hydroxyethyl)-cyclodextrin), hydrophilic and hydrophobic carriers, and combinations thereof. Hydrophobic carriers include, for example, fat emulsions, lipids, PEGylated phospholipids, polymer matrices, biocompatible polymers, lipospheres, vesicles, particles, and liposomes. In certain embodiments, the pharmaceutical compositions may comprise polyols, such as sorbitol, lactose, sucrose, inositol or trehalose.

The pharmaceutical compositions of the present invention may be formulated for the route by which they are administered to the patients, which include solids, liquids, and suspensions. For example, if the pharmaceutical composition is formulated for IV administration, the pharmaceutical composition may comprise an intravenous fluid, which includes, but is not limited to, water-for-injection (WFI), physiological saline, 0.9% NaCl, phosphate buffered saline, 5% dextrose in water, and 0.002% polysorbate 80 in water or Ringer's™ solution. If the pharmaceutical composition is formulated for intramuscular administration, the pharmaceutical composition may comprise an intravenous fluid, which includes, but is not limited to, WFI, physiological saline, 0.9% NaCl, phosphate buffered saline, and 5% dextrose in water.

If the pharmaceutical composition is formulated for oral administration, the pharmaceutical composition may comprise excipients that include, but are not limited to diluents (e.g., sodium and calcium carbonate, sodium and calcium phosphate, and lactose), binding agents (e.g., acacia gum, starch, gelatin, sucrose, polyvinylpyrrolidone (Povidone), sorbitol, tragacanth, methylcellulose, sodium carboxymethylcellulose, hydroxypropyl methylcellulose, and ethylcellulose), fillers (e.g., calcium phosphate, glycine, lactose, maize-starch, sorbitol, or sucrose), wetting agents, lubricating agents (e.g., metallic stearates, stearic acid, polyethylene glycol, waxes, oils, silica and colloidal silica, silicon fluid or talc), disintegrating agents (e.g., potato starch, corn starch and alginic acid), flavouring agents (e.g. peppermint, oil of wintergreen, fruit flavoring, bubblegum, and the like), and coloring agents. Excipients may also include coatings such as glyceryl monostearate or glyceryl distearate, to delay absorption in the gastrointestinal tract. For oral use, the pharmaceutical composition may be made in the form of a tablet, capsule, suspension or liquid syrup or elixir, wafers and the like.

Preparing Pharmaceutical Compositions

The pharmaceutical compositions of the present invention may be prepared by admixing cangrelor with the one or more pharmaceutically acceptable excipients. Methods of admixing and devices useful for admixing are known in the art.

In certain embodiments, cangrelor and the one or more pharmaceutically acceptable excipients are dissolved and then admixed. The resulting mixture may be dried, such as through lyophilization, to form a solid pharmaceutical composition, or the resulting mixture may remain in solution form as a liquid pharmaceutical composition. In some embodiments, the solid pharmaceutical composition may be solubilized in an intravenous fluid before administration, for example, as a bolus or infusion.

In certain embodiments, the pharmaceutical composition is prepared by dissolving and admixing cangrelor, mannitol, sorbitol, and optionally sodium hydroxide, and then lyophilizing the mixture. Prior to administration, the lyophilized mixture is dissolved in an intravenous fluid such as WFI or physiological saline.

In some embodiments, the method may further comprise admixing one or more additional therapeutic agents, for example, bivalirudin, with cangrelor and optionally a pharmaceutically acceptable excipient.

Alternatively, bivalirudin may be prepared in a separate pharmaceutical composition from the pharmaceutical composition comprising cangrelor. The pharmaceutical composition comprising bivalirudin may be prepared by methods set forth in U.S. Pat. Nos. 7,582,727 and 7,598,343, which are incorporated herein in their entirety by reference.

The present invention will now be further described by way of the following non-limiting examples, which further illustrate the present invention; such examples are not intended, nor should they be interpreted, to limit the scope of the present invention.

EXAMPLES

Example 1—Intravenous Platelet Blockade with Cangrelor Versus Placebo During Percutaneous Coronary Intervention In this example, the efficacy of cangrelor versus placebo was examined when administered to patients during percutaneous coronary intervention (PCI).

Patients were enrolled at 218 sites in 18 countries from October 2006 to May 2009. Patients were randomized in a double-blind, placebo-controlled, double-dummy design to receive either (i) placebo bolus and infusion or (ii) cangrelor 30 μg/kg bolus and 4 μg/kg/min infusion for the duration of PCI, with a minimum infusion duration of 2 hours and a maximum of 4 hours. Patients in the placebo arm of the trial received 600 mg of clopidogrel at the end of the procedure, while patients in the cangrelor arm received 600 mg of clopidogrel after the end of the cangrelor infusion (FIG. 1).

The inclusion criteria for the trial were as follows: age≥18 years; diagnostic coronary angiography revealing atherosclerotic lesion(s) amenable to PCI with or without stent implantation; and evidence of either non-ST-segment elevation myocardial infarction or unstable angina. Stable angina was initially allowed at the beginning of the trial prior to a protocol amendment. The diagnosis of non-ST-segment elevation myocardial infarction required troponin I or T greater than the upper limit of normal within 24 hours of randomization (or if troponin results were unavailable at that time, creatine kinase-myocardial band isoenzyme [CK-MB] greater than the upper limit of normal). The diagnosis of unstable angina required ischemic chest discomfort occurring at rest and lasting ≥10 minutes within the 24 hours prior to randomization and dynamic electrocardiographic changes; age ≥65 years and/or diabetes mellitus were also required.

The exclusion criteria included the following: prior thienopyridine use in the past 7 days, planned staged PCI procedure where the second stage would occur ≤30 days after the first PCI, admission planned for <12 hours following PCI, ST-segment elevation myocardial infarction within 48 hours of randomization, known or suspected pregnancy, lactating females, increased bleeding risk (ischemic stroke within the last year or any previous hemorrhagic stroke), intracranial tumor, cerebral arteriovenous malformation, intracranial aneurysm, recent (<1 month) trauma or major surgery (including coronary artery bypass grafting), current warfarin use, active bleeding, known International Normalized Ratio >1.5, past or present bleeding disorder, platelet count <100,000/μL, severe hypertension (systolic blood pressure >180 mm Hg or diastolic blood pressure >110 mm Hg), fibrinolytic therapy or glycoprotein IIb/IIIa inhibitor use in the 12 hours preceding randomization.

The primary efficacy endpoint was the composite of mortality, myocardial infarction, or ischemia-driven revascularization at 48 hours. The primary analysis was performed on a modified intent-to-treat population. Confirmatory analyses were performed on an intent-to-treat population. Secondary endpoints included the individual rates of mortality, myocardial infarction, new Q-wave myocardial infarction, ischemia-driven revascularization, abrupt vessel closure, or stroke at 48 hours. Mortality at 30 days and 1 year was also recorded. The clinical events committee adjudicated myocardial infarction, Q-wave myocardial infarction, ischemia-driven revascularization, stent thromboses, and stroke (ischemic or hemorrhagic). The definition of stent thrombosis was similar to the Academic Research Consortium definition of definite stent thrombosis. After review of the prespecified analyses, two exploratory endpoints less reliant on periprocedural biomarker ascertainment were examined. The exploratory endpoints, which were composed of prespecified and adjudicated endpoints, were the composite of mortality, Q-wave myocardial infarction, or ischemia-driven revascularization and the composite of mortality, Q-wave myocardial infarction, or stent thrombosis. Bleeding and adverse events through 48 hours were compared.

Statistical Analyses—

All efficacy analyses were performed on the modified intent-to-treat population, defined as all randomized patients who received at least one dose of study drug and underwent the index PCI. All safety-related analyses were performed on the safety population, which included all patients who received at least one dose of assigned study drug. Patients in the safety analyses were assigned to a treatment arm based on treatment actually received, not as randomized. Intent-to-treat analyses are also presented for full disclosure of results. All statistical tests were two-tailed using a level of significance of 0.05. The primary endpoint comparison between the cangrelor and placebo arms was performed by calculating an odds ratio (OR) with accompanying 95% confidence intervals (CI) using logistic regression. Logistic regression was also used to analyze the majority of the remaining secondary endpoints. The trial had 85% power to detect a 25% reduction in the primary endpoint, assuming a 7.7% event rate in the placebo arm, with a projected sample size of 6400 patients.

Figure 2:
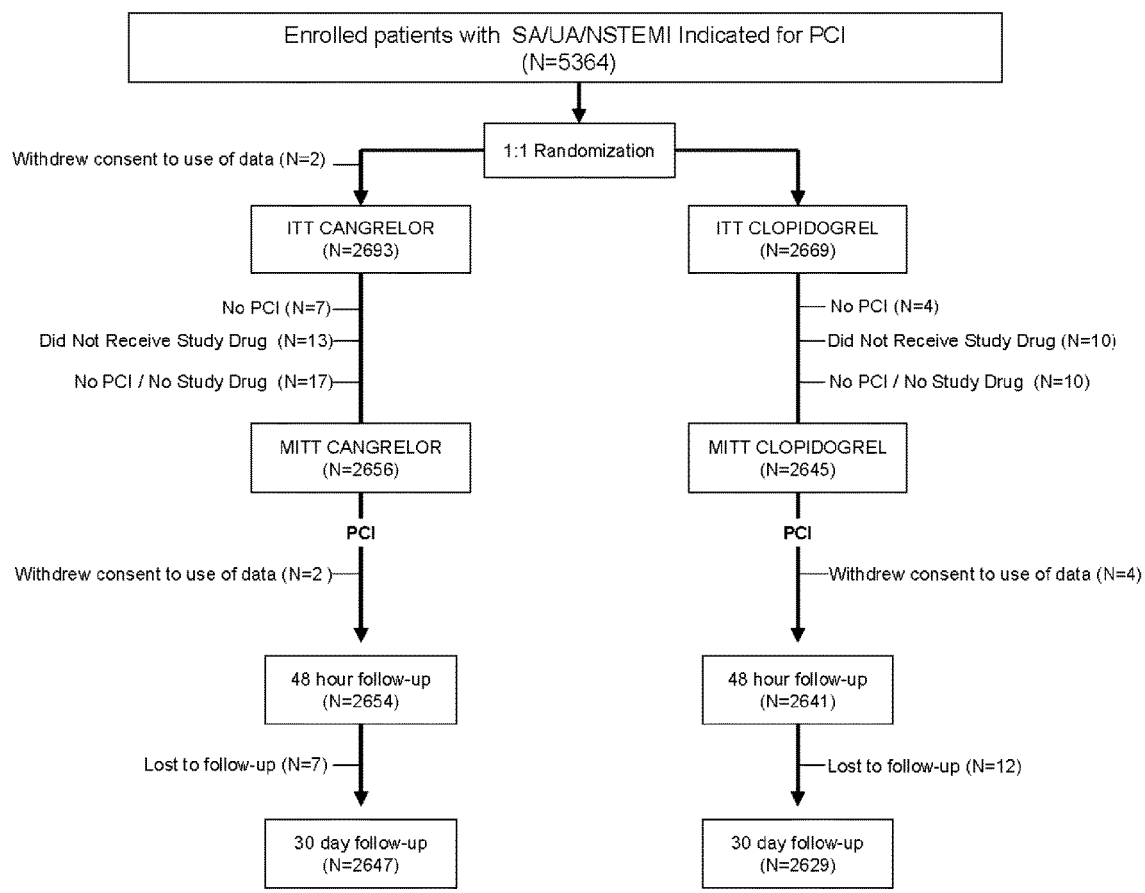
FIG. 2—diagram showing the primary modified intent-to-treat analysis population in the study described in Example 1.

A total of 5362 patients were included in the intent-to-treat population; of these, 5301 formed the primary modified intent-to-treat analysis population (FIG. 2). There were 61 patients who were not included because they did not receive study drug or undergo PCI. Baseline characteristics were well-matched in the two groups (Table 1).

TABLE 1

Baseline characteristics for ITT, MITT, and Safety populations

|  | ITT | | MITT |
|---|---|---|---|
|  | Cangrelor (N = 2693) | Clopidogrel (N = 2669) | Cangrelor (N = 2656) |
| Age, yrs | 63.0 (54.0, 71.0) | 63.0 (54.0, 71.0) | 63.0 (54.0, 71.0) |
| Sex, No. (%) | | | |
| Male | 1938 (72.0) | 1877 (70.3) | 1909 (71.9) |
| Female | 755 (28.0) | 792 (29.7) | 747 (28.1) |
| Race, No. (%) | | | |
| White | 2039 (76.0) | 2024 (76.0) | 2015 (76.1) |
| Asian | 482 (18.0) | 476 (17.9) | 475 (17.9) |
| Black | 80 (3.0) | 73 (2.7) | 75 (2.8) |
| Hispanic | 75 (2.8) | 85 (3.2) | 74 (2.8) |
| Other | 8 (0.3) | 5 (0.2) | 8 (0.3) |
| Weight, kg | 80.0 (70.0, 92.0) | 80.0 (70.0, 92.0) | 80.0 (70.0, 92.0) |
| Height, cm | 170.0 (163.0, 176.0) | 170.0 (163.0, 176.0) | 170.0 (163.0, 176.0) |
| Stable angina, No. (%) | 145 (5.4) | 142 (5.3) | 139 (5.2) |
| Unstable angina, No. (%) | 949 (35.2) | 918 (34.4) | 939 (35.4) |
| NSTEMI, No. (%) | 1599 (59.4) | 1609 (60.3) | 1578 (59.4) |
| Medical history, No. (%) | | | |
| Diabetes mellitus | 828 (30.8) | 868 (32.6) | 812 (30.6) |
| Current smoker | 850 (31.8) | 806 (30.4) | 842 (31.9) |
| Hypertension | 1994 (74.3) | 1979 (74.5) | 1972 (74.5) |
| Hyperlipidemia | 1342 (53.5) | 1347 (54.0) | 1324 (53.6) |
| Stroke/TIA | 162 (6.0) | 160 (6.0) | 159 (6.0) |
| Family history of CAD | 918 (36.4) | 901 (36.0) | 902 (36.2) |
| MI | 645 (24.1) | 683 (25.7) | 640 (24.2) |
| PTCA/PCI | 381 (14.2) | 411 (15.5) | 374 (14.1) |
| CABG | 203 (7.5) | 223 (8.4) | 199 (7.5) |
| Congestive HF | 210 (7.8) | 192 (7.2) | 206 (7.8) |
| PAD | 126 (4.8) | 143 (5.5) | 122 (4.7) |
| Periprocedural medications, No (%) | | | |
| Bivalirudin | 565 (21.0) | 561 (21.0) | 559 (21.0) |
| UFH | 1714 (63.7) | 1709 (64.1) | 1699 (64.0) |
| LMWH | 487 (18.1) | 501 (18.8) | 481 (18.1) |
| GP IIb/IIIa | 245 (9.1) | 247 (9.3) | 241 (9.1) |
| Study treatment | | | |
| Number of target vessels, No. (%) | | | |
| 1 | 2231 (83.7) | 2211 (83.3) | 2218 (83.6) |
| 2 | 414 (15.5) | 412 (15.5) | 414 (15.6) |
| 3 | 19 (0.7) | 29 (1.1) | 19 (0.7) |
| Drug-eluting stent, No. (%) | 1037 (38.9) | 1023 (38.6) | 1033 (38.9) |
| Non-drug-eluting stent, No. (%) | 1514 (56.8) | 1515 (57.1) | 1509 (56.9) |

TABLE 1-continued

Baseline characteristics for ITT, MITT, and Safety populations

| | | | |
|---|---|---|---|
| Angiographic complications (site reported) | | | |
| Threatened abrupt closure | 10 (0.4) | 9 (0.3) | 10 (0.4) |
| Unsuccessful procedure | 84 (3.1) | 97 (3.7) | 81 (3.1) |
| Abrupt vessel closure | 13 (0.5) | 16 (0.6) | 13 (0.5) |
| New thrombus or suspected thrombus | 14 (0.5) | 15 (0.6) | 14 (0.5) |
| Acute stent thrombosis | 1 (0.0) | 5 (0.2) | 1 (0.0) |
| Need for urgent CABG | 5 (0.2) | 4 (0.2) | 5 (0.2) |
| IV study drug administered, No. (%) | 2663 (98.9) | 2649 (99.3) | 2656 (100.0) |
| Bolus administered, No. (%) | 2663 (98.9) | 2649 (99.3) | 2656 (100.0) |
| Infusion administered, No. (%) | 2659 (98.7) | 2649 (99.3) | 2654 (99.9) |
| Duration of infusion, hrs | 2.1 (2.0, 2.3) | 2.1 (2.0, 2.3) | 2.1 (2.0, 2.3) |
| Oral study drug administered, No. (%) | 2630 (97.7) | 2626 (98.4) | 2629 (99.0) |

| | MITT | Safety | |
|---|---|---|---|
| | Clopidogrel (N = 2645) | Cangrelor (N = 2662) | Clopidogrel (N = 2650) |
| Age, yrs | 63.0 (54.0, 71.0) | 63.0 (54.0, 71.0) | 63.0 (54.0, 71.0) |
| Sex, No. (%) | | | |
| Male | 1863 (70.4) | 1915 (71.9) | 1866 (70.4) |
| Female | 782 (29.6) | 747 (28.1) | 784 (29.6) |
| Race, No. (%) | | | |
| White | 2006 (76.0) | 2017 (76.0) | 2009 (76.0) |
| Asian | 473 (17.9) | 477 (18.0) | 474 (17.9) |
| Black | 72 (2.7) | 76 (2.9) | 73 (2.8) |
| Hispanic | 84 (3.2) | 75 (2.8) | 84 (3.2) |
| Other | 5 (0.2) | 8 (0.3) | 5 (0.2) |
| Weight, kg | 80.0 (70.0, 92.0) | 80.0 (70.0, 92.0) | 80.0 (70.0, 92.0) |
| Height, cm | 170.0 (163.0, 176.0) | 170.0 (163.0, 176.0) | 170.0 (163.0, 176.0) |
| Stable angina, No. (%) | 140 (5.3) | 138 (5.2) | 141 (5.3) |
| Unstable angina, No. (%) | 909 (34.4) | 940 (35.3) | 911 (34.4) |
| NSTEMI, No. (%) | 1596 (60.3) | 1584 (59.5) | 1598 (60.3) |
| Medical history, No. (%) | | | |
| Diabetes mellitus | 862 (32.6) | 815 (30.6) | 862 (32.6) |
| Current smoker | 799 (30.4) | 845 (31.9) | 799 (30.3) |
| Hypertension | 1962 (74.5) | 1974 (74.4) | 1966 (74.5) |
| Hyperlipidemia | 1332 (53.9) | 1325 (53.5) | 1335 (53.9) |
| Stroke/TIA | 158 (6.0) | 160 (6.0) | 158 (6.0) |
| Family history of CAD | 890 (35.9) | 907 (36.4) | 891 (35.9) |
| MI | 679 (25.8) | 641 (24.2) | 680 (25.7) |
| PTCA/PCI | 409 (15.5) | 377 (14.2) | 409 (15.5) |
| CABG | 221 (8.4) | 200 (7.5) | 221 (8.3) |
| Congestive HF | 191 (7.2) | 208 (7.8) | 191 (7.2) |
| PAD | 142 (5.5) | 124 (4.8) | 142 (5.5) |
| Periprocedural medications, No (%) | | | |
| Bivalirudin | 555 (21.0) | 561 (21.1) | 556 (21.0) |
| UFH | 1695 (64.1) | 1701 (63.9) | 1699 (64.1) |
| LMWH | 497 (18.8) | 484 (18.2) | 497 (18.8) |
| GP IIb/IIIa | 244 (9.2) | 242 (9.1) | 244 (9.2) |
| Study treatment | | | |
| Number of target vessels, No. (%) | | | |
| 1 | 2201 (83.3) | 2217 (83.6) | 2202 (83.3) |
| 2 | 412 (15.6) | 414 (15.6) | 412 (15.6) |
| 3 | 29 (1.1) | 19 (0.7) | 29 (1.1) |
| Drug-eluting stent, No. (%) | 1021 (38.6) | 1032 (38.9) | 1022 (38.7) |
| Non-drug-eluting stent, No. (%) | 1510 (57.1) | 1509 (56.9) | 1510 (57.1) |
| Angiographic complications (site reported) | | | |
| Threatened abrupt closure | 9 (0.3) | 10 (0.4) | 9 (0.3) |
| Unsuccessful procedure | 95 (3.6) | 81 (3.1) | 95 (3.6) |
| Abrupt vessel closure | 16 (0.6) | 13 (0.5) | 16 (0.6) |
| New thrombus or suspected thrombus | 15 (0.6) | 14 (0.5) | 15 (0.6) |
| Acute stent thrombosis | 5 (0.2) | 1 (0.0) | 5 (0.2) |
| Need for urgent CABG | 3 (0.1) | 5 (0.2) | 3 (0.1) |
| IV study drug administered, No. (%) | 2645 (100.0) | 2662 (100.0) | 2650 (100.0) |
| Bolus administered, No. (%) | 2645 (100.0) | 2662 (100.0) | 2650 (100.0) |
| Infusion administered, No. (%) | 2645 (100.0) | 2658 (99.8) | 2650 (100.0) |

TABLE 1-continued

| Baseline characteristics for ITT, MITT, and Safety populations | | | |
|---|---|---|---|
| Duration of infusion, hrs | 2.1 (2.0, 2.3) | 2.1 (2.0, 2.3) | 2.1 (2.0, 2.3) |
| Oral study drug administered, No. (%) | 2625 (99.2) | 2629 (98.8) | 2627 (99.1) |

Variables are presented as median (25th, 75th) unless otherwise indicated.
CABG denotes coronary artery bypass grafting;
CAD, coronary artery disease;
GP, glycoprotein;
HF, heart failure;
ITT, intent to treat;
IV, intravenous;
LMWH, low molecular weight heparin;
MI, myocardial infarction;
MITT, modified intent to treat;
NSTEMI, non-ST-segment elevation myocardial infarction;
PAD, peripheral artery disease;
PCI, percutaneous coronary intervention;
PTCA, percutaneous transluminal coronary angioplasty;
TIA, transient ischemic attack;
UFH, unfractionated heparin.

Figure 3A:
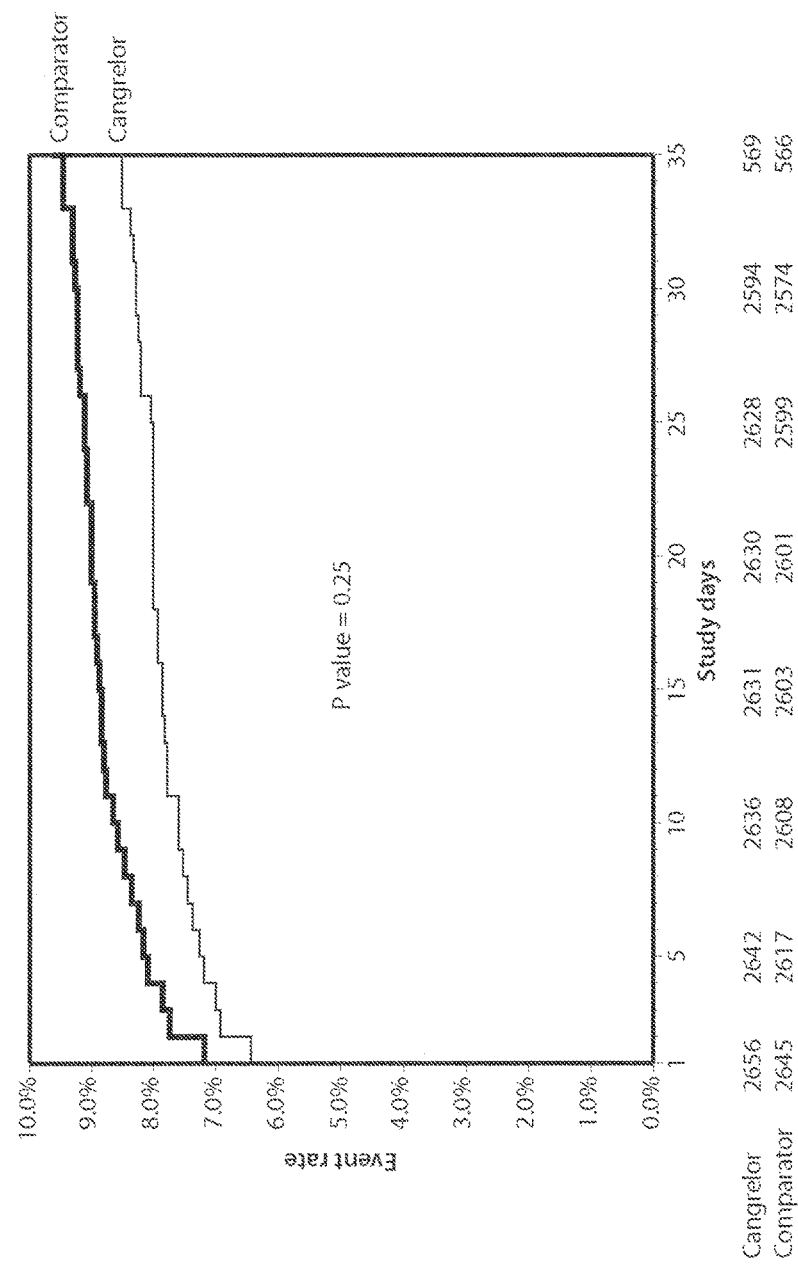
FIGS. 3A, 3B and 3C—landmark analysis of Kaplan-Meier curves for the primary efficacy endpoint (FIG. 3A), stent thrombosis (FIG. 3B), and mortality at 48 hours and 30 days (FIG. 3C) in the study described in Example 1.

The majority of patients were enrolled with non-ST-segment elevation myocardial infarction (59.8%). During PCI, unfractionated heparin was the most frequently used antithrombin (63.9%) and glycoprotein IIb/IIIa inhibitors were used sparingly (9.2%). Drug-eluting stents were used less often than bare metal stents (38.7% vs 56.9%). The time from hospital admission to PCI was short (median of 7.9 hours [3.3, 24.1]). The primary endpoint occurred in 7.0% of patients receiving cangrelor and 8.0% of patients receiving placebo (OR 0.87, 95% CI 0.71-1.07; P=0.17) (Table 2, FIG. 3A).

TABLE 2

48-hour endpoints for MITT, ITT, and Safety Populations

| | MITT | | | |
|---|---|---|---|---|
| | Cangrelor (N = 2656) | Clopidogrel (N = 2645) | OR (95% CI) | P Value |
| Adjudicated endpoints | | | | |
| Mortality/MI/IDR (primary endpoint) | 185 (7.0) | 210 (8.0) | 0.867 (0.706, 1.065) | 0.1746 |
| MI | 177 (6.7) | 191 (7.2) | 0.917 (0.742, 1.133) | 0.4207 |
| IDR | 19 (0.7) | 24 (0.9) | 0.786 (0.430, 1.439) | 0.4354 |
| All-cause mortality | 6 (0.2) | 18 (0.7) | 0.330 (0.131, 0.833) | 0.0190 |
| Stroke | 7 (0.3) | 5 (0.2) | 1.394 (0.442, 4.398) | 0.5708 |
| Stent thrombosis | 5 (0.2) | 16 (0.6) | 0.310 (0.113, 0.847) | 0.0223 |
| Q-wave MI | 4 (0.2) | 8 (0.3) | 0.497 (0.149, 1.652) | 0.2538 |
| Exploratory endpoints | | | | |
| Mortality/Q-wave MI/IDR | 23 (0.9) | 41 (1.6) | 0.554 (0.332, 0.926) | 0.0243 |
| Mortality/Q-wave MI/Stent thrombosis | 13 (0.5) | 34 (1.3) | 0.377 (0.199, 0.717) | 0.0029 |

| | ITT | | | |
|---|---|---|---|---|
| | Cangrelor (N = 2693) | Clopidogrel (N = 2669) | OR (95% CI) | P Value |
| Adjudicated endpoints | | | | |
| Mortality/MI/IDR | 187 (6.9) | 213 (8.0) | 0.859 (0.701, 1.054) | 0.1456 |
| MI | 177 (6.6) | 192 (7.2) | 0.906 (0.734, 1.120) | 0.3632 |
| IDR | 19 (0.7) | 26 (1.0) | 0.721 (0.398, 1.307) | 0.2814 |
| All-cause mortality | 8 (0.3) | 19 (0.7) | 0.415 (0.181, 0.950) | 0.0374 |
| Stroke | 7 (0.3) | 6 (0.2) | 1.155 (0.388, 3.442) | 0.7954 |
| Stent thrombosis | 5 (0.2) | 16 (0.6) | 0.308 (0.113, 0.847) | 0.0218 |
| Q-wave MI | 4 (0.1) | 9 (0.3) | 0.439 (0.135, 1.428) | 0.1713 |
| Exploratory endpoints | | | | |
| Mortality/Q-wave MI/IDR | 25 (0.9) | 44 (1.7) | 0.558 (0.341, 0.915) | 0.0207 |
| Mortality/Q-wave MI/Stent thrombosis | 15 (0.6) | 36 (1.4) | 0.409 (0.224, 0.749) | 0.0038 |

TABLE 2-continued 48-hour endpoints for MITT, ITT, and Safety Populations

| | Safety | | | |
|---|---|---|---|---|
| | Cangrelor (N = 2662) | Clopidogrel (N = 2650) | OR (95% CI) | P Value |
| Adjudicated endpoints | | | | |
| Mortality/MI/IDR | 185 (7.0) | 212 (8.0) | 0.858 (0.699, 1.053) | 0.1436 |
| MI | 176 (6.6) | 193 (7.3) | 0.901 (0.729, 1.113) | 0.3322 |
| IDR | 19 (0.7) | 25 (0.9) | 0.754 (0.414, 1.373) | 0.3561 |
| All-cause mortality | 7 (0.3) | 18 (0.7) | 0.385 (0.161, 0.924) | 0.0326 |
| Stroke | 7 (0.3) | 5 (0.2) | 1.394 (0.442, 4.396) | 0.5712 |
| Stent thrombosis | 5 (0.2) | 16 (0.6) | 0.310 (0.113, 0.846) | 0.0223 |
| Q-wave MI | 4 (0.2) | 9 (0.3) | 0.441 (0.136, 1.435) | 0.1738 |
| Exploratory endpoints | | | | |
| Mortality/Q-wave MI/IDR | 24 (0.9) | 42 (1.6) | 0.564 (0.341, 0.935) | 0.0263 |
| Mortality/Q-wave MI/Stent thrombosis | 14 (0.5) | 35 (1.3) | 0.395 (0.212, 0.735) | 0.0034 |

Variables are presented as no.
(%) unless otherwise indicated.
CI denotes confidence interval;
IDR, ischemia-driven revascularization;
ITT, intent to treat;
MI, myocardial infarction;
MITT, modified intent to treat;
OR, odds ratio.

Figure 3B:
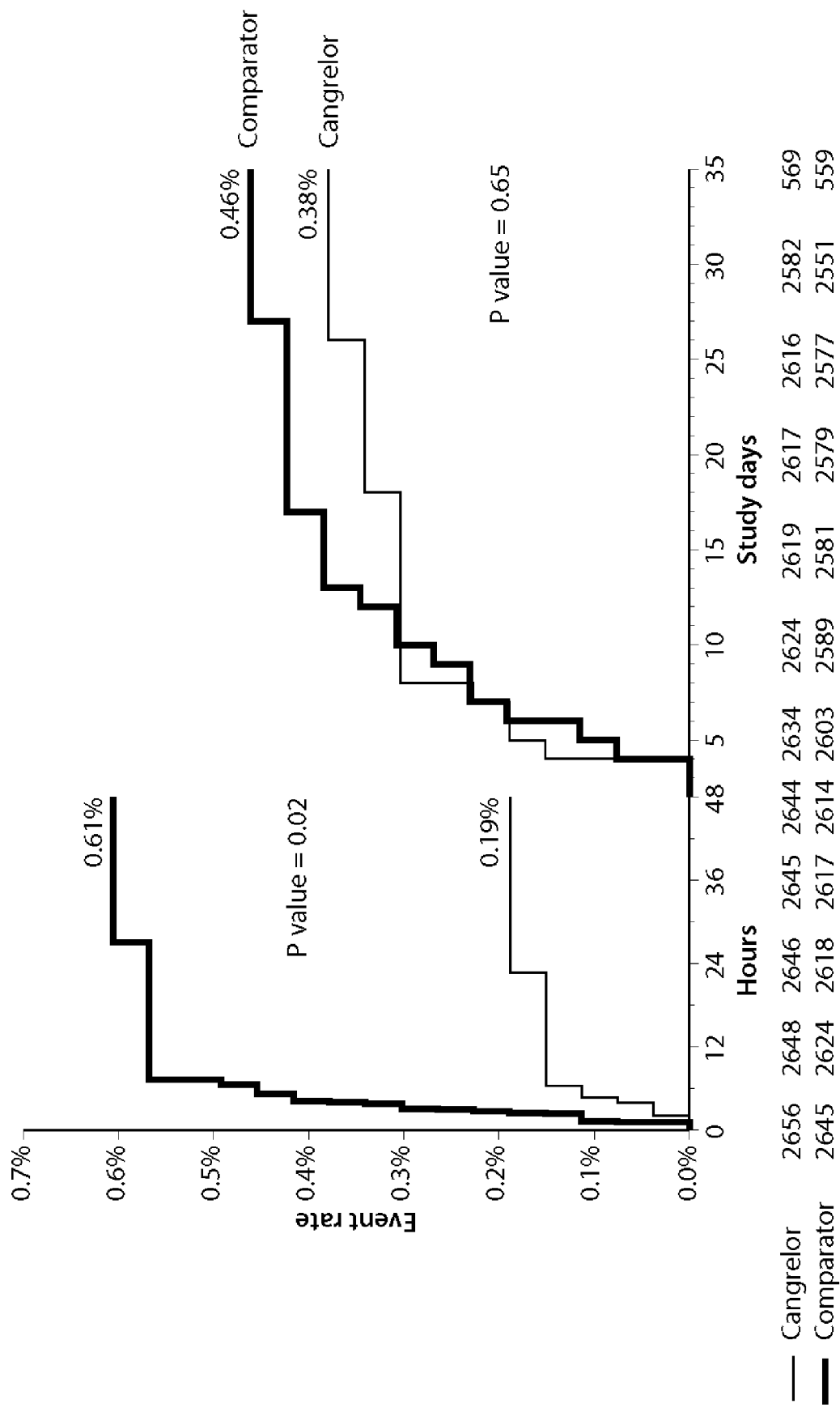
Figure 3C:
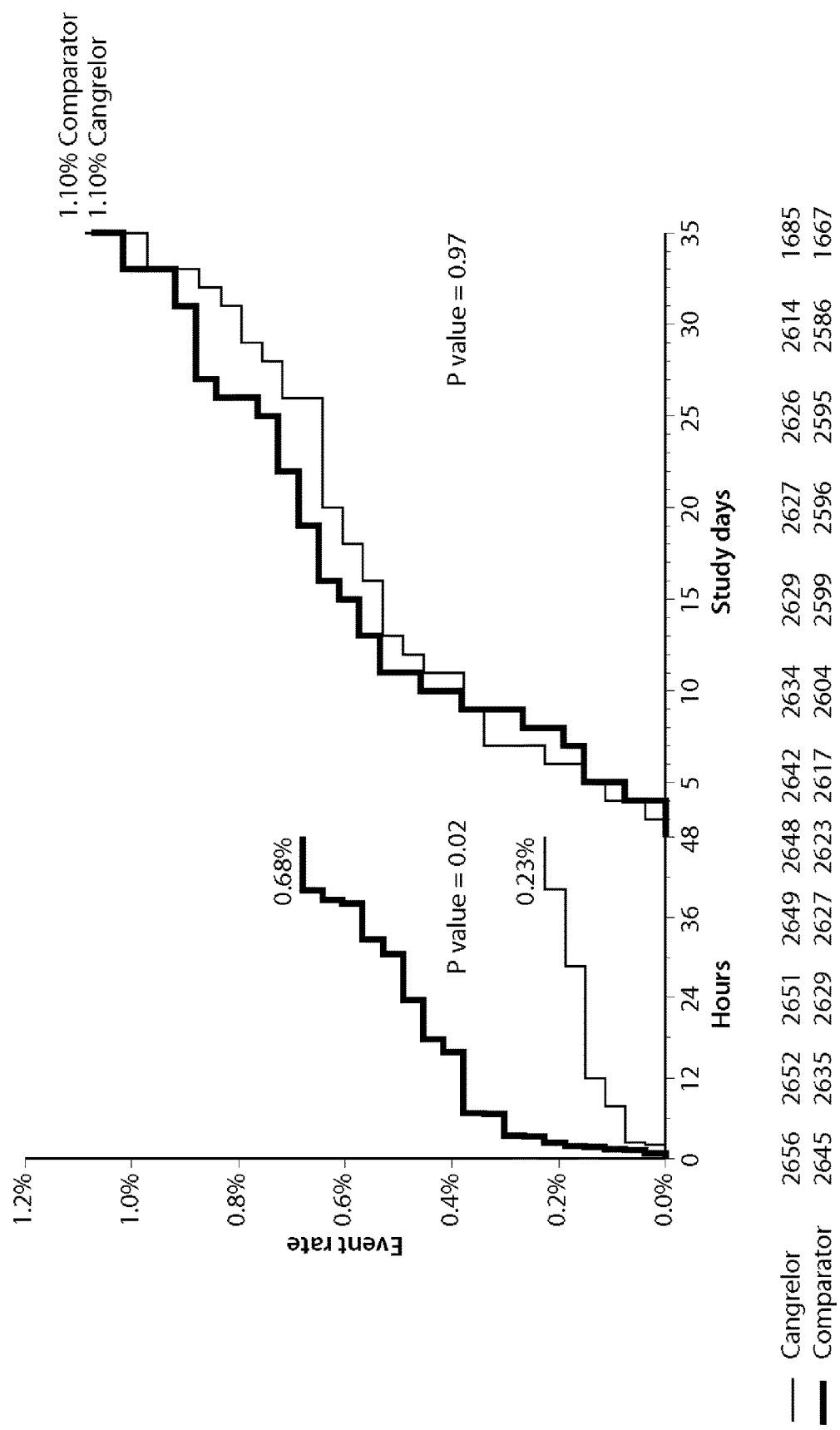

There was no significant difference in overall myocardial infarction, Q-wave myocardial infarction, or ischemia-driven revascularization (Table 2). Rates of stent thrombosis were significantly lower with cangrelor (0.2% vs 0.6% [OR 0.31, 95% CI 0.11-0.85; P=0.022]) (FIG. 3B). The rate of mortality at 48 hours was significantly lower in the cangrelor arm (0.2% vs 0.7% [OR 0.33, 95% CI 0.13-0.83; P=0.019]), though by 30 days, this difference was no longer significant (Table 3, FIG. 3C).

TABLE 3

30-day endpoints for ITT, MITT, and Safety Populations

| | ITT | | | |
|---|---|---|---|---|
| | Cangrelor (N = 2693) | Clopidogrel (N = 2669) | OR (95% CI) | P Value |
| Adjudicated endpoints | | | | |
| Mortality/MI/IDR | 230 (8.6) | 254 (9.6) | 0.885 (0.734, 1.067) | 0.1999 |
| MI | 190 (7.1) | 202 (7.6) | 0.924 (0.752, 1.135) | 0.4515 |
| IDR | 37 (1.4) | 49 (1.8) | 0.743 (0.483, 1.142) | 0.1752 |
| All-cause mortality | 36 (1.3) | 47 (1.8) | 0.754 (0.487, 1.167) | 0.2048 |
| Stent thrombosis | 15 (0.6) | 29 (1.1) | 0.508 (0.272, 0.950) | 0.0340 |
| Q-wave MI | 8 (0.3) | 15 (0.6) | 0.526 (0.222, 1.242) | 0.1425 |
| Exploratory endpoints | | | | |
| Mortality/Q-wave MI/IDR | 69 (2.6) | 94 (3.5) | 0.718 (0.524, 0.984) | 0.0396 |
| Mortality/Q-wave MI/Stent thrombosis | 51 (1.9) | 77 (2.9) | 0.648 (0.453, 0.927) | 0.0174 |
| | MITT | | | |
| | Cangrelor (N = 2656) | Clopidogrel (N = 2645) | OR (95% CI) | P Value |
| Adjudicated endpoints | | | | |
| Mortality/MI/IDR | 226 (8.5) | 249 (9.5) | 0.892 (0.739, 1.078) | 0.2365 |
| MI | 189 (7.1) | 201 (7.6) | 0.929 (0.756, 1.142) | 0.4831 |
| IDR | 37 (1.4) | 46 (1.7) | 0.796 (0.515, 1.231) | 0.3054 |
| All-cause mortality | 33 (1.2) | 45 (1.7) | 0.725 (0.461, 1.140) | 0.1635 |
| Stent thrombosis | 15 (0.6) | 28 (1.1) | 0.529 (0.282, 0.993) | 0.0477 |
| Q-wave MI | 8 (0.3) | 14 (0.5) | 0.566 (0.237, 1.352) | 0.2003 |
| Exploratory endpoints | | | | |
| Mortality/Q-wave MI/IDR | 66 (2.5) | 89 (3.4) | 0.730 (0.528, 1.008) | 0.0560 |
| Mortality/Q-wave MI/Stent thrombosis | 48 (1.8) | 73 (2.8) | 0.647 (0.447, 0.935) | 0.0203 |

TABLE 3-continued 30-day endpoints for ITT, MITT, and Safety Populations

| | Safety | | | |
|---|---|---|---|---|
| | Cangrelor (N = 2662) | Clopidogrel (N = 2650) | OR (95% CI) | P Value |
| Adjudicated endpoints | | | | |
| Mortality/MI/IDR | 226 (8.5) | 251 (9.5) | 0.884 (0.732, 1.067) | 0.1999 |
| MI | 188 (7.1) | 203 (7.7) | 0.913 (0.743, 1.122) | 0.3887 |
| IDR | 37 (1.4) | 47 (1.8) | 0.779 (0.504, 1.202) | 0.2584 |
| All-cause mortality | 34 (1.3) | 45 (1.7) | 0.747 (0.477, 1.170) | 0.2024 |
| Stent thrombosis | 15 (0.6) | 28 (1.1) | 0.529 (0.282, 0.993) | 0.0475 |
| Q-wave MI | 8 (0.3) | 15 (0.6) | 0.528 (0.224, 1.248) | 0.1455 |
| Exploratory endpoints | | | | |
| Mortality/Q-wave MI/IDR | 67 (2.5) | 90 (3.4) | 0.732 (0.531, 1.010) | 0.0572 |
| Mortality/Q-wave MI/Stent thrombosis | 49 (1.8) | 74 (2.8) | 0.651 (0.452, 0.938) | 0.0212 |

Variables are presented as no.
(%) unless otherwise indicated.
CI denotes confidence interval;
IDR, ischemia-driven revascularization;
ITT, intent to treat;
MI, myocardial infarction;
MITT, modified intent to treat;
OR, odds ratio.

Somewhat counterintuitively, in the subgroup of 1659 patients enrolled without baseline troponin elevation, the primary efficacy endpoint was reduced with cangrelor from 7.2% to 4.6% (OR 0.62, 95% CI 0.41, 0.95; P=0.0266). Therefore, exploratory analyses were performed in the overall study population examining the following two clinical endpoints: mortality, Q-wave myocardial infarction, or stent thrombosis; and mortality, Q-wave myocardial infarction, or ischemia-driven revascularization. These endpoints were significantly reduced in favor of cangrelor.

The rates of Thrombolysis in Myocardial Infarction (TIMI) major or minor or Global Utilization of Streptokinase and Tissue Plasminogen Activator for Occluded Coronary Arteries (GUSTO) severe or moderate bleeding were not significantly different between the groups, though the rates of Acute Catheterization and Urgent Intervention Triage Strategy (ACUITY) major and minor bleeding and of GUSTO mild bleeding were significantly higher with cangrelor (Table 4).

TABLE 4

48-hour bleeding events for safety population

| | Cangrelor (N = 2662) | Placebo (N = 2650) | Odds Ratio (95% CI) | P Value |
|---|---|---|---|---|
| Bleeding Events | | | | |
| Access site bleeding requiring radiologic or surgical intervention | 8 (0.3) | 10 (0.4) | 0.796 (0.314, 2.019) | 0.6307 |
| Hematoma ≥5 cm at puncture site | 115 (4.3) | 71 (2.7) | 1.640 (1.214, 2.216) | 0.0013 |
| Intracranial hemorrhage | 2 (0.1) | 1 (0.0) | 1.992 (0.180, 21.978) | 0.5738 |
| Intraocular | 0 (0.0) | 0 (0.0) | | |
| Reoperation for bleeding | 1 (0.0) | 1 (0.0) | 0.995 (0.062, 15.924) | 0.9975 |
| Retroperitoneal | 2 (0.1) | 1 (0.0) | 1.992 (0.180, 21.978) | 0.5738 |
| Ecchymosis | 95 (3.6) | 57 (2.2) | 1.684 (1.207, 2.349) | 0.0022 |
| Epistaxis | 6 (0.2) | 12 (0.5) | 0.497 (0.186, 1.325) | 0.1622 |
| Hematoma <5 cm at puncture site | 150 (5.6) | 119 (4.5) | 1.270 (0.992, 1.626) | 0.0577 |
| Oozing at puncture site | 125 (4.7) | 91 (3.4) | 1.385 (1.052, 1.825) | 0.0204 |
| Thrombocytopenia | 2 (0.1) | 3 (0.1) | 0.663 (0.111, 3.973) | 0.6532 |
| Hemodynamic compromise | 7 (0.3) | 5 (0.2) | 1.395 (0.442, 4.400) | 0.5704 |
| Any blood transfusion | 26 (1.0) | 16 (0.6) | 1.624 (0.869, 3.034) | 0.1285 |
| Any platelet transfusion | 4 (0.2) | 2 (0.1) | 1.992 (0.365, 10.887) | 0.4263 |
| Any red blood cell transfusion | 25 (0.9) | 15 (0.6) | 1.665 (0.876, 3.166) | 0.1197 |
| Drop in hemoglobin and/or hematocrit | 33 (1.2) | 35 (1.3) | 0.938 (0.581, 1.514) | 0.7927 |
| Bleed scoring criteria | | | | |
| ACUITY criteria | | | | |
| Minor bleeding | 320 (12.0) | 246 (9.3) | 1.335 (1.120, 1.592) | 0.0013 |
| Major bleeding | 147 (5.5) | 93 (3.5) | 1.607 (1.232, 2.096) | 0.0005 |

TABLE 4-continued 48-hour bleeding events for safety population

|  | Cangrelor (N = 2662) | Placebo (N = 2650) | Odds Ratio (95% CI) | P Value |
|---|---|---|---|---|
| GUSTO criteria |  |  |  |  |
| Mild bleeding | 427 (16.0) | 310 (11.7) | 1.442 (1.232, 1.688) | <.0001 |
| Moderate bleeding | 20 (0.8) | 13 (0.5) | 1.536 (0.762, 3.093) | 0.2300 |
| Severe/life-threatening bleeding | 9 (0.3) | 6 (0.2) | 1.495 (0.531, 4.205) | 0.4462 |
| TIMI criteria |  |  |  |  |
| Minor bleeding | 22 (0.8) | 16 (0.6) | 1.372 (0.719, 2.618) | 0.3376 |
| Major bleeding | 4 (0.2) | 9 (0.3) | 0.442 (0.136, 1.436) | 0.1742 |

Variables are presented as no.
(%) unless otherwise indicated.
The bleeding options under each criterion are not mutually exclusive. For example, a patient may have a clinically significant bleed and a minor bleed based on the ACUITY criteria, if more than 1 bleed is present. Each patient was counted only once for each criteria level, regardless of the number of bleeds identified under each criterion. Bleeding listed here included CABG-related bleeding.

Figure 4:
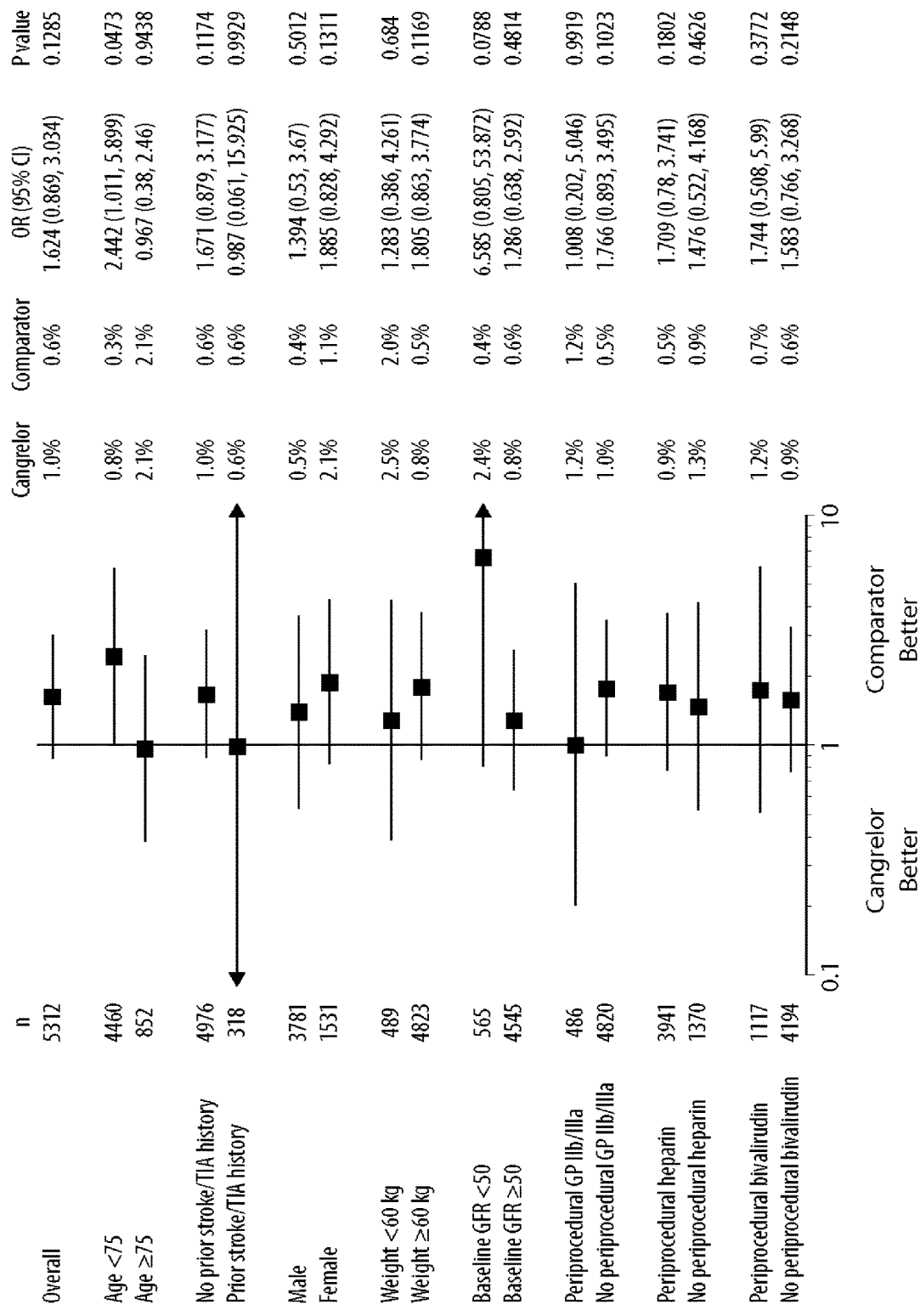
FIG. 4—diagram showing transfusion rates for all patients (including coronary artery bypass graft) in subgroups at high risk of bleeding in the study described in Example 1.

The difference in ACUITY major bleeding was due to an excess of groin hematomas, but not more serious forms of bleeding. The rates of red blood cell transfusion were not significantly different (0.9% with cangrelor vs 0.6% with placebo; P=0.12). Notably, patients at higher risk of bleeding, such as the elderly or those with prior stroke or transient ischemic attack, did not have a higher rate of transfusion with cangrelor (FIG. 4). There was no difference in the rate of arrhythmia (2.3% vs 2.4%; P=0.7664) and the incidence of dyspnea was higher with cangrelor (1.4% [37] vs 0.5% [14]; P=0.0019).

The results demonstrate that important prespecified endpoints, including stent thrombosis and mortality, were significantly reduced by cangrelor.

Example 2—Platelet Inhibition with Cangrelor in Patients with Acute Coronary Syndromes Undergoing Percutaneous Coronary Intervention In this example, the efficacy of cangrelor versus clopidogrel was examined when administered to patients before percutaneous coronary intervention (PCI).

Patients were eligible for enrollment if they had stable angina, unstable angina, or non-ST-segment elevation (NSTE) MI with obstructive coronary artery disease and were scheduled to undergo PCI. An additional 1000 patients with STEMI for whom primary PCI was planned were also eligible. A protocol amendment issued in May 2007 required that patients have definite features of an acute coronary syndrome (either STEMI undergoing planned primary PCI or a NSTE acute coronary syndrome with positive cardiac biomarkers or chest pain with dynamic electrocardiographic changes in patients >65 years or with diabetes). Patients could not have received fibrinolysis or glycoprotein IIb/IIIa inhibitors within the prior 12 hours or clopidogrel >75 mg/day in the prior 5 days.

Figure 5:
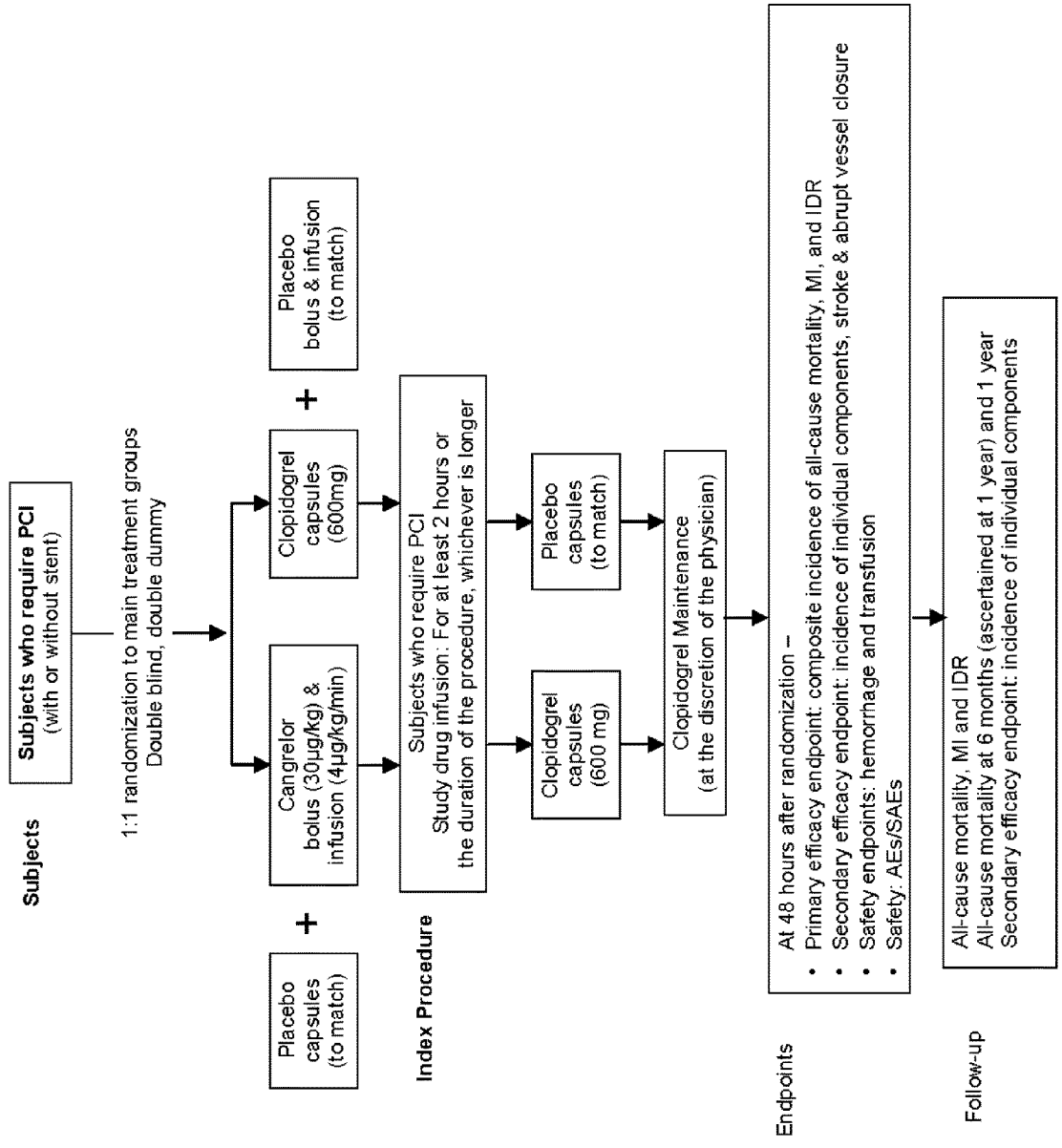
FIG. 5—diagram showing trial design for the study described in Example 2.

Patients were randomized in a 1:1 double-blind, double-dummy fashion using an IVRS system to either cangrelor or clopidogrel. All patients received a 30 μg/kg intravenous bolus of cangrelor or placebo followed by a 4 μg/kg/min intravenous infusion (FIG. 5). The infusion began within 30 minutes prior to PCI and continued for at least 2 hours or until the conclusion of the index procedure, whichever was longer. At the treating physician's discretion, the infusion could be continued for 4 hours. Patients received 600 mg encapsulated clopidogrel (four 150 mg capsules) or placebo at the time of infusion. To allow the transition from intravenous cangrelor to oral clopidogrel, patients ingested another four capsules (clopidogrel for cangrelor patients, placebo for clopidogrel patients) at the cessation of study drug infusion. The duration of daily clopidogrel following the procedure was left to the discretion of the treating physician, though additional clopidogrel beyond the prescribed study medication was not allowed until the day following the index procedure.

All patients received aspirin 75-325 mg per local site standards. Adjunctive anticoagulants (unfractionated heparin, low molecular weight heparin, bivalirudin, or fondaparinux) and the procedural use of glycoprotein IIb/IIIa inhibitors were determined by the treating physician.

The primary efficacy endpoint was the 48-hour composite of all-cause mortality, MI, or ischemia-driven revascularization. Prespecified secondary efficacy endpoints included the composite of mortality or MI at 48 hours and 30 days; the composite of mortality, MI, or ischemia-driven revascularization at 30 days; the components of the composite endpoints at 48 hours and 30 days; stroke at 48 hours; abrupt closure, threatened abrupt closure, need for urgent coronary artery bypass grafting, or unsuccessful procedure during the index PCI; acute (24 hours) and subacute (48 hours) stent thrombosis; and all-cause mortality at 6 months and 1 year.

Rates of MI and ischemia-driven revascularization up to 30 days following the index procedure were assessed. Ischemia-driven revascularization was defined as symptoms of myocardial ischemia leading to urgent (within 24 hours of the last episode of ischemia) revascularization, which must have occurred after the index procedure concluded (i.e., guidewire removal). New electrocardiographic changes, acute pulmonary edema, ventricular arrhythmias, or hemodynamic instability could also constitute evidence of ischemia.

MI was defined by a new Q wave (duration >0.03 seconds) in two contiguous electrocardiographic leads or elevations in creatine kinase (CK) and CK-MB, including a rise of CK-MB ≥3 times the local upper limit or normal and, when biomarkers were elevated prior to PCI, an additional 50% above baseline (Thygesen K. et al, *Circulation* 116: 2634-53 (2007)). One baseline troponin measurement was required for patients undergoing urgent PCI. Measurements of CK-MB were obtained at 2, 10, 17, and 24 hours post-PCI. Stent thrombosis was defined using Academic Research Consortium criteria (Cutlip D. E. et al., *Circulation* 115:2344-51 (2007)).

Bleeding was assessed up to 48 hours using clinical and laboratory definitions.

Multiple definitions of bleeding were used for full disclosure of bleeding risks associated with cangrelor: (1) The Global Utilization of Streptokinase and Tissue Plasminogen Activator for Occluded Coronary Arteries (GUSTO) criteria (The GUSTO Investigators. *N Engl J Med* 329:673-82 (1993); mild, moderate, or severe/life-threatening based on transfusion use and presence/absence of hemodynamic compromise); (2) Thrombolysis in Myocardial Infarction (TIMI) criteria (Chesebro J. H. et al., *Circulation* 76:142-54 (1987); minor or major bleeding based on clinical and laboratory findings); (3) Acute Catheterization and Urgent Intervention Triage Strategy (ACUITY) criteria (Stone G. W. et al., *N Engl J Med* 355:2203-16 (2006); using detailed clinical assessment, changes in hemoglobin, hematomas >5 cm, and need for blood transfusion). Investigators reported adverse and serious adverse events according to International Conference on Harmonization guidance (International Conference on Harmonization (ICH) Guidance Documents. U.S. Food and Drug Administration Web site. (Accessed on Oct. 8, 2009, at the FDA website beginning with "www." and ending with "fda.gov/RegulatoryInformation/Guidances/ucm122049.htm")).

An independent clinical events committee reviewed and adjudicated suspected MI, ischemia-driven revascularization, stent thrombosis, and stroke blinded to knowledge of the study medication (Mahaffey K. W. et al., *Am Heart J* 143:242-8 (2002)).

Determination of periprocedural MI can be challenging when most patients have elevated biomarkers and a single baseline sample. After the initial analyses were completed and reviewed, additional post-hoc composites were performed to better understand the potential effect of the drug on periprocedural outcomes less reliant on biomarkers (e.g., mortality, stent thrombosis, and Q-wave MI).

The sample size was based on the estimated composite incidence of all-cause mortality, MI, and ischemia-driven revascularization at 48 hours. Since there was no prior information about the use of cangrelor in the setting of STEMI and primary PCI and given the challenge of measuring re-infarction in the early hours of STEMI, the primary efficacy endpoint excluded these patients from the analysis, though they were included in analyses of safety. The composite event rate was estimated at 7% in the control clopidogrel arm. The trial was designed as a superiority trial to demonstrate a benefit of cangrelor over 600 mg clopidogrel. Assuming a 22% risk reduction, a sample size of 8000 patients would provide approximately 82% power with an alpha level of 0.05. The plan was to include up to 1000 patients with STEMI, raising the sample size to 9000 patients.

The primary efficacy analysis was to be determined in the modified intent-to-treat (mITT) population, defined as all randomized patients (excluding STEMI cohort) who received at least one dose of study drug and underwent the index PCI. The safety population consisted of all randomized patients who received any study drug. Patients in the safety analyses were assigned to a treatment arm based on treatment received, not as randomized. The ITT analysis with and without the STEMI cohort is reported.

All statistical tests were two-tailed using a level of significance of 0.05. The primary endpoint comparison between the cangrelor and placebo arms was performed by calculating an odds ratio (OR), with accompanying 95% confidence intervals (CI), using logistic regression. Logistic regression was used to analyze the majority of the remaining secondary endpoints. Continuous variables are summarized by medians and interquartile ranges. Categorical variables are summarized by frequencies and percentages. In the secondary efficacy analyses, there was no attempt to adjust the P values for the multiplicity issue. These analyses were considered exploratory and hypothesis-generating.

At the end of the study, 98% (n=8877) of the expected 9000 patients had been enrolled at 268 sites across 14 countries. For the 48-hour and 30-day endpoints, vital status follow-up was 99.7% and 98.6% complete, respectively.

Baseline demographics on the ITT population are shown in Table 5. Baseline demographics for the MITT and safety populations are shown in Tables 6 and 7.

TABLE 5

Baseline characteristics for ITT Population

| Baseline characteristics | ITT | | ITT Without STEMI |
| --- | --- | --- | --- |
| | Cangrelor (N = 4433) | Clopidogrel (N = 4444) | Cangrelor (N = 3946) |
| Age, yrs | 62.0 (54.0, 70.0) | 62.0 (54.0, 71.0) | 63.0 (55.0, 71.0) |
| Sex, No. (%) | | | |
| Male | 3275 (73.9) | 3209 (72.2) | 2891 (73.3) |
| Female | 1158 (26.1) | 1235 (27.8) | 1055 (26.7) |
| Race, No. (%) | | | |
| White | 3658 (82.6) | 3626 (81.7) | 3229 (81.9) |
| Asian | 311 (7.0) | 313 (7.1) | 294 (7.5) |
| Black | 215 (4.9) | 239 (5.4) | 190 (4.8) |
| Hispanic | 209 (4.7) | 218 (4.9) | 197 (5.0) |
| Other | 35 (0.8) | 42 (1.0) | 31 (0.8) |
| Weight, kg | 84.0 (73.0, 97.0) | 84.0 (73.0, 97.0) | 84.0 (73.0, 97.0) |
| Height, cm | 172.0 (165.0, 178.0) | 172.0 (165.0, 178.0) | 172.0 (165.0, 178.0) |
| Stable angina, No. (%) | 668 (15.1) | 665 (15.0) | 668 (16.9) |
| Unstable angina, No. (%) | 1097 (24.7) | 1088 (24.5) | 1097 (27.8) |
| Urgent NSTEMI, No. (%) | 639 (14.4) | 640 (14.4) | 639 (16.2) |
| NSTEMI, No. (%) | 1542 (34.8) | 1542 (34.7) | 1542 (39.1) |
| STEMI, No. (%) | 487 (11.0) | 509 (11.5) | 0 (0.0) |

TABLE 5-continued

Baseline characteristics for ITT Population

| Medical history, No. (%) | | | |
|---|---|---|---|
| Diabetes mellitus | 1350 (30.5) | 1352 (30.5) | 1248 (31.6) |
| Current smoker | 1247 (28.5) | 1283 (29.1) | 1035 (26.6) |
| Hypertension | 3181 (72.1) | 3139 (71.0) | 2900 (73.8) |
| Hyperlipidemia | 2825 (66.6) | 2777 (65.5) | 2590 (68.4) |
| Stroke/TIA | 223 (5.1) | 227 (5.1) | 208 (5.3) |
| Family history of CAD | 1843 (45.9) | 1873 (46.5) | 1656 (46.1) |
| MI | 1075 (24.6) | 1089 (24.8) | 1003 (25.9) |
| PTCA/PCI | 1266 (28.6) | 1261 (28.5) | 1193 (30.3) |
| CABG | 557 (12.6) | 552 (12.4) | 541 (13.7) |
| Congestive HF | 333 (7.6) | 338 (7.7) | 319 (8.2) |
| PAD | 323 (7.4) | 315 (7.2) | 294 (7.6) |
| Periprocedural medications, No. (%) | | | |
| Bivalirudin | 1313 (29.6) | 1337 (30.1) | 1244 (31.5) |
| UFH | 2437 (55.0) | 2452 (55.3) | 2154 (54.6) |
| LMWH | 368 (8.3) | 340 (7.7) | 322 (8.2) |
| GP IIb/IIIa | 1163 (26.3) | 1183 (26.7) | 909 (23.0) |
| Study treatment Number of target vessels, No. (%) | | | |
| 1 | 3836 (88.0) | 3796 (87.4) | 3406 (87.3) |
| 2 | 484 (11.1) | 509 (11.7) | 457 (11.7) |
| 3 | 38 (0.9) | 36 (0.8) | 38 (1.0) |
| Drug-eluting stent, No. (%) | 2581 (59.2) | 2560 (59.0) | 2422 (62.1) |
| Non-drug-eluting stent, No. (%) | 1640 (37.6) | 1635 (37.7) | 1367 (35.0) |
| Angiographic complications (site reported) | | | |
| Threatened abrupt closure | 13 (0.3) | 12 (0.3) | 9 (0.2) |
| Unsuccessful procedure | 90 (2.1) | 103 (2.4) | 81 (2.1) |
| Abrupt vessel closure | 24 (0.6) | 22 (0.5) | 20 (0.5) |
| New thrombus or suspected thrombus | 17 (0.4) | 23 (0.5) | 16 (0.4) |
| Acute stent thrombosis | 2 (0.0) | 5 (0.1) | 2 (0.1) |
| Need for urgent CABG | 10 (0.2) | 7 (0.2) | 8 (0.2) |
| IV study drug administered, No. (%) | 4367 (98.5) | 4355 (98.0) | 3904 (99.0) |
| Bolus administered, No. (%) | 4367 (98.5) | 4354 (98.0) | 3904 (99.0) |
| Infusion administered, No. (%) | 4364 (98.5) | 4353 (98.0) | 3901 (98.9) |
| Duration of infusion, hrs | 2.1 (2.0, 2.2) | 2.1 (2.0, 2.2) | 2.1 (2.0, 2.2) |
| Oral study drug administered, No. (%) | 4351 (98.2) | 4345 (97.8) | 3896 (98.8) |

| | ITT Without STEMI | ITT With STEMI | |
|---|---|---|---|
| Baseline characteristics | Clopidogrel (N = 3935) | Cangrelor (N = 487) | Clopidogrel (N = 509) |
| Age, yrs | 62.0 (54.0, 71.0) | 58.0 (51.0, 67.0) | 61.0 (52.0, 70.0) |
| Sex, No. (%) | | | |
| Male | 2831 (71.9) | 384 (78.9) | 378 (74.3) |
| Female | 1104 (28.1) | 103 (21.1) | 131 (25.7) |
| Race, No. (%) | | | |
| White | 3184 (81.0) | 429 (88.1) | 442 (87.0) |
| Asian | 300 (7.6) | 17 (3.5) | 13 (2.6) |
| Black | 208 (5.3) | 25 (5.1) | 31 (6.1) |
| Hispanic | 204 (5.2) | 12 (2.5) | 14 (2.8) |
| Other | 34 (0.9) | 4 (0.8) | 8 (1.6) |
| Weight, kg | 84.0 (73.0, 98.0) | 83 (72.0, 95.0) | 82.0 (72.0, 95.0) |
| Height, cm | 172.0 (165.0, 178.0) | 173.0 (167.6, 178.0) | 172.0 (165.0, 178.0) |
| Stable angina, No. (%) | 665 (16.9) | 0 (0.0) | 0 (0.0) |
| Unstable angina, No. (%) | 1088 (27.6) | 0 (0.0) | 0 (0.0) |
| Urgent NSTEMI, No. (%) | 640 (16.3) | 0 (0.0) | 0 (0.0) |
| NSTEMI, No. (%) | 1542 (39.2) | 0 (0.0) | 0 (0.0) |
| STEMI, No. (%) | 0 (0.0) | 487 (100.0) | 509 (100.0) |

TABLE 5-continued

Baseline characteristics for ITT Population

| Medical history, No. (%) | | | |
|---|---|---|---|
| Diabetes mellitus | 1263 (32.1) | 102 (20.9) | 89 (17.5) |
| Current smoker | 1076 (27.6) | 212 (43.7) | 207 (41.2) |
| Hypertension | 2839 (72.4) | 281 (58.1) | 300 (60.0) |
| Hyperlipidemia | 2536 (67.4) | 235 (51.5) | 241 (50.8) |
| Stroke/TIA | 205 (5.2) | 15 (3.1) | 22 (4.4) |
| Family history of CAD | 1686 (47.1) | 187 (43.7) | 187 (41.6) |
| MI | 1007 (26.0) | 72 (14.9) | 82 (16.2) |
| PTCA/PCI | 1198 (30.6) | 73 (15.0) | 63 (12.4) |
| CABG | 532 (13.5) | 16 (3.3) | 20 (3.9) |
| Congestive HF | 322 (8.3) | 14 (2.9) | 16 (3.2) |
| PAD | 290 (7.5) | 29 (6.0) | 25 (5.0) |
| Periprocedural medications, No. (%) | | | |
| Bivalirudin | 1250 (31.8) | 69 (14.2) | 87 (17.1) |
| UFH | 2155 (54.8) | 283 (58.2) | 297 (58.5) |
| LMWH | 298 (7.6) | 46 (9.5) | 42 (8.3) |
| GP IIb/IIIa | 927 (23.6) | 254 (52.3) | 256 (50.4) |
| Study treatment Number of target vessels, No. (%) | | | |
| 1 | 3360 (86.5) | 430 (94.1) | 436 (95.2) |
| 2 | 488 (12.6) | 27 (5.9) | 21 (4.6) |
| 3 | 35 (0.9) | 0 (0.0) | 1 (0.2) |
| Drug-eluting stent, No. (%) | 2383 (61.4) | 159 (34.8) | 177 (38.6) |
| Non-drug-eluting stent, No. (%) | 1380 (35.5) | 273 (59.7) | 255 (55.7) |
| Angiographic complications (site reported) | | | |
| Threatened abrupt closure | 10 (0.3) | 4 (0.9) | 2 (0.4) |
| Unsuccessful procedure | 92 (2.4) | 9 (2.0) | 11 (2.4) |
| Abrupt vessel closure | 19 (0.5) | 4 (0.9) | 3 (0.7) |
| New thrombus or suspected thrombus | 16 (0.4) | 1 (0.2) | 7 (1.5) |
| Acute stent thrombosis | 5 (0.1) | 0 (0.0) | 0 (0.0) |
| Need for urgent CABG | 7 (0.2) | 2 (0.4) | 0 (0.0) |
| IV study drug administered, No. (%) | 3883 (98.7) | 463 (95.1) | 472 (92.7) |
| Bolus administered, No. (%) | 3883 (98.7) | 463 (95.1) | 471 (92.5) |
| Infusion administered, No. (%) | 3882 (98.7) | 463 (95.1) | 471 (92.5) |
| Duration of infusion, hrs | 2.1 (2.0, 2.2) | 2.0 (2.0, 2.2) | 2.1 (2.0, 2.2) |
| Oral study drug administered, No. (%) | 3882 (98.7) | 455 (93.4) | 463 (91.0) |

Variables are presented as median (25th, 75th) unless otherwise indicated.
CABG denotes coronary artery bypass grafting;
CAD, coronary artery disease;
GP, glycoprotein;
HF, heart failure;
ITT, intent to treat;
IV, intravenous;
LMWH, low molecular weight heparin;
MI, myocardial infarction;
NSTEMI, non-ST-segment elevation myocardial infarction;
PAD, peripheral artery disease;
PCI, percutaneous coronary intervention;
PTCA, percutaneous transluminal coronary angioplasty;
STEMI, ST-segment elevation myocardial infarction;
TIA, transient ischemic attack;
UFH, unfractionated heparin.

TABLE 6

| | MITT | | MITT NSTEMI | |
|---|---|---|---|---|
| Baseline characteristics | Cangrelor (N = 4347) | Clopidogrel (N = 4320) | Cangrelor (N = 3897) | Clopidogrel (N = 3871) |
| Age, yrs | 62.0 (54.0, 70.0) | 62.0 (54.0, 71.0) | 63.0 (55.0, 70.0) | 62.0 (54.0, 71.0) |
| Sex, No. (%) | | | | |
| Male | 3212 (73.9) | 3124 (72.3) | 2854 (73.2) | 2786 (72.0) |
| Female | 1135 (26.1) | 1196 (27.7) | 1043 (26.8) | 1085 (28.0) |
| Race, No. (%) | | | | |
| White | 3589 (82.7) | 3516 (81.5) | 3193 (82.0) | 3127 (80.9) |
| Asian | 306 (7.0) | 312 (7.2) | 289 (7.4) | 299 (7.7) |
| Black | 208 (4.8) | 230 (5.3) | 185 (4.8) | 205 (5.3) |
| Hispanic | 205 (4.7) | 214 (5.0) | 194 (5.0) | 201 (5.2) |
| Other | 34 (0.8) | 42 (1.0) | 31 (0.8) | 34 (0.9) |
| Weight, kg | 84.0 (73.0, 97.0) | 84.0 (73.0, 97.0) | 84.0 (73.0, 97.0) | 84.0 (73.0, 97.0) |
| Height, cm | 172.0 (165.0, 178.0) | 172.0 (165.0, 178.0) | 172.0 (165.0, 178.0) | 172.0 (165.0, 178.0) |
| Stable angina, No. (%) | 659 (15.2) | 645 (14.9) | 659 (16.9) | 645 (16.7) |
| Unstable angina, No. (%) | 1088 (25.0) | 1071 (24.8) | 1088 (27.9) | 1071 (27.7) |
| Urgent NSTEMI, No. (%) | 627 (14.4) | 632 (14.6) | 627 (16.1) | 632 (16.3) |
| NSTEMI, No. (%) | 1523 (35.0) | 1523 (35.3) | 1523 (39.1) | 1523 (39.3) |
| STEMI, No. (%) | 450 (10.4) | 449 (10.4) | 0 (0.0) | 0 (0.0) |
| Medical history, No. (%) | | | | |
| Diabetes mellitus | 1327 (30.5) | 1313 (30.4) | 1233 (31.7) | 1238 (32.0) |
| Current smoker | 1229 (28.6) | 1245 (29.0) | 1025 (26.6) | 1057 (27.5) |
| Hypertension | 3122 (72.2) | 3045 (70.9) | 2865 (73.8) | 2788 (72.3) |
| Hyperlipidemia | 2771 (66.6) | 2705 (65.7) | 2555 (68.3) | 2491 (67.3) |
| Stroke/TIA | 220 (5.1) | 218 (5.1) | 206 (5.3) | 201 (5.2) |
| Family history of CAD | 1809 (45.9) | 1825 (46.6) | 1637 (46.1) | 1656 (47.1) |
| MI | 1059 (24.7) | 1054 (24.7) | 991 (25.9) | 983 (25.8) |
| PTCA/PCI | 1247 (28.8) | 1229 (28.6) | 1181 (30.4) | 1172 (30.4) |
| CABG | 546 (12.6) | 537 (12.4) | 533 (13.7) | 521 (13.5) |
| Congestive HF | 325 (7.5) | 326 (7.6) | 314 (8.1) | 311 (8.1) |
| PAD | 320 (7.5) | 304 (7.2) | 292 (7.6) | 282 (7.4) |
| Periprocedural medications, No. (%) | | | | |
| Bivalirudin | 1298 (29.9) | 1316 (30.5) | 1232 (31.6) | 1232 (31.8) |
| UFH | 2399 (55.2) | 2404 (55.7) | 2134 (54.8) | 2132 (55.1) |
| LMWH | 364 (8.4) | 334 (7.7) | 319 (8.2) | 297 (7.7) |
| GP IIb/IIIa | 1148 (26.4) | 1160 (26.9) | 903 (23.2) | 921 (23.8) |
| Study treatment | | | | |
| Number of target vessels, No. (%) | | | | |
| 1 | 3818 (88.0) | 3772 (87.4) | 3395 (87.3) | 3345 (86.5) |
| 2 | 482 (11.1) | 506 (11.7) | 455 (11.7) | 485 (12.5) |
| 3 | 38 (0.9) | 36 (0.8) | 38 (1.0) | 35 (0.9) |
| Drug-eluting stent, No. (%) | 2572 (59.3) | 2547 (59.0) | 2415 (62.1) | 2375 (61.4) |
| Non-drug-eluting stent, No. (%) | 1632 (37.6) | 1628 (37.7) | 1362 (35.0) | 1375 (35.6) |
| Angiographic complications (site reported) | | | | |
| Threatened abrupt closure | 13 (0.3) | 12 (0.3) | 9 (0.2) | 10 (0.3) |
| Unsuccessful procedure | 90 (2.1) | 103 (2.4) | 81 (2.1) | 92 (2.4) |
| Abrupt vessel closure | 24 (0.6) | 22 (0.5) | 20 (0.5) | 19 (0.5) |
| New thrombus or suspected thrombus | 17 (0.4) | 22 (0.5) | 16 (0.4) | 16 (0.4) |
| Acute stent thrombosis | 2 (0.0) | 5 (0.1) | 2 (0.1) | 5 (0.1) |
| Need for urgent CABG | 8 (0.2) | 6 (0.1) | 7 (0.2) | 6 (0.2) |
| IV study drug administered, No. (%) | 4345 (100.0) | 4317 (99.9) | 3895 (99.9) | 3868 (99.9) |
| Bolus administered, No. (%) | 4345 (100.0) | 4316 (99.9) | 3895 (99.9) | 3868 (99.9) |
| Infusion administered, No. (%) | 4344 (99.9) | 4317 (99.9) | 3894 (99.9) | 3868 (99.9) |

TABLE 6-continued

MITT and MITT NSTEMI Population

| Baseline characteristics | MITT | | MITT NSTEMI | |
|---|---|---|---|---|
| | Cangrelor (N = 4347) | Clopidogrel (N = 4320) | Cangrelor (N = 3897) | Clopidogrel (N = 3871) |
| Duration of infusion, hrs | 2.1 (2.0, 2.2) | 2.1 (2.0, 2.2) | 2.1 (2.0, 2.2) | 2.1 (2.0, 2.2) |
| Oral study drug administered, No. (%) | 4329 (99.6) | 4305 (99.7) | 3884 (99.7) | 3863 (99.8) |

Variables are presented as median (25th, 75th) unless otherwise indicated.
CABG denotes coronary artery bypass grafting;
CAD, coronary artery disease;
GP, glycoprotein;
HF, heart failure;
IV, intravenous;
LMWH, low molecular weight heparin;
MI, myocardial infarction;
MITT, modified intent to treat;
NSTEMI, non-ST-segment elevation myocardial infarction;
PAD, peripheral artery disease;
PCI, percutaneous coronary intervention;
PTCA, percutaneous transluminal coronary angioplasty;
STEMI, ST-segment elevation myocardial infarction;
TIA, transient ischemic attack;
UFH, unfractionated heparin.

TABLE 7

Safety Population

| Baseline characteristics | Cangrelor (N = 4374) | Clopidogrel (N = 4365) |
|---|---|---|
| Age, yrs | 62.0 (54.0, 70.0) | 62.0 (54.0, 71.0) |
| Sex, No. (%) | | |
| Male | 3229 (73.8) | 3149 (72.1) |
| Female | 1145 (26.2) | 1216 (27.9) |
| Race, No. (%) | | |
| White | 3610 (82.6) | 3558 (81.6) |
| Asian | 309 (7.1) | 312 (7.2) |
| Black | 208 (4.8) | 233 (5.3) |
| Hispanic | 206 (4.7) | 215 (4.9) |
| Other | 36 (0.8) | 41 (1.0) |
| Weight, kg | 84.0 (73.0, 97.0) | 84.0 (73.0, 97.0) |
| Height, cm | 172.0 (165.0, 178.0) | 172.0 (165.0, 178.0) |
| Stable angina, No. (%) | 661 (15.1) | 654 (15.0) |
| Unstable angina, No. (%) | 1091 (24.9) | 1074 (24.6) |
| Urgent NSTEMI, No. (%) | 629 (14.4) | 634 (14.5) |
| NSTEMI, No. (%) | 1529 (35.0) | 1529 (35.0) |
| STEMI, No. (%) | 463 (10.6) | 475 (10.9) |
| Medical history, No. (%) | | |
| Diabetes mellitus | 1337 (30.6) | 1325 (30.4) |
| Current smoker | 1233 (28.5) | 1257 (29.0) |
| Hypertension | 3143 (72.2) | 3083 (71.0) |
| Hyperlipidemia | 2787 (66.6) | 2728 (65.6) |
| Stroke/TIA | 220 (5.1) | 221 (5.1) |
| Family history of CAD | 1818 (45.8) | 1838 (46.5) |
| MI | 1064 (24.7) | 1067 (24.8) |
| PTCA/PCI | 1253 (28.7) | 1237 (28.4) |
| CABG | 550 (12.6) | 540 (12.4) |
| Congestive HF | 328 (7.6) | 332 (7.7) |
| PAD | 321 (7.5) | 309 (7.2) |
| Periprocedural medications, No. (%) | | |
| Bivalirudin | 1299 (29.7) | 1320 (30.2) |
| UFH | 2413 (55.2) | 2424 (55.5) |
| LMWH | 365 (8.4) | 340 (7.8) |
| GP IIb/IIIa | 1154 (26.4) | 1170 (26.8) |
| Study treatment | | |
| Number of target vessels, No. (%) | | |
| 1 | 3819 (88.0) | 3771 (87.4) |
| 2 | 482 (11.1) | 506 (11.7) |
| 3 | 38 (0.9) | 36 (0.8) |
| Drug-eluting stent, No. (%) | 2572 (59.3) | 2547 (59.0) |
| Non-drug-eluting stent, No. (%) | 1633 (37.6) | 1627 (37.7) |
| Angiographic complications (site reported) | | |
| Threatened abrupt closure | 13 (0.3) | 12 (0.3) |
| Unsuccessful procedure | 90 (2.1) | 103 (2.4) |
| Abrupt vessel closure | 24 (0.6) | 22 (0.5) |
| New thrombus or suspected thrombus | 17 (0.4) | 22 (0.5) |
| Acute stent thrombosis | 2 (0.0) | 5 (0.1) |
| Need for urgent CABG | 8 (0.2) | 6 (0.1) |
| IV study drug administered, No. (%) | 4368 (99.9) | 4354 (99.7) |
| Bolus administered, No. (%) | 4368 (99.9) | 4353 (99.7) |
| Infusion administered, No. (%) | 4365 (99.8) | 4352 (99.7) |

TABLE 7-continued

Safety Population

| Baseline characteristics | Cangrelor (N = 4374) | Clopidogrel (N = 4365) |
|---|---|---|
| Duration of infusion, hrs | 2.1 (2.0, 2.2) | 2.1 (2.0, 2.2) |
| Oral study drug administered, No. (%) | 4352 (99.5) | 4344 (99.5) |

Variables are presented as median (25th, 75th) unless otherwise indicated.
CABG denotes coronary artery bypass grafting;
CAD, coronary artery disease;
GP, glycoprotein;
HF, heart failure;
IV, intravenous;
LMWH, low molecular weight heparin;
MI, myocardial infarction;
NSTEMI, non-ST-segment elevation myocardial infarction;
PAD, peripheral artery disease;
PCI, percutaneous coronary intervention;
PTCA, percutaneous transluminal coronary angioplasty;
STEMI, ST-segment elevation myocardial infarction;
TIA, transient ischemic attack;
UFH, unfractionated heparin.

There were no significant differences regarding baseline characteristics. Enrolled patients were typical of a contemporary PCI population, being mostly men and having a median age of 62 years (54.0, 71.0). Diabetes was noted in 30.5% while hypertension or hyperlipidemia was present in the majority of patients. Previous cardiac events included MI in 24.7% and revascularization in 41.1% (28.6% PCI, 12.5% bypass grafting). Almost half (49%) of enrolled patients had NSTEMI at baseline while stable angina and unstable angina were the baseline diagnoses in 15.0% and 24.6%, respectively. The STEMI cohort included 996 (11.2%) patients.

During the index procedure, a majority of patients (55.1%) received unfractionated heparin, and 29.9% received bivalirudin. Glycoprotein IIb/IIIa inhibitors were used in 26.5% with most receiving eptifibatide (75.0%). Almost all (98%) patients in the ITT population received study drug. Sites were instructed to start PCI within 30 minutes of clopidogrel capsules.

PCI was attempted in all but 161 patients (1.8%), 65 in the cangrelor group (1.5%) and 96 in the clopidogrel group (2.2%). The median duration of PCI was 0.4 hours (0.2, 0.6) and the median time from hospital admission to PCI was 6.3 hours (2.6, 23.7). Most procedures involved single-vessel or two-vessel PCI (87.7% and 11.4%, respectively). Drug-eluting stents were used in the majority of interventions (59.1%), bare-metal stents were used in 37.6%.

Cangrelor was equivalent to 600 mg clopidogrel in the primary composite of all-cause mortality, MI, or ischemia-driven revascularization at 48 hours (7.5% vs 7.1%; OR 1.05, 95% CI 0.88, 1.24; P=0.59) (Table 8).

TABLE 8

48-hour endpoints for MITT Without STEMI Population

| | MITT Without STEMI | | | |
|---|---|---|---|---|
| | Cangrelor (N = 3897) | Clopidogrel (N = 3871) | OR (95% CI) | P Value |
| Adjudicated endpoints | | | | |
| Mortality/MI/IDR (primary endpoint) | 290 (7.5) | 276 (7.1) | 1.05 (0.88, 1.24) | 0.59 |
| MI | 278 (7.1) | 256 (6.6) | 1.09 (0.91, 1.29) | 0.36 |
| IDR | 13 (0.3) | 23 (0.6) | 0.56 (0.28, 1.11) | 0.10 |
| All-cause mortality | 8 (0.2) | 5 (0.1) | 1.59 (0.52, 4.87) | 0.42 |
| Stent thrombosis | 7 (0.2) | 11 (0.3) | 0.63 (0.25, 1.63) | 0.34 |
| Stroke | 6 (0.2) | 7 (0.2) | 0.85 (0.29, 2.54) | 0.77 |
| Q-wave MI | 4 (0.1) | 10 (0.3) | 0.40 (0.12, 1.27) | 0.12 |
| Exploratory endpoints | | | | |
| Mortality/Q-wave MI/IDR | 23 (0.6) | 34 (0.9) | 0.67 (0.39, 1.14) | 0.14 |
| Mortality/Q-wave MI/Stent thrombosis | 18 (0.5) | 23 (0.6) | 0.78 (0.42, 1.44) | 0.42 |

Figure 6A:
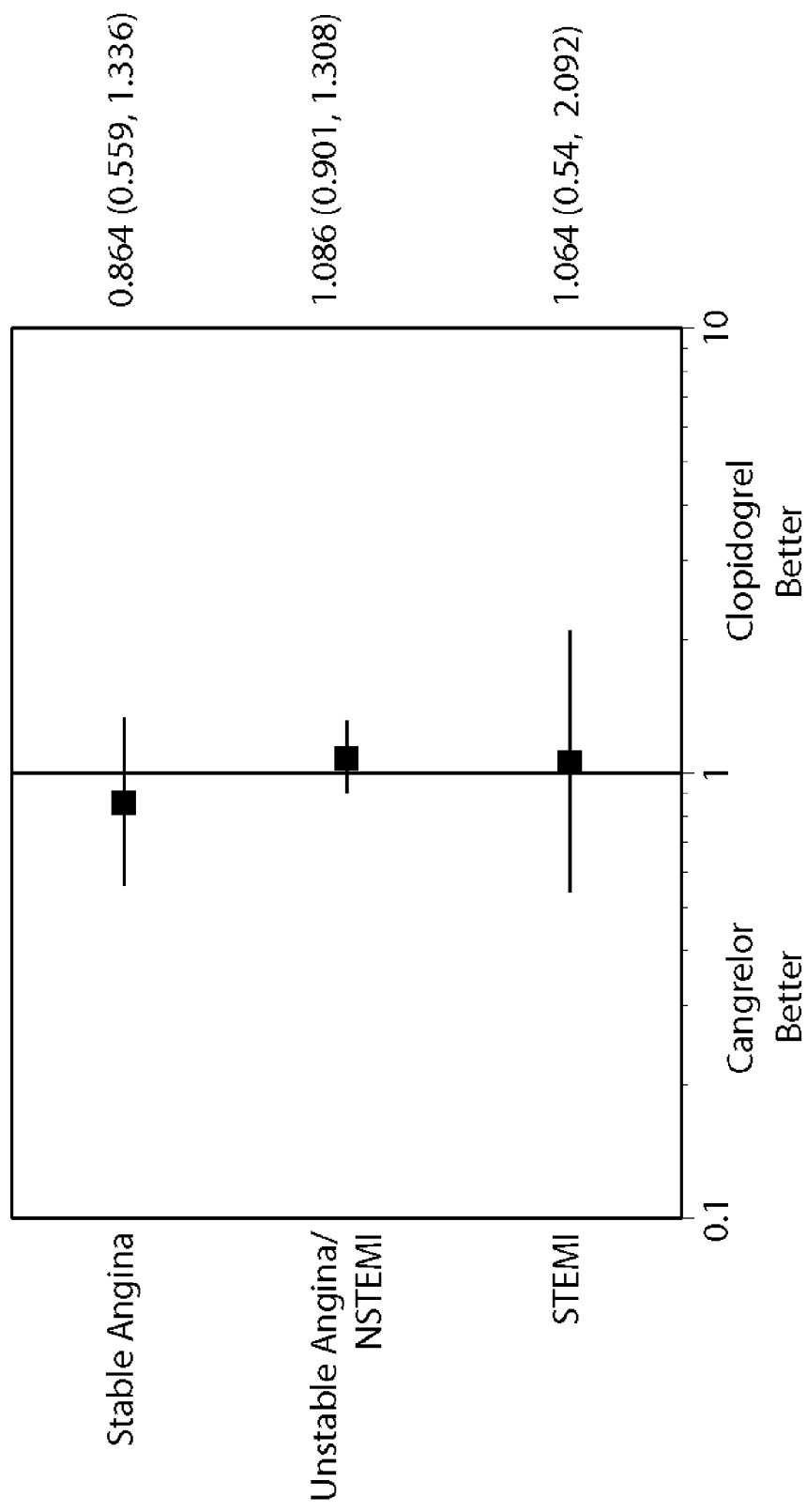
FIGS. 6A and 6B—display the primary endpoint odds ratio (OR) data for key subgroups in the study described in Example 2.
Figure 6B:
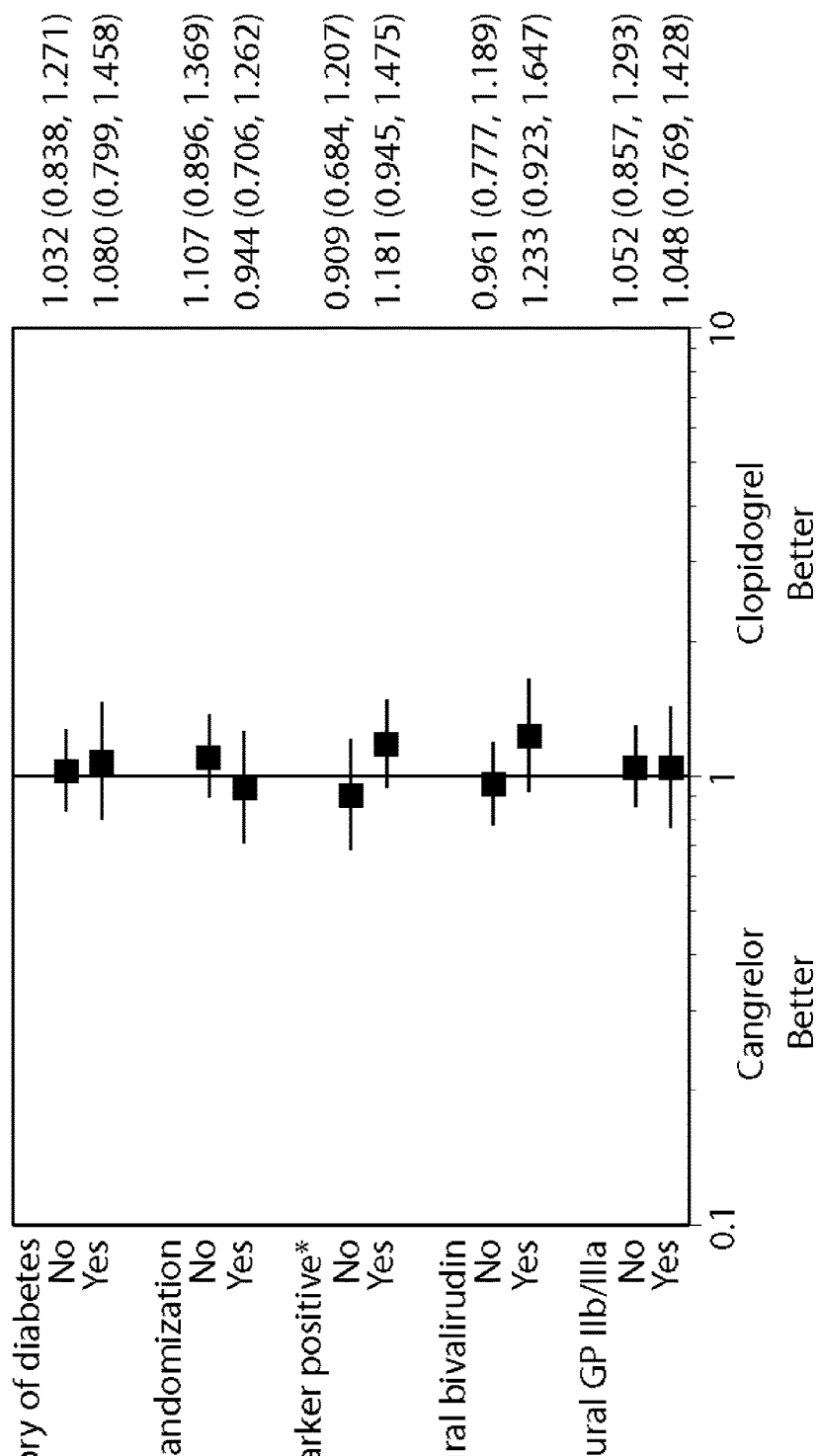

The primary efficacy composite did not differ at 30 days (Table 9). FIGS. 6A and 6B display the primary endpoint OR data for key subgroups.

TABLE 9

30-day endpoints for ITT, MITT, and Safety Populations

| | ITT | | | |
|---|---|---|---|---|
| | Cangrelor (N = 4433) | Clopidogrel (N = 4444) | OR (95% CI) | P Value |
| Mortality/MI/IDR | 381 (8.7) | 373 (8.5) | 1.026 (0.884, 1.192) | 0.7332 |
| MI | 318 (7.3) | 293 (6.7) | 1.095 (0.929, 1.291) | 0.2799 |
| IDR | 62 (1.4) | 69 (1.6) | 0.899 (0.637, 1.271) | 0.5475 |
| All-cause mortality | 40 (0.9) | 47 (1.1) | 0.852 (0.558, 1.301) | 0.4583 |
| Stent thrombosis | 27 (0.6) | 30 (0.7) | 0.902 (0.535, 1.519) | 0.6973 |
| Q-wave MI | 9 (0.2) | 15 (0.3) | 0.601 (0.263, 1.374) | 0.2273 |
| Mortality/Q-wave MI/IDR | 102 (2.3) | 119 (2.7) | 0.856 (0.655, 1.119) | 0.2550 |
| Mortality/Q-wave MI/Stent thrombosis | 68 (1.6) | 82 (1.9) | 0.829 (0.599, 1.146) | 0.2560 |

TABLE 9-continued 30-day endpoints for ITT, MITT, and Safety Populations

ITT Without STEMI

| | Cangrelor (N = 3946) | Clopidogrel (N = 3935) | OR (95% CI) | P Value |
|---|---|---|---|---|
| Mortality/MI/IDR | 345 (8.8) | 332 (8.6) | 1.037 (0.886, 1.215) | 0.6481 |
| MI | 298 (7.6) | 276 (7.1) | 1.081 (0.912, 1.281) | 0.3718 |
| IDR | 46 (1.2) | 54 (1.4) | 0.846 (0.569, 1.257) | 0.4072 |
| All-cause mortality | 32 (0.8) | 31 (0.8) | 1.027 (0.626, 1.687) | 0.9148 |
| Stent thrombosis | 20 (0.5) | 20 (0.5) | 0.995 (0.535, 1.852) | 0.9877 |
| Q-wave MI | 7 (0.2) | 15 (0.4) | 0.463 (0.189, 1.138) | 0.0933 |
| Mortality/Q-wave MI/IDR | 79 (2.0) | 88 (2.3) | 0.891 (0.656, 1.211) | 0.4620 |
| Mortality/Q-wave MI/Stent thrombosis | 54 (1.4) | 56 (1.4) | 0.959 (0.658, 1.397) | 0.8276 |

ITT With STEMI

| | Cangrelor (N = 487) | Clopidogrel (N = 509) | OR (95% CI) | P Value |
|---|---|---|---|---|
| Mortality/MI/IDR | 36 (7.6) | 41 (8.2) | 0.929 (0.582, 1.480) | 0.7553 |
| MI | 20 (4.2) | 17 (3.4) | 1.263 (0.653, 2.441) | 0.4882 |
| IDR | 16 (3.4) | 15 (3.0) | 1.139 (0.557, 2.331) | 0.7210 |
| All-cause mortality | 8 (1.7) | 16 (3.2) | 0.524 (0.222, 1.235) | 0.1397 |
| Stent thrombosis | 7 (1.5) | 10 (2.0) | 0.741 (0.280, 1.962) | 0.5460 |
| Q-wave MI | 2 (0.4) | 0 (0.0) | — | — |
| Mortality/Q-wave MI/IDR | 23 (4.9) | 31 (6.2) | 0.778 (0.447, 1.355) | 0.3760 |
| Mortality/Q-wave MI/Stent thrombosis | 14 (3.0) | 26 (5.2) | 0.560 (0.289, 1.085) | 0.0859 |

MITT

| | Cangrelor (N = 4347) | Clopidogrel (N = 4320) | OR (95% CI) | P Value |
|---|---|---|---|---|
| Mortality/MI/IDR | 376 (8.7) | 360 (8.4) | 1.042 (0.895, 1.211) | 0.5979 |
| MI | 315 (7.3) | 292 (6.8) | 1.078 (0.914, 1.271) | 0.3747 |
| IDR | 60 (1.4) | 66 (1.5) | 0.902 (0.634, 1.283) | 0.5660 |
| All-cause mortality | 40 (0.9) | 38 (0.9) | 1.046 (0.670, 1.635) | 0.8419 |
| Stent thrombosis | 27 (0.6) | 30 (0.7) | 0.894 (0.530, 1.506) | 0.6728 |
| Q-wave MI | 9 (0.2) | 15 (0.4) | 0.595 (0.260, 1.362) | 0.2194 |
| Mortality/Q-wave MI/IDR | 100 (2.3) | 107 (2.5) | 0.927 (0.703, 1.222) | 0.5904 |
| Mortality/Q-wave MI/Stent thrombosis | 68 (1.6) | 73 (1.7) | 0.924 (0.663, 1.290) | 0.6439 |

MITT Without STEMI

| | Cangrelor (N = 3897) | Clopidogrel (N = 3871) | OR (95% CI) | P Value |
|---|---|---|---|---|
| Mortality/MI/IDR | 342 (8.9) | 326 (8.5) | 1.044 (0.891, 1.224) | 0.5950 |
| MI | 297 (7.7) | 276 (7.2) | 1.072 (0.905, 1.272) | 0.4208 |
| IDR | 44 (1.1) | 52 (1.4) | 0.837 (0.559, 1.254) | 0.3882 |
| All-cause mortality | 32 (0.8) | 27 (0.7) | 1.177 (0.704, 1.967) | 0.5355 |
| Stent thrombosis | 20 (0.5) | 20 (0.5) | 0.991 (0.533, 1.846) | 0.9783 |
| Q-wave MI | 7 (0.2) | 15 (0.4) | 0.462 (0.188, 1.134) | 0.0917 |
| Mortality/Q-wave MI/IDR | 77 (2.0) | 82 (2.1) | 0.930 (0.679, 1.273) | 0.6489 |
| Mortality/Q-wave MI/Stent thrombosis | 54 (1.4) | 52 (1.4) | 1.030 (0.702, 1.511) | 0.8799 |

MITT With STEMI

| | Cangrelor (N = 450) | Clopidogrel (N = 449) | OR (95% CI) | P Value |
|---|---|---|---|---|
| Mortality/MI/IDR | 34 (7.8) | 34 (7.7) | 1.015 (0.619, 1.665) | 0.9534 |
| MI | 18 (4.1) | 16 (3.6) | 1.146 (0.577, 2.278) | 0.6965 |
| IDR | 16 (3.7) | 14 (3.2) | 1.165 (0.561, 2.416) | 0.6825 |
| All-cause mortality | 8 (1.8) | 11 (2.5) | 0.732 (0.292, 1.838) | 0.5072 |
| Stent thrombosis | 7 (1.6) | 10 (2.3) | 0.705 (0.266, 1.869) | 0.4821 |
| Q-wave MI | 2 (0.5) | 0 (0.0) | — | — |
| Mortality/Q-wave MI/IDR | 23 (5.3) | 25 (5.6) | 0.929 (0.519, 1.663) | 0.8039 |
| Mortality/Q-wave MI/Stent thrombosis | 14 (3.2) | 21 (4.7) | 0.665 (0.334, 1.325) | 0.2464 |

TABLE 9-continued 30-day endpoints for ITT, MITT, and Safety Populations

|  | Safety | | | |
| --- | --- | --- | --- | --- |
|  | Cangrelor (N = 4374) | Clopidogrel (N = 4365) | OR (95% CI) | P Value |
| Mortality/MI/IDR | 379 (8.8) | 365 (8.5) | 1.040 (0.895, 1.209) | 0.6074 |
| MI | 318 (7.4) | 293 (6.8) | 1.090 (0.925, 1.285) | 0.3039 |
| IDR | 60 (1.4) | 67 (1.6) | 0.893 (0.628, 1.268) | 0.5257 |
| All-cause mortality | 40 (0.9) | 41 (0.9) | 0.974 (0.629, 1.508) | 0.9053 |
| Stent thrombosis | 27 (0.6) | 30 (0.7) | 0.898 (0.533, 1.513) | 0.6858 |
| Q-wave MI | 9 (0.2) | 15 (0.3) | 0.598 (0.262, 1.368) | 0.2236 |
| Mortality/Q-wave MI/IDR | 100 (2.3) | 111 (2.6) | 0.897 (0.682, 1.179) | 0.4364 |
| Mortality/Q-wave MI/Stent thrombosis | 68 (1.6) | 76 (1.8) | 0.892 (0.641, 1.240) | 0.4954 |

Variables are presented as no. (%) unless otherwise indicated. CI denotes confidence interval; IDR, ischemia-driven revascularization; ITT, intent to treat; MI, myocardial infarction; MITT, modified intent to treat; OR, odds ratio; STEMI, ST-segment elevation myocardial infarction.

Forty-eight-hour bleeding events as observed in the safety population (including those with STEMI) are in Table 10. Reported adverse events were comparable between the groups (26.4% cangrelor, 25.7% clopidogrel) and discontinuation of study drug due to an adverse event was unusual in both groups (0.5% in both). Serious adverse events were infrequent and similar between the groups (2.7% in both). Dyspnea was reported in 1.0% of cangrelor patients compared with 0.4% of clopidogrel patients (P=0.001).

TABLE 10

48-hour bleeding events for safety population

| Bleeding events | Cangrelor (N = 4374) | Clopidogrel (N = 4365) | OR (95% CI) | P Value |
| --- | --- | --- | --- | --- |
| Access site bleeding requiring radiologic or surgical intervention | 6 (0.1) | 10 (0.2) | 0.60 (0.22, 1.65) | 0.32 |
| Hematoma ≥5 cm at puncture site | 85 (1.9) | 76 (1.7) | 1.12 (0.82, 1.53) | 0.48 |
| Intracranial hemorrhage | 1 (0.0) | 0 (0.0) | | |
| Intraocular | 2 (0.0) | 0 (0.0) | | |
| Reoperation for bleeding | 1 (0.0) | 1 (0.0) | 1.00 (0.06, 15.96) | 1.00 |
| Retroperitoneal | 15 (0.3) | 10 (0.2) | 1.50 (0.67, 3.34) | 0.32 |
| Ecchymosis | 284 (6.5) | 234 (5.4) | 1.23 (1.03, 1.47) | 0.03 |
| Epistaxis | 9 (0.2) | 22 (0.5) | 0.41 (0.19, 0.89) | 0.02 |
| Hematoma <5 cm at puncture site | 251 (5.7) | 222 (5.1) | 1.14 (0.94, 1.37) | 0.18 |
| Oozing at puncture site | 400 (9.1) | 319 (7.3) | 1.28 (1.10, 1.49) | 0.002 |
| Thrombocytopenia | 6 (0.1) | 7 (0.2) | 0.86 (0.29, 2.55) | 0.78 |
| Hemodynamic compromise | 9 (0.2) | 11 (0.3) | 0.82 (0.34, 1.97) | 0.65 |
| Any blood transfusion | 46 (1.1) | 42 (1.0) | 1.09 (0.72, 1.67) | 0.68 |
| Any platelet transfusion | 6 (0.1) | 5 (0.1) | 1.20 (0.37, 3.93) | 0.77 |
| Drop in hemoglobin and/or hematocrit | 91 (2.1) | 63 (1.4) | 1.45 (1.05, 2.01) | 0.02 |
| Bleed scoring criteria | | | | |
| ACUITY criteria | | | | |
| Minor bleeding | 768 (17.6) | 663 (15.2) | 1.19 (1.06, 1.33) | 0.003 |
| Major bleeding | 158 (3.6) | 126 (2.9) | 1.26 (0.99, 1.60) | 0.06 |
| GUSTO criteria | | | | |
| Mild bleeding | 858 (19.6) | 739 (16.9) | 1.20 (1.07, 1.34) | 0.001 |
| Moderate bleeding | 41 (0.9) | 34 (0.8) | 1.21 (0.76, 1.90) | 0.42 |
| Severe/life-threatening bleeding | 10 (0.2) | 11 (0.3) | 0.91 (0.39, 2.14) | 0.82 |
| TIMI criteria | | | | |
| Minor bleeding | 36 (0.8) | 26 (0.6) | 1.39 (0.84, 2.30) | 0.21 |
| Major bleeding | 19 (0.4) | 14 (0.3) | 1.36 (0.68, 2.71) | 0.39 |

Variables are presented as no. (%) unless otherwise indicated. The bleeding options under each criterion are not mutually exclusive. For example, a patient may have a clinically significant bleed and a minor bleed based on the ACUITY criteria, if more than 1 bleed is present. Each patient will be counted once for each criteria level, regardless of the number of bleeds identified under each criterion.

Key secondary and composite exploratory (post-hoc) endpoints are displayed in Table 11.

TABLE 11

48-hour endpoints for ITT, MITT, and Safety Populations

| | MITT Without STEMI | | | |
|---|---|---|---|---|
| | Cangrelor (N = 3897) | Clopidogrel (N = 3871) | OR (95% CI) | P Value |
| Mortality/MI/IDR (Prespecified primary endpoint) | 290 (7.5) | 276 (7.1) | 1.048 (0.883, 1.243) | 0.5929 |
| MI | 278 (7.1) | 256 (6.6) | 1.085 (0.910, 1.294) | 0.3616 |
| IDR | 13 (0.3) | 23 (0.6) | 0.560 (0.283, 1.108) | 0.0957 |
| All-cause mortality | 8 (0.2) | 5 (0.1) | 1.591 (0.520, 4.869) | 0.4155 |
| Stent thrombosis | 7 (0.2) | 11 (0.3) | 0.632 (0.245, 1.631) | 0.3427 |
| Stroke | 6 (0.2) | 7 (0.2) | 0.852 (0.286, 2.536) | 0.7730 |
| Q-wave MI | 4 (0.1) | 10 (0.3) | 0.397 (0.124, 1.267) | 0.1186 |
| Mortality/Q-wave MI/IDR | 23 (0.6) | 34 (0.9) | 0.670 (0.394, 1.140) | 0.1399 |
| Mortality/Q-wave MI/Stent thrombosis | 18 (0.5) | 23 (0.6) | 0.777 (0.419, 1.442) | 0.4233 |

| | ITT | | | |
|---|---|---|---|---|
| | Cangrelor (N = 4433) | Clopidogrel (N = 4444) | OR (95% CI) | P Value |
| Mortality/MI/IDR | 312 (7.1) | 297 (6.7) | 1.058 (0.898, 1.248) | 0.4990 |
| MI | 294 (6.7) | 265 (6.0) | 1.122 (0.945, 1.331) | 0.1899 |
| IDR | 21 (0.5) | 31 (0.7) | 0.678 (0.389, 1.182) | 0.1710 |
| All-cause mortality | 9 (0.2) | 11 (0.2) | 0.821 (0.340, 1.983) | 0.6607 |
| Stent thrombosis | 11 (0.2) | 15 (0.3) | 0.735 (0.337, 1.603) | 0.4393 |
| Stroke | 6 (0.1) | 8 (0.2) | 0.752 (0.261, 2.170) | 0.5986 |
| Q-wave MI | 4 (0.1) | 10 (0.2) | 0.401 (0.126, 1.279) | 0.1226 |
| Mortality/Q-wave MI/IDR | 32 (0.7) | 48 (1.1) | 0.667 (0.425, 1.045) | 0.0770 |
| Mortality/Q-wave MI/Stent thrombosis | 23 (0.5) | 33 (0.7) | 0.698 (0.409, 1.191) | 0.1869 |

| | ITT Without STEMI | | | |
|---|---|---|---|---|
| | Cangrelor (N = 3946) | Clopidogrel (N = 3935) | OR (95% CI) | P Value |
| Mortality/MI/IDR | 292 (7.4) | 277 (7.1) | 1.056 (0.890, 1.252) | 0.5323 |
| MI | 278 (7.1) | 256 (6.5) | 1.090 (0.914, 1.299) | 0.3378 |
| IDR | 15 (0.4) | 23 (0.6) | 0.649 (0.338, 1.246) | 0.1943 |
| All-cause mortality | 8 (0.2) | 6 (0.2) | 1.331 (0.461, 3.839) | 0.5969 |
| Stent thrombosis | 7 (0.2) | 11 (0.3) | 0.634 (0.246, 1.638) | 0.3469 |
| Stroke | 6 (0.2) | 7 (0.2) | 0.855 (0.287, 2.546) | 0.7784 |
| Q-wave MI | 4 (0.1) | 10 (0.3) | 0.398 (0.125, 1.272) | 0.1202 |
| Mortality/Q-wave MI/IDR | 25 (0.6) | 35 (0.9) | 0.711 (0.425, 1.190) | 0.1941 |
| Mortality/Q-wave MI/Stent thrombosis | 18 (0.5) | 24 (0.6) | 0.747 (0.405, 1.379) | 0.3511 |

| | ITT With STEMI | | | |
|---|---|---|---|---|
| | Cangrelor (N = 487) | Clopidogrel (N = 509) | OR (95% CI) | P Value |
| Mortality/MI/IDR | 20 (4.1) | 20 (3.9) | 1.054 (0.560, 1.985) | 0.8703 |
| MI | 16 (3.3) | 9 (1.8) | 1.900 (0.831, 4.341) | 0.1280 |
| IDR | 6 (1.2) | 8 (1.6) | 0.786 (0.271, 2.283) | 0.6584 |
| All-cause mortality | 1 (0.2) | 5 (1.0) | 0.209 (0.024, 1.793) | 0.1534 |
| Stent thrombosis | 4 (0.8) | 4 (0.8) | 1.052 (0.262, 4.321) | 0.9428 |
| Stroke | 0 (0.0) | 1 (0.2) | — | — |
| Q-wave MI | 0 (0.0) | 0 (0.0) | — | — |
| Mortality/Q-wave MI/IDR | 7 (1.5) | 13 (2.6) | 0.560 (0.222, 1.416) | 0.2204 |
| Mortality/Q-wave MI/Stent thrombosis | 5 (1.0) | 9 (1.8) | 0.580 (0.193, 1.743) | 0.3320 |

TABLE 11-continued 48-hour endpoints for ITT, MITT, and Safety Populations

| | MITT | | | |
|---|---|---|---|---|
| | Cangrelor (N = 4347) | Clopidogrel (N = 4320) | OR (95% CI) | P Value |
| Mortality/MI/IDR | 308 (7.1) | 293 (6.8) | 1.049 (0.889, 1.238) | 0.5709 |
| MI | 292 (6.7) | 264 (6.1) | 1.107 (0.932, 1.315) | 0.2451 |
| IDR | 19 (0.4) | 30 (0.7) | 0.628 (0.353, 1.118) | 0.1140 |
| All-cause mortality | 9 (0.2) | 9 (0.2) | 0.995 (0.394, 2.508) | 0.9910 |
| Stent thrombosis | 11 (0.3) | 15 (0.3) | 0.729 (0.334, 1.588) | 0.4261 |
| Stroke | 6 (0.1) | 7 (0.2) | 0.852 (0.286, 2.538) | 0.7742 |
| Q-wave MI | 4 (0.1) | 10 (0.2) | 0.397 (0.125, 1.268) | 0.1190 |
| Mortality/Q-wave MI/IDR | 30 (0.7) | 45 (1.0) | 0.661 (0.416, 1.051) | 0.0801 |
| Mortality/Q-wave MI/Stent thrombosis | 23 (0.5) | 31 (0.7) | 0.737 (0.429, 1.265) | 0.2681 |

| | MITT With STEMI | | | |
|---|---|---|---|---|
| | Cangrelor (N = 450) | Clopidogrel (N = 449) | OR (95% CI) | P Value |
| Mortality/MI/IDR | 18 (4.0) | 17 (3.8) | 1.064 (0.541, 2.092) | 0.8578 |
| MI | 14 (3.1) | 8 (1.8) | 1.778 (0.739, 4.282) | 0.1991 |
| IDR | 6 (1.3) | 7 (1.6) | 0.857 (0.286, 2.571) | 0.7833 |
| All-cause mortality | 1 (0.2) | 4 (0.9) | 0.249 (0.028, 2.235) | 0.2143 |
| Stent thrombosis | 4 (0.9) | 4 (0.9) | 1.002 (0.249, 4.033) | 0.9975 |
| Stroke | 0 (0.0) | 0 (0.0) | — | — |
| Q-wave MI | 0 (0.0) | 0 (0.0) | — | — |
| Mortality/Q-wave MI/IDR | 7 (1.6) | 11 (2.5) | 0.632 (0.243, 1.645) | 0.3473 |
| Mortality/Q-wave MI/Stent thrombosis | 5 (1.1) | 8 (1.8) | 0.622 (0.202, 1.917) | 0.4084 |

| | Safety | | | |
|---|---|---|---|---|
| | Cangrelor (N = 4374) | Clopidogrel (N = 4365) | OR (95% CI) | P Value |
| Mortality/MI/IDR | 310 (7.1) | 294 (6.7) | 1.058 (0.896, 1.248) | 0.5073 |
| MI | 294 (6.7) | 265 (6.1) | 1.116 (0.940, 1.325) | 0.2091 |
| IDR | 19 (0.4) | 30 (0.7) | 0.631 (0.355, 1.123) | 0.1175 |
| All-cause mortality | 9 (0.2) | 9 (0.2) | 0.999 (0.396, 2.519) | 0.9984 |
| Stent thrombosis | 11 (0.3) | 15 (0.3) | 0.732 (0.336, 1.595) | 0.4326 |
| Stroke | 6 (0.1) | 7 (0.2) | 0.856 (0.288, 2.550) | 0.7803 |
| Q-wave MI | 4 (0.1) | 10 (0.2) | 0.399 (0.125, 1.273) | 0.1207 |
| Mortality/Q-wave MI/IDR | 30 (0.7) | 45 (1.0) | 0.664 (0.417, 1.056) | 0.0834 |
| Mortality/Q-wave MI/Stent thrombosis | 23 (0.5) | 31 (0.7) | 0.740 (0.431, 1.271) | 0.2751 |

Variables are presented as no. (%) unless otherwise indicated. CI denotes confidence interval; IDR, ischemia-driven revascularization; ITT, intent to treat; MI, myocardial infarction; MITT, modified intent to treat; OR, odds ratio; STEMI, ST-segment elevation myocardial infarction.

A substudy was conducted at 15 sites to evaluate platelet function during infusion and to assess whether the administration of a cangrelor infusion prior to administration of clopidogrel 600 mg has any effect on platelet inhibition by clopidogrel. Patients in the substudy were required to be clopidogrel naïve and could not have received glycoprotein IIb/IIIa inhibition during the procedure. Platelet function parameters were measured using the VerifyNow $P2Y_{12}$ Assay (Accumetrics, San Diego, Calif.). Samples were taken before study drug administration, at approximately 2 hours (during cangrelor/placebo infusion), and 10 hours or next day following randomization.

The median baseline $P2Y_{12}$ reaction units (PRU) from the VerifyNow $P2Y_{12}$ assay were 335 in the cangrelor arm (264, 384; n=97) and 329 in the clopidogrel arm (285.5, 376.5; n=100). During the study drug infusion, the median PRU was significantly lower in the cangrelor arm (93.5; 40.0, 173.5; n=64) compared with the clopidogrel arm during the same time period (277; 206.0, 355.0; n=74). At 12-24 hours after discontinuation of the cangrelor infusion, the median PRU was 228 in the cangrelor arm (156.0, 298.0; n=87) and 206 in the clopidogrel arm (135.0, 274.0; n=87).

The results of this study demonstrated that the benefits of cangrelor infusion were equivalent to those of 600 mg clopidogrel using the predefined primary endpoint, although significantly higher levels of periprocedural platelet inhibition were achieved with cangrelor.

Example 3—Comparison of Cangrelor to Clopidogrel Standard of Care Therapy in Patients Who Require Percutaneous Coronary Intervention The efficacy and safety of cangrelor versus clopidogrel standard of care therapy was examined in patients with atherosclerosis undergoing PCI in a double-blind, placebo-controlled, double-dummy study.

Figure 7:
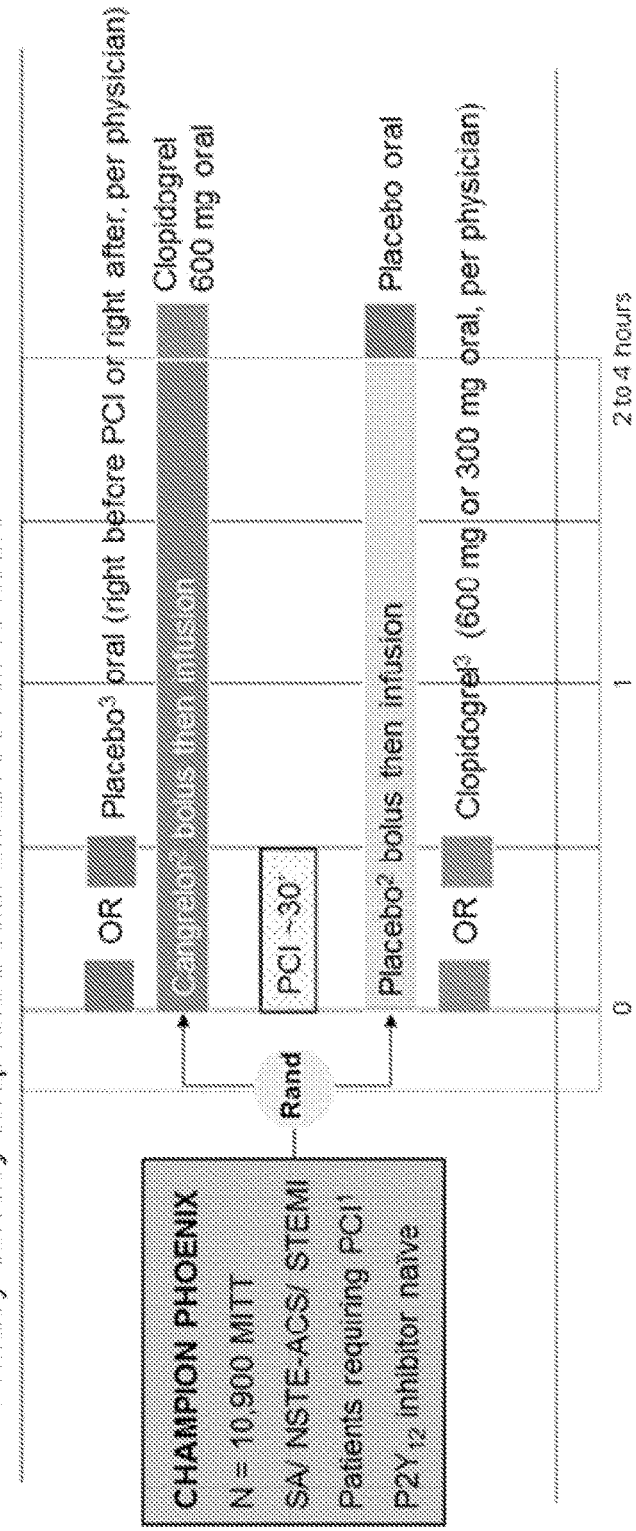
FIG. 7—diagram showing trial design for the study described in Example 3.

A total of 11,145 patients underwent randomization at 153 sites in 12 countries from Sep. 30, 2010 to Oct. 3, 2012. Randomization was performed before PCI with the use of an interactive voice-response or Web-response system, with stratification according to site, baseline status (normal or abnormal, as defined by a combination of biomarker levels, electrocardiographic changes, and symptoms), and intended loading dose of clopidogrel (600 mg or 300 mg). Randomization divided the patients into two groups: the cangrelor group and the clopidogrel group. Patients assigned to the cangrelor group were administered: (i) placebo capsules (before or immediately after PCI to match clopidogrel capsules administered in the clopidogrel group); (ii) a cangrelor bolus (30 μg/kg)/infusion (4 μg/kg/min); and (iii) capsules containing 600 mg of clopidogrel administered at the end of infusion. Patients assigned to the clopidogrel group were administered: (i) clopidogrel capsules (300 mg or 600 mg before or immediately after PCI, with the dose and timing of administration determined at the discretion of the site investigator); (ii) a placebo bolus/infusion (to match the cangrelor bolus/infusion administered in the cangrelor group); and (iii) placebo capsules administered at the end of the infusion (to match the capsules containing 600 mg of clopidogrel administered at the end of the infusion in the cangrelor group). The cangrelor or placebo infusion was administered for at least 2 hours or the duration of the PCI procedure, whichever was longer. A summary of the study design is shown in FIG. 7.

The protocol called for aspirin (75 to 325 mg) to be administered to all patients. The protocol also called for a maintenance dose of clopidogrel (75 mg) to be administered during the first 48 hours after randomization; thereafter, clopidogrel or another $P2Y_{12}$ inhibitor could be administered at the discretion of the investigator, according to local guidelines. The choice of a periprocedural anticoagulant (bivalirudin, unfractionated heparin, low-molecular-weight heparin, or fondaparinux) was also at the discretion of the investigator. Glycoprotein IIb/IIIa inhibitors were allowed only as rescue therapy during PCI to treat new or persistent thrombus formation, slow or no reflow, side-branch compromise, dissection, or distal embolization. The investigator at the site determined the protocol for management of the arterial sheath.

The inclusion criteria for the trial were men or nonpregnant women, 18 years of age or older with coronary atherosclerosis who required PCI for stable angina, a non-ST-segment elevation acute coronary syndrome, or ST-segment elevation myocardial infarction (STEMI). Patients were required to provide written informed consent.

Major exclusion criteria were receipt of a $P2Y_{12}$ inhibitor or abciximab at any time in the 7 days before randomization and receipt of eptifibatide or tirofiban or fibrinolytic therapy in the 12 hours before randomization.

The primary efficacy end point was the composite rate of death from any cause, myocardial infarction, IDR, or stent thrombosis in the 48 hours after randomization in the modified intention-to-treat population (which comprised patients who actually underwent PCI and received the study drug). The protocol specified that if more than 15% of the patients received a 300-mg loading dose of clopidogrel (as compared with a 600-mg dose) at the time of randomization, the primary analysis was to be adjusted for loading dose in addition to baseline status. The key secondary end point was the incidence of stent thrombosis at 48 hours. This end point included definite stent thrombosis, defined according to the criteria of the Academic Research Consortium, or intraprocedural stent thrombosis, which was assessed, with group assignments concealed, at an angiographic core laboratory (Cardiovascular Research Foundation). Intraprocedural stent thrombosis was defined as any new or worsened thrombus related to the stent procedure that was confirmed angiographically. Events of death, myocardial infarction, IDR, and stent thrombosis that occurred during the first 30 days after randomization were adjudicated by the clinical events committee at the Duke Clinical Research Institute. The criteria that the clinical events committee used to define myocardial infarction are provided in Tables 12A and 12B. The study adhered to the universal definition of myocardial infarction for myocardial infarction unrelated to PCI but expanded on the definition of PCI-related myocardial infarction.

TABLE 12A

Baseline status assessment and trigger logic.*

| Baseline Status | Cardiac Markers (Troponin Preferred; use CKMB if not available) | $ECG^1$ (12 Lead) | Ischemic Symptoms[2] (Angina or equivalent symptoms at rest) |
| --- | --- | --- | --- |
| Baseline Normal (No MI at baseline) | | | |
| Stable angina/elective | All samples within 6 hours prior to access sample are normal (1 sample sufficient; samples can be <6 hr apart) | AND: no presumed new changes | AND: no ongoing ACS symptoms or symptoms within 6 hours prior to access site sample |
| NSTE-ACS | 2 normal samples ≥6 hours apart (sample 2 is the access sample) | AND: no presumed new changes | AND: no ongoing ACS symptoms or symptoms within 6 hours prior to access site sample |
| Baseline Abnormal (MI ongoing at baseline) | | | |
| Decreasing & returns to normal | 2 samples ≥6 hours apart with most recent access sample returned to normal | AND: no presumed new ECG changes | AND: no recent symptoms within 6 hours prior to access site sample |
| Decreasing & remains abnormal | 2 samples ≥6 hours apart with most recent access sample fallen at least 20% | AND: no presumed new ECG changes | AND: no recent symptoms within 6 hours prior to access site sample |

TABLE 12A-continued

Baseline status assessment and trigger logic.*

| Baseline Status | Cardiac Markers (Troponin Preferred; use CKMB if not available) | ECG[1] (12 Lead) | Ischemic Symptoms[2] (Angina or equivalent symptoms at rest) |
|---|---|---|---|
| Increasing | Insufficient biomarker data for all other categories | OR: Presumed new changes including STEMI | OR: recent symptoms within 6 hours prior to access site sample |
| Baseline unknown | No samples pre PCI available | | |

*CKMB denotes creatine kinase-myocardial band isoenzyme, ECG denotes electrocardiography, MI denotes myocardial infarction, NSTE-ACS denotes non-ST-segment elevation acute coronary syndrome, and STEMI denotes ST-segment elevation myocardial infarction.
[1]ECG changes: ST segment elevation/depression >0.1 mV (>1 mm) in at least 2 contiguous leads; new LBBB; new Q wave (greater than 0.03 seconds). ECG collection post PCI: within 1 hour after PCI; pre-discharge.
[2]Ischemic symptoms: angina or equivalent symptoms that need to be treated medically or lasting ≥20 min. Ischemic symptoms as determined by the treating physician include but are not limited to weakness, shortness of breath, wheezing, tiredness, fainting, sweating, nausea/vomiting, abdominal pain, back pain, jaw pain, palpitations, fast heartbeat, drug use for chest pain (nitroglycerin, morphine, beta blocker, etc).

TABLE 12B

Definition of PCI-related myocardial infarction.*

| Endpoint Definition | Baseline MI status | Non-biomarker Evidence of Ischemia | Biomarkers post PCI (core lab CKMB[1] mass) |
|---|---|---|---|
| MI | Baseline normal Stable angina/NSTE-ACS | Not required to qualify MI | elevation ≥3x ULN |
| Reinfarction | Baseline decreasing & returns to normal (No intervening event from elevated sample to PCI) | Not required to qualify MI | elevation ≥3x ULN |
| | Baseline decreasing & remains abnormal (No intervening event from elevated sample to PCI) | (1 of 3): Angiographic complications[2] OR Ischemic symptoms[3] OR New ECG changes[4] | AND: Re-elevation of CKMB ≥3x ULN and ≥50% |
| | Baseline abnormal & increasing OR Baseline unknown | (2 of 2): Angiographic complication AND New ECG changes | AND: Re-elevation of CKMB ≥3x ULN and ≥50% |

*MI denotes myocardial infarction, CKMB denotes creatine kinase-myocardial band isoenzyme, NSTE-ACS denotes non-ST-segment elevation acute coronary syndrome, ULN denotes upper limit of normal, and PCI denotes percutaneous coronary intervention.
[1]CKMB collection post PCI: 6 hourly collection through 24 hours (minimum of 3 samples required). Core lab values take priority; hospital labs may be used if core lab not available (CKMB priority but troponin may be used).
[2]Angiographic evidence of complication (assessed by the angiographic core laboratory):
New onset of vessel closure or compromise defined as TIMI 0/1 flow after baseline TIMI 2/3 flow (also termed acute closure or no reflow); or
TIMI 2 flow after baseline TIMI 3 flow (also termed slow reflow); or
Sustained distal embolization; or
Sustained side-branch closure of a vessel ≥2 mm in diameter; or
Intra-Procedural Thrombotic Event (IPTE): new or worsening thrombus formation at any time during the procedure. The occurrence of IPTE can be a stent related or not stent related complication phenomena or intra-procedural stent thrombosis (IPST) new or worsening thrombus related to the stent or abrupt closure due to thrombosis. Abrupt closure due to non-thrombotic causes, including major dissections, perforation, or other etiologies, will not be considered IPST. If a non-thrombotic cause of abrupt stent closure cannot be definitively determined, the cause will be considered IPST. IPST may present as either acute thrombotic stent closure after a stent was implanted in a patient with a patent vessel beforehand, or new thrombus formation within or adjacent to a stent in a vessel in which thrombus either was not present or had diminished or resolved before the stent was implanted.
[3]Ischemic symptoms: angina or equivalent symptoms that need to be treated medically or lasting ≥20 min. Ischemic symptoms as determined by the treating physician include but are not limited to weakness, shortness of breath, wheezing, tiredness, fainting, sweating, nausea/vomiting, abdominal pain, back pain, jaw pain, palpitations, fast heartbeat, drug use for chest pain (nitroglycerin, morphine, beta blocker, etc.).
[4]ECG changes: ST segment elevation/depression >0.1 mV (>1 mm) in at least 2 contiguous leads; new LBBB; new Q wave (greater than 0.03 seconds). ECG collection post PCI: within 1 hour after PCI; pre-discharge.

The primary safety end point was severe bleeding not related to coronary-artery bypass grafting, according to the Global Use of Strategies to Open Occluded Coronary Arteries (GUSTO) criteria, at 48 hours. Several other bleeding definitions were also applied.

On the basis of prior studies, it was assumed that the rate of the composite primary end point would be 5.1% in the clopidogrel group and 3.9% in the cangrelor group, representing a 24.5% reduction in the odds ratio with cangrelor. It was estimated that approximately 10,900 patients would need to be enrolled for the study to have 85% power to detect that reduction. A two-sided overall alpha level of 0.05 was used for all analyses. This study had an adaptive design with conditional power calculation and potential for reestimation of the sample size, if necessary, after the interim analysis that was scheduled to be performed after 70% of the patients were enrolled.

The numbers and percentages of patients within each analysis population (modified intention-to-treat, intention-to-treat, and safety) were summarized according to treatment group. The primary efficacy analysis of the rate of the composite end point of death from any cause, myocardial infarction, IDR, or stent thrombosis (with all events adjudicated by the clinical events committee) in the 48 hours after randomization was conducted in the modified intention-to-treat population. The primary safety analysis was conducted in the safety population, which comprised all patients who underwent randomization and received at least one dose of the study drug; patients were classified according to the actual treatment received. All calculations and statistical analyses were performed with the use of SAS software, version 9.2.

Figure 8:
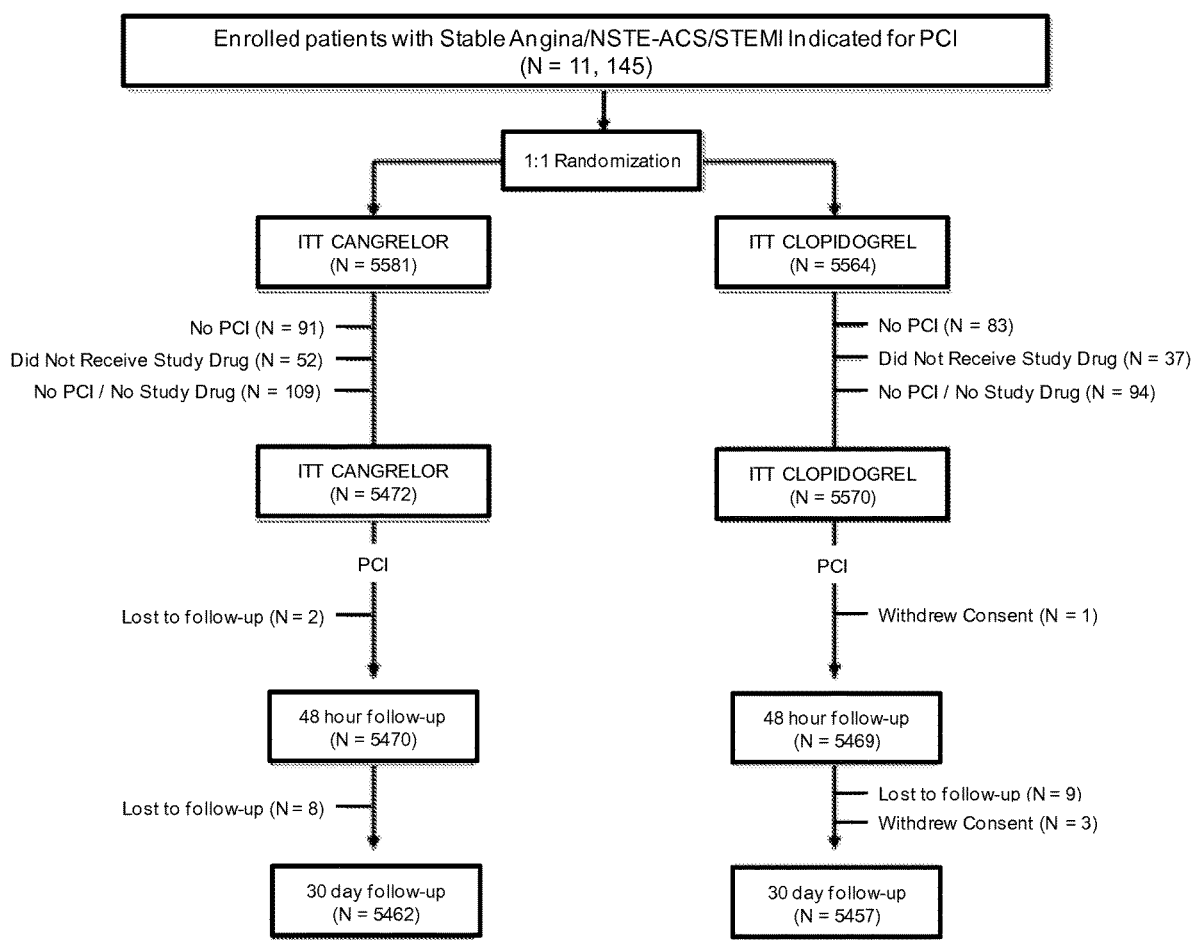
FIG. 8—diagram showing the modified intention-to-treat population in the study described in Example 3.

Of the 11,145 patients who underwent randomization, 203 did not undergo PCI or did not receive a study drug; therefore, the modified intention-to-treat population comprised 10,942 patients (FIG. 8). The baseline characteristics were well balanced between the two groups. The characteristics of the patients and the procedure are shown in Tables 13 and 14.

TABLE 13

Baseline characteristics of the patients and characteristics of the procedure in the modified intention-to-treat population, according to treatment group.*

| Characteristic | Cangrelor (N = 5472) | Clopidogrel (N = 5470) |
|---|---|---|
| Age - yr | | |
| Median | 64.0 | 64.0 |
| Interquartile range | 56-72 | 56-72 |
| Female sex - no. (%) | 1558 (28.5) | 1493 (27.3) |
| White race - no./total no. (%)† | 5132/5469 (93.8) | 5120/5463 (93.7) |
| Weight - kg | | |
| Median | 84.0 | 84.0 |
| Interquartile range | 73-95 | 74-96 |
| Diagnosis at presentation - no. (%) | | |
| Stable angina | 3121 (57.0) | 3019 (55.2) |
| NSTE-ACS | 1389 (25.4) | 1421 (26.0) |
| STEMI | 962 (17.6) | 1030 (18.8) |
| Region - no. (%) | | |
| United States | 2048 (37.4) | 2049 (37.5) |
| Other countries | 3424 (62.6) | 3421 (62.5) |
| Cardiac-biomarker status - no./total no. (%)‡ | | |
| Normal | 3520/5467 (64.4) | 3432/5466 (62.8) |
| Abnormal | 1947/5467 (35.6) | 2034/5466 (37.2) |

TABLE 13-continued

Baseline characteristics of the patients and characteristics of the procedure in the modified intention-to-treat population, according to treatment group.*

| Characteristic | Cangrelor (N = 5472) | Clopidogrel (N = 5470) |
|---|---|---|
| Medical history - no./total no (%) | | |
| Diabetes mellitus | 1519/5464 (27.8) | 1536/5463 (28.1) |
| Current smoker | 1504/5339 (28.2) | 1549/5339 (29.0) |
| Hypertension | 4374/5459 (80.1) | 4332/5454 (79.4) |
| Hyperlipidemia | 3363/4851 (69.3) | 3338/4836 (69.0) |
| Prior stroke or TIA | 271/5455 (5.0) | 244/5452 (4.5) |
| Prior myocardial infarction | 1092/5441 (20.1) | 1175/5431 (21.6) |
| PTCA or PCI | 1268/5462 (23.2) | 1333/5461 (24.4) |
| CABG | 578/5466 (10.6) | 500/5464 (9.2) |
| Congestive heart failure | 552/5460 (10.1) | 584/5456 (10.7) |
| Peripheral artery disease | 447/5407 (8.3) | 385/5419 (7.1) |
| Periprocedural medications - no./total no. (%) | | |
| Clopidogrel, 300-mg loading dose | 1405/5472 (25.7) | 1401/5470 (25.6) |
| Clopidogrel, 600-mg loading dose | 4067/5472 (74.3) | 4069/5470 (74.4) |
| Bivalirudin | 1252/5472 (22.9) | 1269/5468 (23.2) |
| Unfractionated heparin | 4272/5472 (78.1) | 4276/5469 (78.2) |
| Low-molecular-weight heparin | 732/5472 (13.4) | 753/5468 (13.8) |
| Fondaparinux | 156/5471 (2.9) | 135/5470 (2.5) |
| Aspirin | 5164/5469 (94.4) | 5148/5465 (94.2) |
| Duration of PCI - min | | |
| Median | 18 | 17 |
| Interquartile range | 10-30 | 10-30 |
| Drug-eluting stent - no. (%) | 3061 (55.9) | 3020 (55.2) |
| Bare-metal stent - no. (%) | 2308 (42.2) | 2344 (42.9) |
| Balloon angioplasty - no. (%) | 292 (5.3) | 273 (5.0) |

*Denominators exclude patients in whom the status was reported as unknown by the study center. There were no significant differences between the two groups, except for a history of coronary-artery bypass grafting (CABG) (P = 0.01), prior myocardial infarction (P = 0.04), and peripheral-artery disease (P = 0.02). NSTE-ACS denotes non-ST-segment elevation acute coronary syndrome, PCI percutaneous coronary intervention, PTCA percutaneous transluminal coronary angioplasty, STEMI ST-segment elevation myocardial infarction, and TIA transient ischemic attack.
†Race was self-reported.
‡Cardiac biomarker status was considered to be abnormal if at least one of the baseline troponin I or T levels, obtained within 72 hours before randomization or after randomization but before initiation of the study drug, was greater than the upper limit of the normal range, as determined by the local laboratory. If the baseline troponin level was not available, the baseline MB fraction of creatine kinase was used.

TABLE 14

Additional baseline and procedural characteristics for the modified intention-to-treat population, according to the treatment group.*

| Characteristic | Cangrelor (N = 5472) | Clopidogrel (N = 5470) |
|---|---|---|
| Age | | |
| ≥65 years | 2645/5472 (48.3) | 2615/5470 (47.8) |
| ≥75 years | 1022/5472 (18.7) | 988/5470 (18.1) |
| Sex, No. (%) | | |
| Male | 3914/5472 (71.5) | 3977/5470 (72.7) |
| Female | 1558/5472 (28.5) | 1493/5470 (27.3) |
| Race, No. (%) | | |
| White | 5132/5469 (93.8) | 5120/5463 (93.7) |
| Asian | 171/5469 (3.1) | 175/5463 (3.2) |
| Black | 149/5469 (2.7) | 146/5463 (2.7) |
| Other | 17/5469 (0.3) | 22/5463 (0.4) |
| Hispanic or Latino, No. (%) | 193/5472 (3.5) | 196/5470 (3.6) |
| Height, cm | 172.0 (165, 178) | 172.0 (165, 178) |
| Diabetes Type, No. (%) | | |
| IDDM | 459/5464 (8.4) | 404/5463 (7.4) |
| Non-IDDM | 1020/5464 (18.7) | 1108/5463 (20.3) |
| Unknown Type | 40/5464 (0.7) | 23/5463 (0.4) |
| Family history of CAD, No. (%) | 2088/5120 (40.8) | 2079/5115 (40.6) |

TABLE 14-continued

Additional baseline and procedural characteristics for the modified
intention-to-treat population, according to the treatment group.*

| Characteristic | Cangrelor (N = 5472) | Clopidogrel (N = 5470) |
|---|---|---|
| Catheter Access Site, No. (%) | | |
| Femoral | 4053/5472 (74.1) | 4011/5470 (73.3) |
| Radial | 1410/5472 (25.8) | 1445/5470 (26.4) |
| Brachial | 9/5472 (0.2) | 14/5470 (0.3) |
| Number of vessels treated, index PCI, No. (%) | | |
| 0 | 49/5472 (0.9) | 49/5470 (0.9) |
| 1 | 4545/5472 (83.1) | 4604/5470 (84.2) |
| 2 | 768/5472 (14.0) | 723/5470 (13.2) |
| 3 | 103/5472 (1.9) | 89/5470 (1.6) |
| 4 | 7/5472 (0.1) | 5/5470 (0.1) |

*Denominators exclude patients in whom the status was reported as unknown by the site. There were no significant differences between the two groups, except for type of diabetes (p < 0.05). CAD denotes coronary artery disease; IDDM denotes insulin-dependent diabetes mellitus; and MITT denotes modified intent to treat.

The results of the analyses of the efficacy and safety end points at 48 hours after randomization are provided in Tables 15, 16, and 17.

Figure 9A:
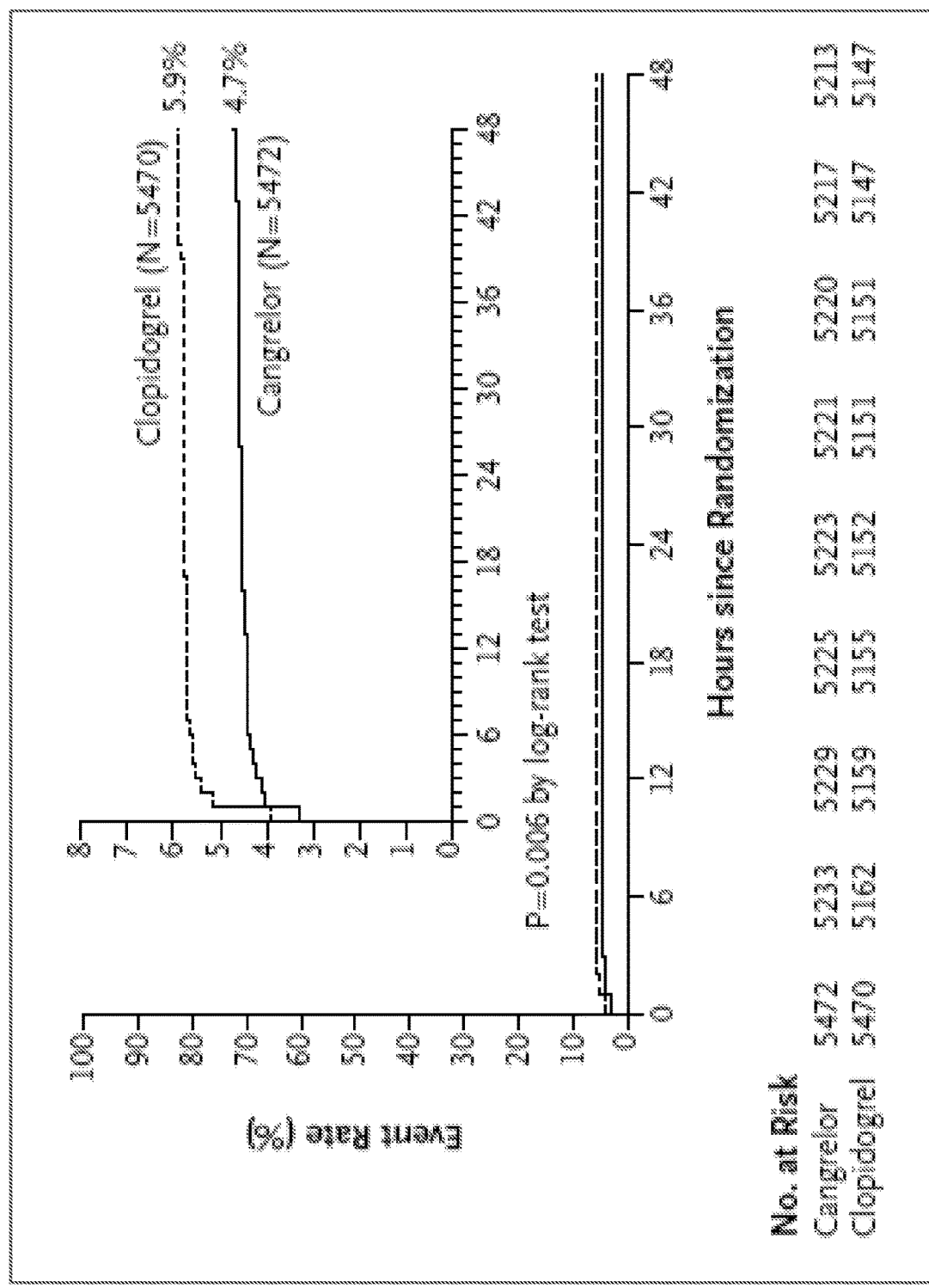
FIGS. 9A and 9B—landmark analysis of Kaplan Meier curves for the primary endpoint (FIG. 9A) and the key secondary end point of stent thrombosis (FIG. 9B) in the study described in Example 3.

The rate of the primary composite efficacy end point of death from any cause, myocardial infarction, IDR, or stent thrombosis at 48 hours was significantly lower in the cangrelor group than in the clopidogrel group (4.7% vs. 5.9%; odds ratio, 0.78; 95% confidence interval [CI], 0.66 to 0.93; P=0.005), on the basis of the prespecified logistic-regression analysis, which adjusted for baseline status (normal vs. abnormal) and clopidogrel loading dose (600 mg vs. 300 mg) (Table 15). The result of the crude analysis was similar (odds ratio, 0.79; 95% CI, 0.67 to 0.93; P=0.006). FIG. 9A shows the Kaplan-Meier estimates of the time-to-event distributions for the primary end point. The number needed to treat with cangrelor to prevent one primary end-point event is 84 (95% CI, 49 to 285).

Figure 9B:
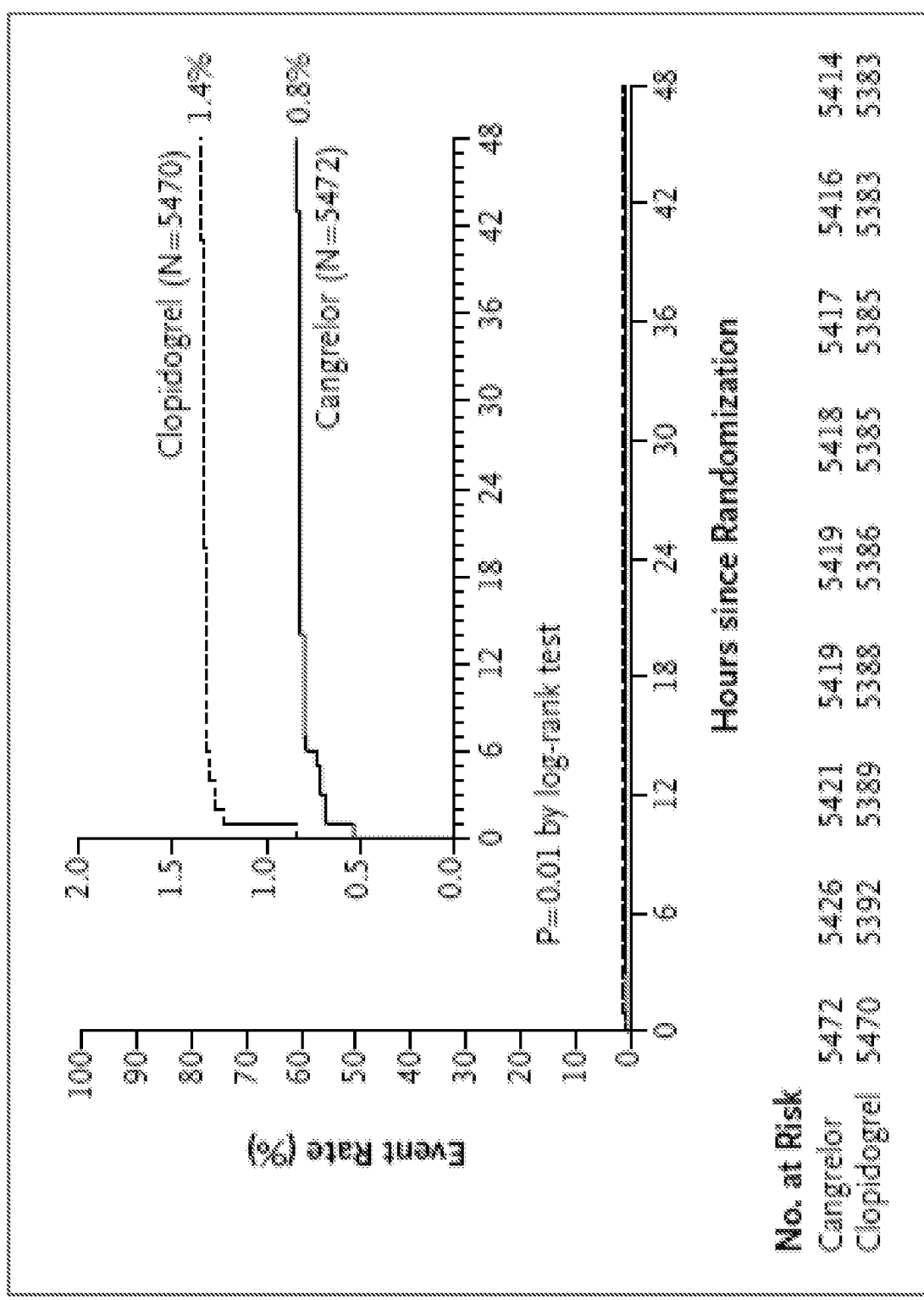

The rate of the key secondary efficacy end point of stent thrombosis at 48 hours was also lower in the cangrelor group than in the clopidogrel group (0.8% vs. 1.4%; odds ratio, 0.62; 95% CI, 0.43 to 0.90; P=0.01) (Table 15). FIG. 9B shows the Kaplan-Meier estimates of the time-to-event distributions for the key secondary end point.

The rate of the primary safety end point, GUSTO-defined severe bleeding, was 0.16% in the cangrelor group as compared with 0.11% in the clopidogrel group (odds ratio, 1.50; 95% CI, 0.53 to 4.22; P=0.44) (Table 15). Bleeding events according to several other bleeding definitions were also examined (Table 17). In a post hoc analysis, the primary efficacy end point and the primary safety end point were combined to provide a composite end point of the net rate of adverse clinical events, which was 4.8% in the cangrelor group as compared with 6.0% in the clopidogrel group (odds ratio, 0.80; 95% CI, 0.68 to 0.94; P=0.008) (Table 15).

TABLE 15

Efficacy and safety end points at 48 hours after randomization.*

| End Point | Cangrelor | Clopidogrel | Odds Ratio (95% CI) | P Value |
|---|---|---|---|---|
| | number/total number (percent) | | | |
| Efficacy | | | | |
| No. of Patients in modified intention-to-treat population | 5472 | 5470 | | |
| Primary end point: death from any cause, myocardial infarction, ischemia-driven revascularization, or stent thrombosis† | 257/5470 (4.7) | 322/5469 (5.9) | 0.78 (0.66-0.93) | 0.005 |
| Key secondary end point: stent thrombosis | 46/5470 (0.8) | 74/5469 (1.4) | 0.62 (0.43-0.90) | 0.01 |
| Myocardial infarction | 207/5470 (3.8) | 255/5469 (4.7) | 0.80 (0.67-0.97) | 0.02 |
| Q-wave myocardial infarction | 11/5470 (0.2) | 18/5469 (0.3) | 0.61 (0.29-1.29) | 0.19 |
| Ischemia-driven revascularization | 28/5470 (0.5) | 38/5469 (0.7) | 0.74 (0.45-1.20) | 0.22 |
| Death from any cause | 18/5470 (0.3) | 18/5469 (0.3) | 1.00 (0.52-1.92) | >0.999 |
| Death from cardiovascular causes | 18/5470 (0.3) | 18/5469 (0.3) | 1.00 (0.52-1.92) | >0.999 |
| Death or stent thrombosis | 59/5470 (1.1) | 87/5469 (1.6) | 0.67 (0.48-0.94) | 0.02 |
| Death, Q-wave myocardial infarction, or ischemia-driven revascularization | 49/5470 (0.9) | 64/5469 (1.2) | 0.76 (0.53-1.11) | 0.16 |
| Safety: non-CABG-related bleeding | | | | |
| No. of patients in safety population | 5529 | 5527 | | |
| GUSTO-defined bleeding | | | | |
| Primary safety end point: severe or life-threatening bleeding | 9/5529 (0.2) | 6/5527 (0.1) | 1.50 (0.53-4.22) | 0.44 |
| Moderate bleeding | 22/5529 (0.4) | 13/5527 (0.2) | 1.69 (0.85-3.37) | 0.13 |
| Severe or moderate bleeding | 31/5529 (0.6) | 19/5527 (0.3) | 1.63 (0.92-2.90) | 0.09 |

TABLE 15-continued

Efficacy and safety end points at 48 hours after randomization.*

| End Point | Cangrelor | Clopidogrel | Odds Ratio (95% CI) | P Value |
|---|---|---|---|---|
| | number/total number (percent) | | | |
| TIMI-defined bleeding | | | | |
| Major bleeding | 5/5529 (0.1) | 5/5527 (0.1) | 1.00 (0.29)-3.45) | >0.999 |
| Minor bleeding | 9/5529 (0.2) | 3/5527 (0.1) | 3.00 (0.81-11.10) | 0.08 |
| Major or minor bleeding | 14/5529 (0.3) | 8/5527 (0.3) | 1.75 (0.73-4.18) | 0.20 |
| Any blood transfusion | 25/5529 (0.5) | 16/5527 (0.3) | 1.56 (0.83-2.93) | 0.16 |
| Efficacy and safety: net adverse clinical events‡ | | | | |
| Death, myocardial infarction, ischemia-driven revascularization, stent thrombosis, or GUSTO-defined severe bleeding | 264/5470 (4.8) | 327/5469 (6.0) | 0.80 (0.68-0.94) | 0.008 |

*GUSTO denotes Global Use of Strategies to Open Occluded Coronary Arteries, and TIMI denotes Thrombolysis in Myocardial Infarction.
†The prespecified logistic-regression analysis was adjusted for baseline status (normal vs. abnormal) and clopidogrel loading dose (600 mg vs. 300 mg).
‡The primary efficacy and primary safety end points were combined to provide a composite end point of net adverse clinical events in the modified intention-to-treat population.

TABLE 16

Additional efficacy endpoints at 48 hours after randomization for the modified intention-to-treat population.*

| End Point | Cangrelor (N = 5472) | Clopidogrel (N = 5470) | OR (95% CI) | P Value |
|---|---|---|---|---|
| Death/MI | 220/5470 (4.0) | 272/5469 (5.0) | 0.80 (0.67, 0.96) | 0.02 |
| Death/MI/ST | 249/5470 (4.6) | 312/5469 (5.7) | 0.79 (0.66, 0.94) | 0.006 |
| Death/MI/IDR | 230/5470 (4.2) | 286/5469 (5.2) | 0.80 (0.67, 0.95) | 0.01 |
| Death/MI/IDR/Definite ST | 230/5470 (4.2) | 286/5469 (5.2) | 0.80 (0.67, 0.95) | 0.01 |
| Death/MI/Definite ST | 222/5470 (4.1) | 276/5469 (5.0) | 0.80 (0.66, 0.95) | 0.01 |
| Definite ST | 12/5470 (0.2) | 22/5469 (0.4) | 0.54 (0.27, 1.10) | 0.09 |

*MI denotes myocardial infarction, ST denotes stent thrombosis, and IDR denotes ischemia-driven revascularization.

TABLE 17

Additional efficacy and safety endpoints at 48 hours after randomization.*

| | Intention-to-Treat (ITT) | | | |
|---|---|---|---|---|
| Ischemic | Cangrelor (N = 5581) | Clopidogrel (N = 5564) | OR (95% CI) | P Value |
| Death/MI/IDR/ST | 260/5573 (4.7) | 325/5561 (5.8) | 0.79 (0.67, 0.93) | 0.005 |
| Stent thrombosis | 46/5573 (0.8) | 74/5561 (1.3) | 0.62 (0.43, 0.89) | 0.01 |
| MI | 207/5573 (3.7) | 255/5561 (4.6) | 0.80 (0.67, 0.97) | 0.02 |
| Q-wave MI | 11/5573 (0.2) | 18/5561 (0.3) | 0.61 (0.29, 1.29) | 0.19 |
| IDR | 29/5573 (0.5) | 38/5561 (0.7) | 0.76 (0.47, 1.23) | 0.27 |
| Death | 20/5573 (0.4) | 21/5561 (0.4) | 0.95 (0.51, 1.75) | 0.87 |
| CV Death | 20/5573 (0.4) | 21/5561 (0.4) | 0.95 (0.51, 1.75) | 0.87 |
| Death/ST | 61/5573 (1.1) | 90/5561 (1.6) | 0.67 (0.49, 0.93) | 0.02 |
| Death/MI | 222/5573 (4.0) | 275/5561 (5.0) | 0.80 (0.67, 0.96) | 0.01 |
| Death/MI/ST | 251/5573 (4.5) | 315/5561 (5.7) | 0.79 (0.66, 0.93) | 0.005 |
| Death/MI/IDR | 233/5573 (4.2) | 289/5561 (5.2) | 0.80 (0.67, 0.95) | 0.01 |
| Death/Q-wave MI/IDR | 52/5573 (0.9) | 67/5561 (1.2) | 0.77 (0.54, 1.11) | 0.16 |
| Death/MI/IDR/ST/GUSTO Severe Bleeding (Net Adverse Clinical Events, NACE) | 267/5573 (4.8) | 330/5561 (5.9) | 0.80 (0.68, 0.94) | 0.007 |
| | Safety | | | |
| Non-CABG Related Bleeding | Cangrelor (N = 5529) | Clopidogrel (N = 5527) | OR (95% CI) | P Value |
| ACUITY criteria | | | | |
| Major bleeding | 235/5529 (4.3) | 139/5527 (2.5) | 1.72 (1.39, 2.13) | 0.001 |
| Major without ≥5 cm hematoma | 42/5529 (0.8) | 26/5527 (0.5) | 1.62 (0.99, 2.64) | 0.05 |
| Minor bleeding | 653/5529 (11.8) | 475/5527 (8.6) | 1.42 (1.26, 1.61) | <0.001 |

TABLE 17-continued

Additional efficacy and safety endpoints at 48 hours after randomization.*

BARC criteria*

| | | | | |
|---|---|---|---|---|
| Type 3 | 22/5529 (0.4) | 13/5527 (0.2) | 1.69 (0.85, 3.37) | 0.13 |
| Type 3a | 11/5529 (0.2) | 4/5527 (0.1) | 2.75 (0.88, 8.65) | 0.07 |
| Type 3b | 9/5529 (0.2) | 8/5527 (0.1) | 1.12 (0.43, 2.92) | 0.81 |
| Type 3c | 2/5529 (0.0) | 1/5527 (0.0) | 2.00 (0.18, 22.06) | 0.56 |

*MI denotes myocardial infarction, ST denotes stent thrombosis, and IDR denotes ischemia-driven revascularization, CV denotes cardiovascular, GUSTO denotes Global Use of Strategies to Open Occluded Coronary Arteries, ACUITY denotes Acute Catheterization and Urgent Intervention Triage Strategy trial, and BARC denotes Bleeding Academic Research Consortium.

The rate of intraprocedural stent thrombosis was lower in the cangrelor group than in the clopidogrel group (0.6% vs. 1.0%; odds ratio, 0.65; 95% CI, 0.42 to 0.99; P=0.04). The use of rescue therapy with a glycoprotein IIb/IIIa inhibitor was 2.3% with cangrelor as compared with 3.5% with clopidogrel (odds ratio, 0.65; 95% CI, 0.52 to 0.82; P<0.001). The rate of procedural complications was lower with cangrelor than with clopidogrel (3.4% vs. 4.5%; odds ratio, 0.74; 95% CI, 0.61 to 0.90; P=0.002).

At 30 days, the rate of the composite efficacy end point remained significantly lower in the cangrelor group than in the clopidogrel group (6.0% vs. 7.0%; odds ratio, 0.85; 95% CI, 0.73 to 0.99; P=0.03); the relative reduction in stent thrombosis also persisted (1.3% vs. 1.9%; odds ratio, 0.68; 95% CI, 0.50 to 0.92; P=0.01) (Table 18).

TABLE 18

Efficacy outcomes at 30 days after randomization

| End Points | Cangrelor | Clopidogrel | Odds Ratio (95% CI) | P Value |
|---|---|---|---|---|
| | number/total number (percent) | | | |
| No. of Patients in modified intention-to-treat population | 5472 | 5470 | | |
| Death from any cause, myocardial infarction, ischemia-driven revascularization, or stent thrombosis† | 326/5462 (6.0) | 380/5457 (7.0) | 0.85 (0.73-0.99) | 0.03 |
| Stent thrombosis | 71/5462 (1.3) | 104/5457 (1.9) | 0.68 (0.50-0.92) | 0.01 |
| Myocardial infarction | 225/5462 (4.1) | 272/5457 (5.0) | 0.82 (0.68-0.98) | 0.03 |
| Q-wave myocardial infarction | 14/5462 (0.3) | 22/5457 (0.4) | 0.63 (0.32-1.24) | 0.18 |
| Ischemia-driven revascularization | 56/5462 (1.0) | 66/5457 (1.2) | 0.85 (0.59-1.21) | 0.36 |
| Death from any cause | 60/5462 (1.1) | 55/5457 (1.0) | 1.09 (0.76-1.58) | 0.64 |
| Death from cardiovascular causes | 48/5462 (0.9) | 46/5457 (0.8) | 1.04 (0.69-1.57) | 0.84 |

†The prespecified logistic-regression analysis was adjusted for baseline biomarker status (normal vs. abnormal) and clopidogrel loading dose (600-mg vs. 300-mg).

The rate of adverse events related to treatment was similar in the cangrelor and clopidogrel groups (20.2% and 19.1%, respectively; P=0.13); 0.5% of these adverse events in the cangrelor group and 0.4% of those in the clopidogrel group led to discontinuation of the study drug (P=0.21). There were significantly more cases of transient dyspnea with cangrelor than with clopidogrel (1.2% vs. 0.3%, P<0.001) (Table 19).

TABLE 19

Statistically significant treatment emergent adverse events at 48 hours after randomization (safety population).

| System Organ Class Preferred Term | Cangrelor (N = 5529) | Clopidogrel (N = 5527) | Chi-square P value | Fisher exact P value |
|---|---|---|---|---|
| Psychiatric disorders | | | | |
| Agitation | 11/5529 (0.2) | 3/5527 (0.1) | 0.03 | 0.06 |
| Gastrointestinal disorders | | | | |
| Diarrhea | 15/5529 (0.3) | 6/5527 (0.1) | 0.05 | 0.08 |
| General disorders and administration site conditions | | | | |
| Chest Pain | 55/5529 (1.0) | 93/5527 (1.7) | 0.002 | 0.002 |
| Respiratory, thoracic, | | | | |

TABLE 19-continued

Statistically significant treatment emergent adverse events at 48 hours after randomization (safety population).

| System Organ Class Preferred Term | Cangrelor (N = 5529) | Clopidogrel (N = 5527) | Chi-square P value | Fisher exact P value |
|---|---|---|---|---|
| and mediastinal disorders | | | | |
| Dyspnea | 64/5529 (1.2) | 18/5527 (0.3) | <0.001 | <0.001 |
| Injury, poisoning, and procedural complications | | | | |
| Procedural Pain | 4/5529 (0.1) | 12/5527 (0.2) | 0.05 | 0.05 |

P values not adjusted for multiple comparisons.

Figure 10:
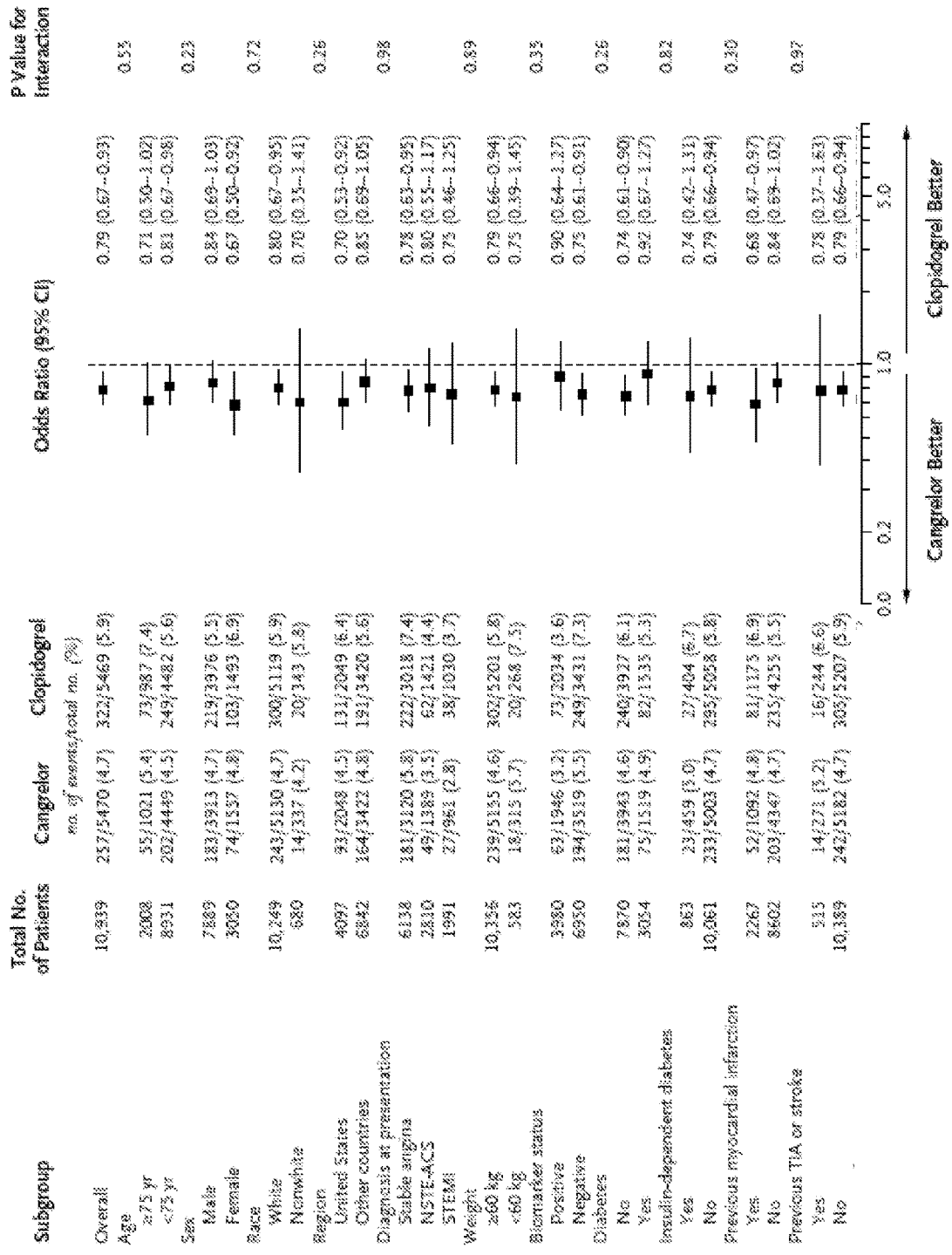
FIG. 10—diagram showing the subgroup analysis of the primary efficacy end point in the study described in Example 3.
Figure 10:
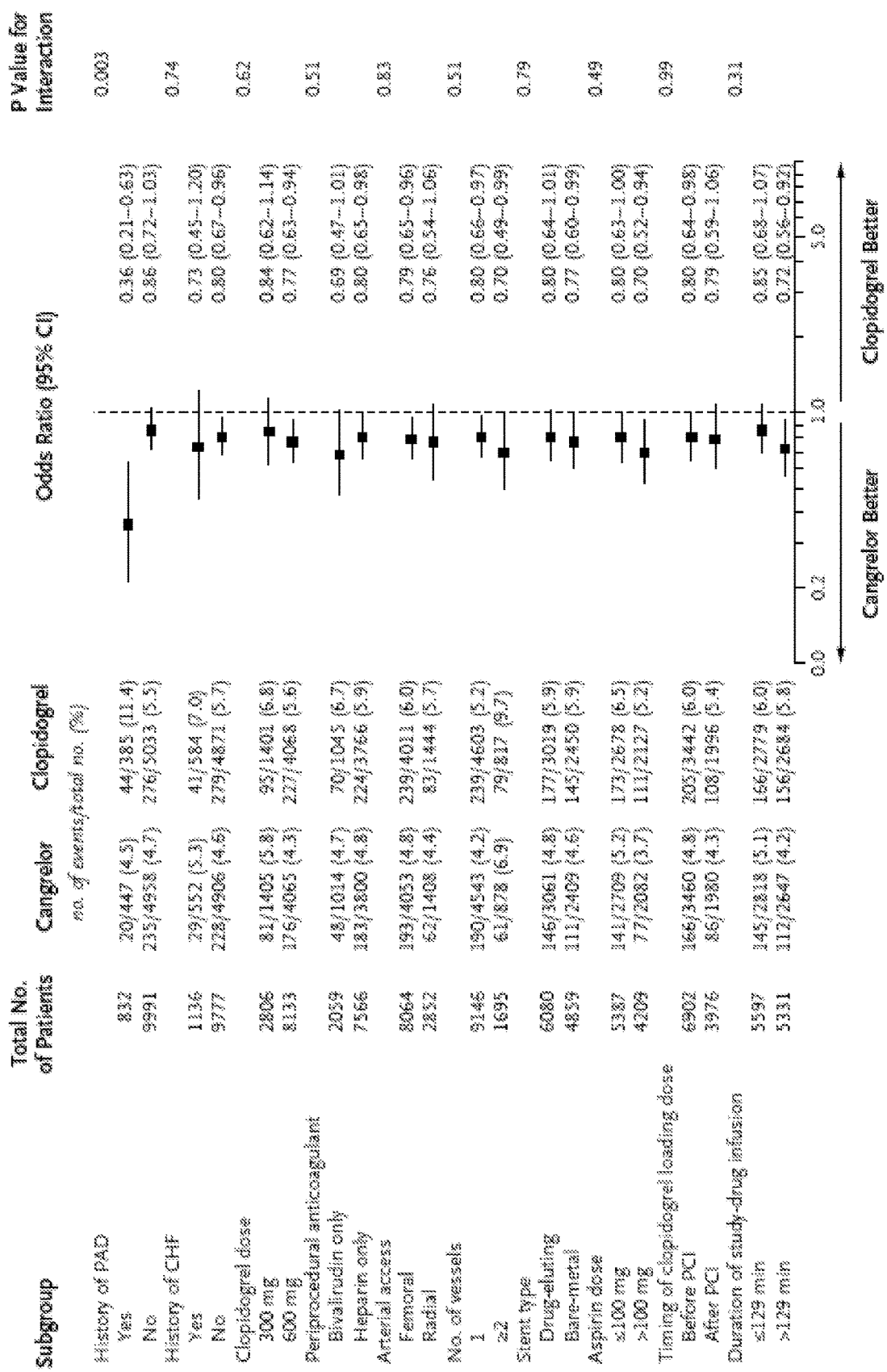

The reduction in the primary efficacy end point with cangrelor was consistent across multiple subgroups, with no significant interactions with baseline variables except for status with respect to a history of peripheral-artery disease. The benefit with cangrelor was similar among patients presenting with STEMI, those presenting with non-ST-segment elevation acute coronary syndrome, and those presenting with stable angina. There was no heterogeneity of treatment effect between patients in the United States and those in other countries (P=0.26) (FIG. 10).

According to the protocol, patients received a loading dose of clopidogrel or placebo after their coronary anatomy was delineated. The majority of patients received the loading dose before PCI was started (63.4%). The rest of the patients received the loading dose in the catheterization laboratory before PCI was completed (6.4%), within 1 hour after PCI was completed (30.1%), or more than 1 hour after PCI was completed (0.1%). There was no significant difference in the effect of cangrelor on the primary end point between patients who received the loading dose immediately before PCI (odds ratio, 0.80; 95% CI, 0.64 to 0.98) and those who received it during or after PCI (odds ratio, 0.79; 95% CI, 0.59 to 1.06) (P=0.99 for interaction). Similarly, there was no significant difference in the effect of cangrelor on the primary end point between patients who received a 600-mg loading dose of clopidogrel (74.4% of the population) and those who received a 300-mg loading dose (25.6% of the population): the odds ratio for the primary end point with cangrelor was 0.77 (95% CI, 0.63 to 0.94) with the 600-mg loading dose and 0.84 (95% CI, 0.62 to 1.14) with the 300-mg loading dose (P=0.62 for interaction). The protocol required at least 2 hours of study-drug infusion; the median duration of infusion in the cangrelor group was 129 minutes (interquartile range, 120 to 146); the duration of infusion was similar in the clopidogrel group (in which patients received a placebo infusion). A subgroup analysis showed a similar effect of cangrelor among patients who received the infusion for 129 minutes or less (odds ratio, 0.85; 95% CI, 0.68 to 1.07) and those who received the infusion for more than 129 minutes (odds ratio, 0.72; 95% CI, 0.56 to 0.92) (P=0.31 for interaction) (FIG. 10).

Figure 11:
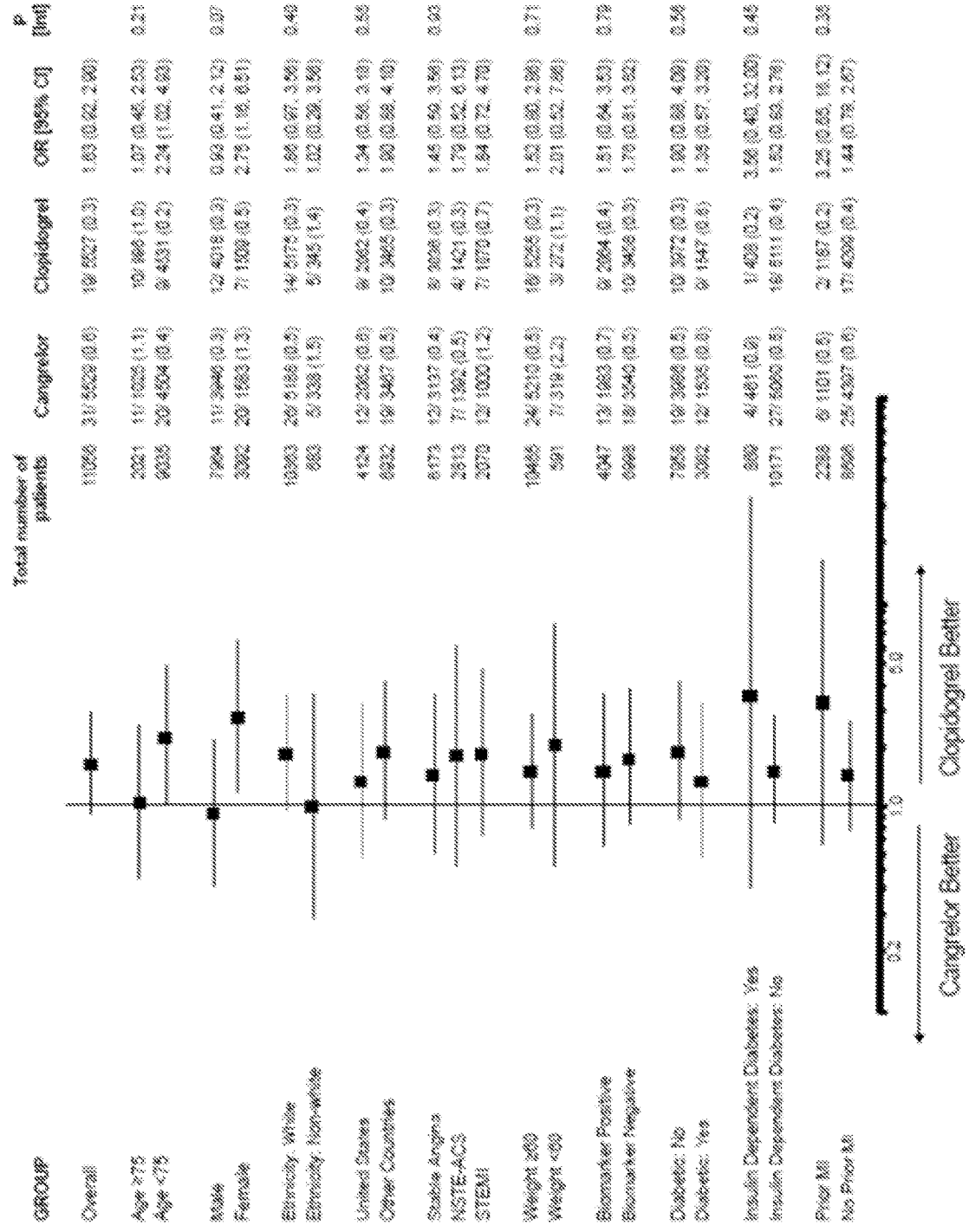
FIG. 11—diagram showing the subgroup analysis of Global Use of Strategies to Open Occluded Coronary Arteries (GUSTO) severe or moderate bleeding in the study described in Example 3.
Figure 11:
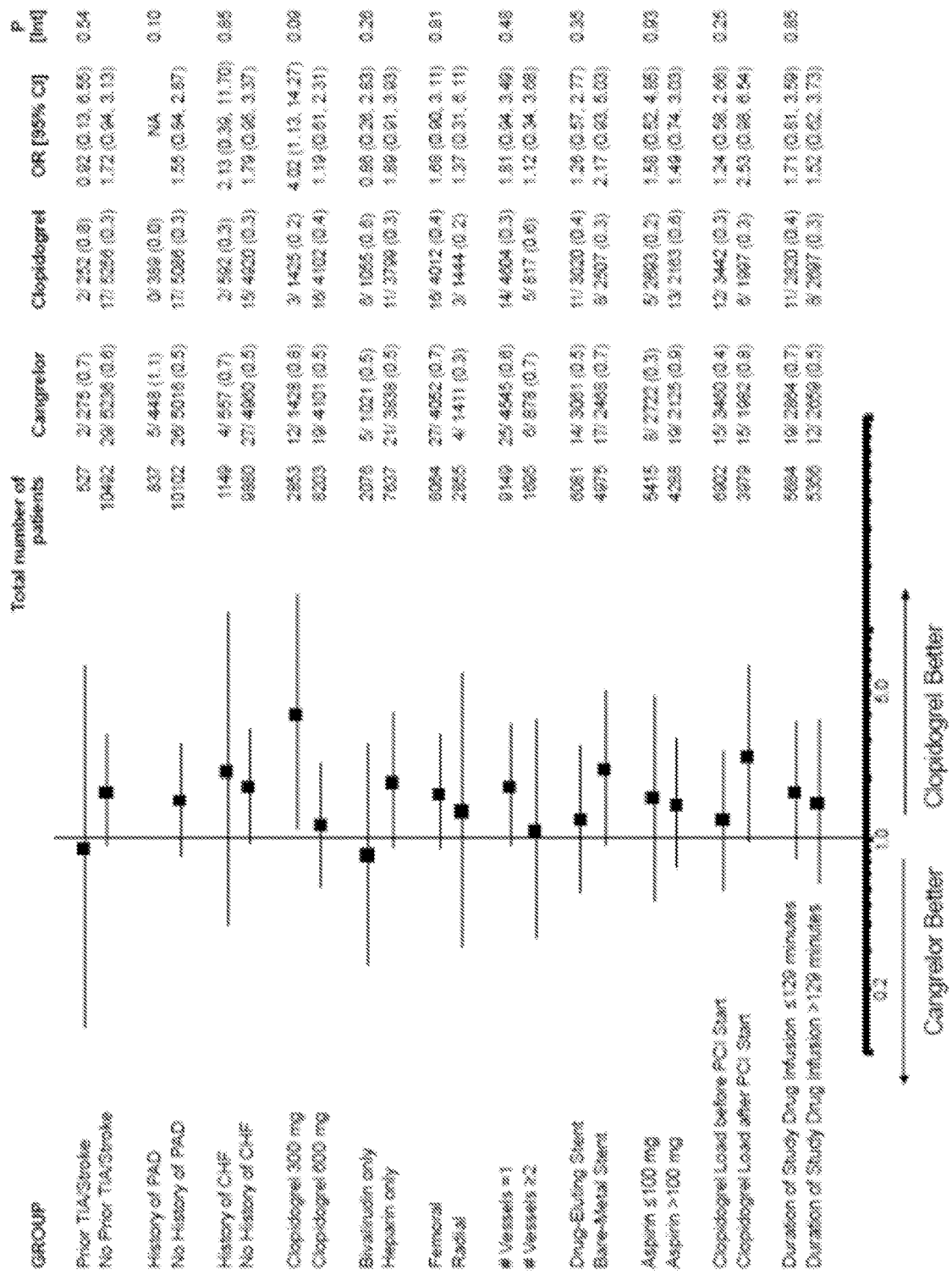

Since the rate of the primary safety end point, GUSTO-defined severe bleeding, was very low, severe bleeding according to GUSTO criteria was combined with moderate bleeding to provide a larger number of events for an analysis of potential subgroup interactions. There were no interactions at P<0.05 (FIG. 11).

As compared with clopidogrel administered immediately before or after PCI, intravenous ADP-receptor blockade with cangrelor significantly reduced the rate of periprocedural complications of PCI, including stent thrombosis. A reduction in the rate of acute periprocedural myocardial infarction accounted for most of the benefit. The odds of an ischemic event were 22% lower with cangrelor than with clopidogrel, and this benefit was not accompanied by a significant increase in severe bleeding or in the need for transfusions. In addition, the odds of stent thrombosis were 38% lower with cangrelor than with clopidogrel. The use of cangrelor resulted in a reduction in ischemic complications across the full spectrum of patients undergoing contemporary PCI, with a consistent benefit in major subgroups.

Example 1 and Example 2 suggested a clinical benefit of cangrelor, including a significant reduction in the secondary end point of stent thrombosis. However, the rate of the primary end point was not reduced in the previous examples, probably because the definition of periprocedural myocardial infarction in those studies did not allow discrimination of reinfarction in patients presenting for PCI soon after admission with a biomarker-positive acute coronary syndrome. In the trial described in Example 3, the definition of periprocedural myocardial infarction required careful assessment of patients' baseline biomarker status. In addition, the use of an angiographic core laboratory allowed objective determination of intraprocedural complications. Table 20 lists the differences between the trials described in Example 1/Example 2 and the trial described in Example 3.

TABLE 20

Differences between the study of Example 3 and the studies of Examples 1 and 2.*†

| | Examples 1 and 2 | Example 3 |
|---|---|---|
| Patient population | 70% Troponin (Tn) elevated at baseline<br>Clopidogrel maintenance (PCI only)<br>PCI required with following:<br>STEMI: safety only (PCI)<br>NSTEMI: Tn elevated<br>Unstable angina: ECG changes and | Assumed 35% Tn elevated at baseline<br>$P2Y_{12}$ inhibitor naive<br>PCI required (Stable angina, NSTE-ACS, STEMI) |

TABLE 20-continued

Differences between the study of Example 3 and the studies of Examples 1 and 2.*†

| | Examples 1 and 2 | Example 3 |
|---|---|---|
| Comparator | pain and age/diabetes<br>Stable angina: capped (15%)<br>600 mg clopidogrel | 300 mg or 600 mg (per hospital standard of care) |
| End point | Primary: Death/MI/IDR at 48 hr | Primary: Death/MI/IDR/ST at 48 hr<br>Key Secondary: ST at 48 hr |
| Myocardial infarction definition | Not UDMI: reliance on cardiac markers alone to define PCI MI<br>1 baseline sample<br>Biomarker normal at baseline: MI defined as CKMB ≥3x ULN post PCI<br>Biomarker elevated at baseline: elevation in CKMB ≥3x ULN and 50% increase from baseline sample or ECG changes | UDMI implemented: reliance on cardiac markers and other evidence of ischemia to define PCI MI<br>2 baseline samples at least 6 hours apart required in NSTE-ACS patients to confirm resolving MI at baseline<br>Baseline normal patients: MI defined as CKMB ≥3x ULN post PCI<br>Baseline abnormal patients were classified into MI increasing or decreasing at baseline:<br>Increasing: re-elevation in CKMB post PCI (≥3xULN and 50% increase from baseline) + additional evidence of ischemia (2 of 2): ECG changes AND angiographic evidence<br>Decreasing: re-elevation in CKMB post PCI (≥3xULN and 50% increase from baseline) + additional evidence of ischemia (1 of 3): ischemic symptoms, ECG changes or angiographic evidence |
| Stent thrombosis definition | Non-standard definition in IDR patients but confirmed by CEC using angiographic source data | ARC definition in patients<br>IPST (Intra-procedural stent thrombosis) = any procedural new or worsened thrombus related to the stent based on angiographic evidence |
| Statistics | Event rate placebo: 7.7%;<br>Effect size: 22.5-25% | Assumed Event rate placebo: 5.1%;<br>Assumed Effect size: 24.5% |

*PCI denotes percutaneous coronary intervention, STEMI denotes ST-segment elevation myocardial infarction, NSTEMI denotes non-ST-elevated myocardial infarction, ECG denotes denotes electrocardiography, NSTE-ACS denotes non-ST-segment elevation acute coronary syndrome, MI denotes myocardial infarction, IDR denotes ischemia-driven revascularization, ST denotes stent thrombosis, UDMI denotes universal definition of myocardial infarction, CKMB denotes creatine kinase-myocardial band isoenzyme, and ULN denotes upper limit of normal.
†Bhatt D L, et al. N Engl J Med 2009; 361 2330-41.
Harrington R A, et al. N Engl J Med 2009; 361 2318-29
White H D, Am Heart J 2012; 163: 182-190.e4
Thygesen, J Am Coll Cardiol 2007; 50: 2173-95.

Example 4—Comparison of the Combination of Cangrelor and Bivalirudin and the Combinations of Clopidogrel and Bivalirudin, Cangrelor and Heparin, and Clopidogrel and Heparin A comparison of the effects of combining cangrelor and clopidogrel with bivalirudin or heparin was performed on a subset of patients from the study described in Example 3. The patients involved in the comparison received a combination of cangrelor and bivalirudin (n=1,020), clopidogrel and bivalirudin (n=1,055), cangrelor and heparin (n=4,509), or clopidogrel and heparin (n=4,471).

The following endpoints were assessed:
Composite endpoint of death, myocardial infarction, ischemia-driven revascularization, and stent thrombosis;
Stent thrombosis;
Large myocardial infarction (5× the upper limit of normal creatine kinase-myocardial band isoenzyme (CKMB));
GPIIb/IIIa use;
Major bleeding (defined by the ACUITY bleeding scale); and
Tranfusions Administration of a combination of cangrelor and bivalirudin, as compared to a combination of clopidogrel and bivalirudin, resulted in lower incidence and reduced relative risk for the composite ischemic endpoint of death, myocardial infarction, ischemia-driven revascularization, and stent thrombosis; stent thrombosis; and large myocardial infarctions (see Table 21). Further, the combination of cangrelor and bivalirudin also resulted in a lower incidence (1.4% vs. 3.1%) and reduced relative risk (55%) for the use of glycoprotein IIb/IIIa as compared to the combination of clopidogrel and bivalirudin.

TABLE 21

Comparison of the Combination of Cangrelor and Bivalirudin, and the Combination of Clopidogrel and Bivalirudin

| Event | Incidence of Cangrelor + Bivalirudin | Incidence of Clopidogrel + Bivalirudin | Relative Risk | Relative Risk Reduction | p-value |
|---|---|---|---|---|---|
| Death, MI, IDR, ST | 4.7% | 6.7% | 0.68 (0.47, 0.99) | 31% | 0.055 |
| ST | 0.7% | 1.4% | 0.48 (0.20, 1.17) | 52% | 0.100 |

TABLE 21-continued

Comparison of the Combination of Cangrelor and Bivalirudin, and the Combination of Clopidogrel and Bivalirudin

| Event | Incidence of Cangrelor + Bivalirudin | Incidence of Clopidogrel + Bivalirudin | Relative Risk | Relative Risk Reduction | p-value |
|---|---|---|---|---|---|
| Large MI (CKMB 5x) | 0.9% | 2.4% | 0.37 (0.17, 0.79) | 63% | 0.007 |

MI denotes myocardial infarction. IDR denotes ischemia-driven revascularization. ST denotes stent thrombosis.

Patients administered with the combination of cangrelor and bivalirudin, as compared to the combination of cangrelor and other anticoagulants (i.e., heparin, etc.), experienced a lower incidence and reduced relative risk for major bleeding based on the ACUITY bleeding scale and transfusions (see Table 22), as well as a lower incidence of moderate or severe bleeding based on the GUSTO scale.

TABLE 22

Comparison of the Combination of Cangrelor and Bivalirudin, and the Combination of Cangrelor and Other Anticoagulants

| Event | Incidence of Cangrelor + Bivalirudin | Incidence of Cangrelor + Heparin | Relative Risk Reduction | p-value |
|---|---|---|---|---|
| Major bleeding (ACUITY scale) | 2.1% | 4.7% | 58% | <0.001 |
| Transfusions | 0.3% | 0.5% | 40% | 0.405 |

Figure 12:
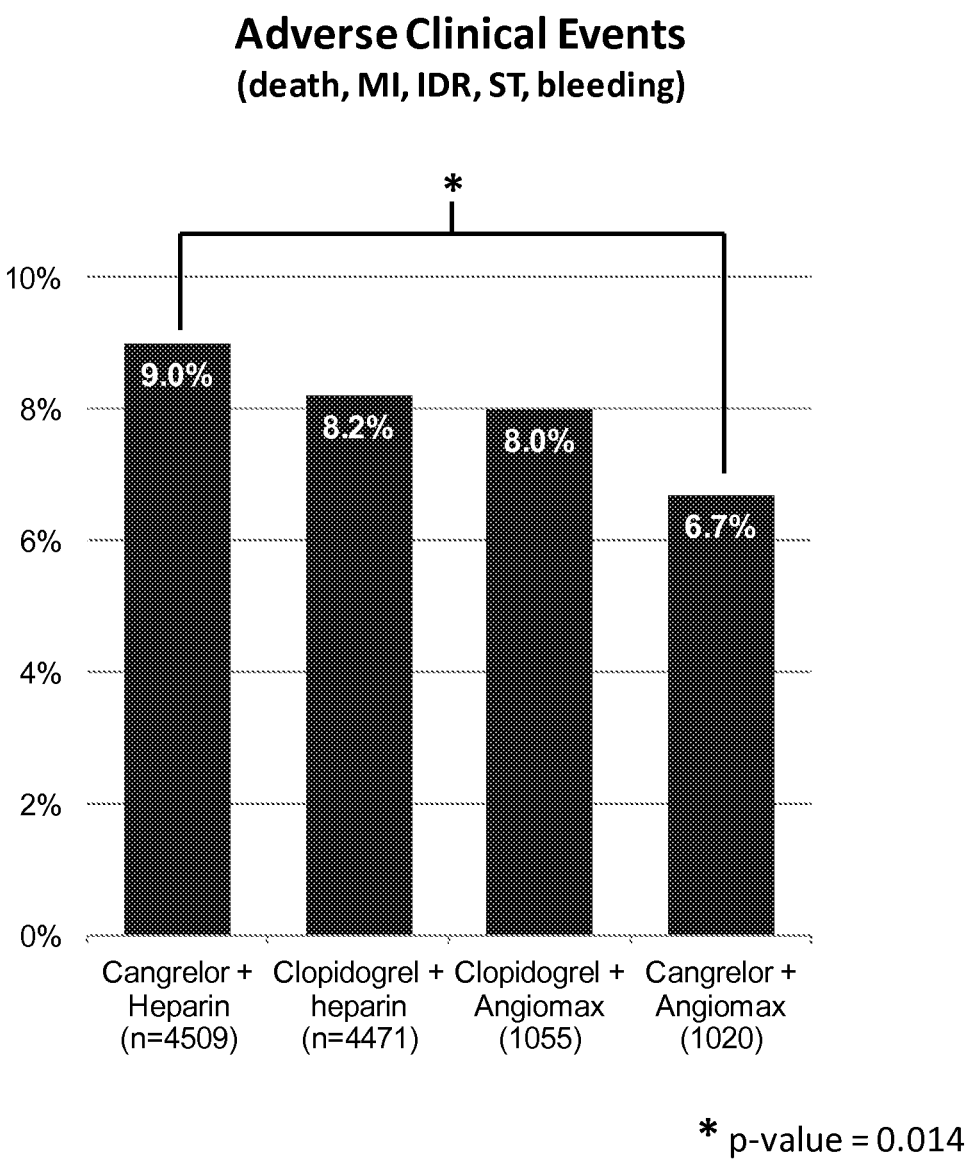
FIG. 12—graph comparing the incidence of adverse clinical events (death, myocardial infarction, ischemia-driven revascularization, stent thrombosis, and bleeding) resulting from administering the combinations of cangrelor and bivalirudin, cangrelor and heparin, clopidogrel and heparin, and clopidogrel and bivalirudin.

In addition, administration of the combination of cangrelor and bivalirudin resulted in a lower incidence of adverse clinical events of death, myocardial infarction, ischemia-driven revascularization, stent thrombosis, and bleeding, as compared to the combinations of cangrelor and heparin, clopidogrel and heparin, and clopidogrel and bivalirudin (see FIG. 12).

These results indicate that administration of the combination of cangrelor and bivalirudin, as compared to the other combinations, resulted in a lower incidence of acute procedural complications, peri-procedural thrombotic events, early stent thrombosis, and major bleeding events in patients undergoing PCI.

Example 5—Compatibility of Cangrelor Injection with Bivalirudin

The physical compatibility of cangrelor injection with bivalirudin during simulated Y-site co-administration was evaluated by visual observation, electronic turbidity measurement, and particulate content assessment.

Cangrelor for injection was supplied in 50 mg lyophilized single-use vials (The Medicines Company, Parsippany, N.J.). Each vial was reconstituted with 5 mL of sterile water for injection to yield a 10 mg/mL solution. The 5 mL contents of each vial was removed using a syringe and needle and transferred to a 50 mL bag of 0.9% sodium chloride injection, USP (B. Braun, Bethlehem, Pa.) yielding a diluted concentration of 1 mg/mL. Bivalirudin was prepared separately in 0.9% sodium chloride injection or 5% dextrose injection (Baxter Healthcare, Deerfield, Ill.) to a final concentration of 5 mg/mL.

5 mL samples of the cangrelor 1 mg/mL diluted solution were separately combined with 5 mL samples of the bivalirudin dilutions in colorless 15-mL borosilicate glass screw-cap culture tubes (Kimble, Division of Owens-Illinois, Toledo, Ohio) with polypropylene caps (Kimble, Division of Owens-Illinois) as described in Trissel L. A. et al., *Am J Hosp Pharm* 50:2359-63 (1993). Each of the sample solutions was passed through a 0.22-µm filter (Millex-GV, Millipore Products, Bedford, Mass.) as it was introduced into the tube. Each combination was prepared in duplicate, reversing the order of drug addition between the two samples.

As controls, cangrelor 1 mg/mL in 0.9% sodium chloride injection and the bivalirudin solutions were each diluted with an equal volume of 0.9% sodium chloride injection and separately with 5% dextrose injection to a concentration of 0.5 mg/mL to simulate test sample preparations.

Incompatibility in the cangrelor-bivalirudin combinations was defined as any visible particulate matter, substantial haze or turbidity change from that in the controls, or a color change, microprecipitate formation, or gas evolution. All samples were examined visually with the unaided eye in normal laboratory fluorescent light. Combinations with no obvious visible incompatibility were examined further using a Tyndall beam (high-intensity monodirectional light source, Dolan-Jenner Industries, Woburn, Mass.) as described in Trissel L. A. et al., *Am J Hosp Pharm* 50:2359-63 (1993). Inspections were performed over the first 15 minutes after sample preparation and at intervals of one and four hours after sample preparation. The samples were stored at room temperature (approximately 23° C.).

The samples were also assessed immediately after preparation and at one and four hours after preparation using a color-correcting turbidimeter (Model 2100AN, Hach Company, Loveland, Colo.) as previously described in Trissel L. A. et al., *Am J Hosp Pharm* 49:1716-9 (1992); Trissel L. A. et al., *Am J Hosp Pharm* 50:300-4 (1993). Triplicate determinations were made on each of the samples. The particle content of the samples was quantified after four hours using a light obscuration particle sizer/counter (Model 9703, Hiac-Royco, Division of Pacific Scientific Company, Grants Pass, Oreg.) to determine particle content in the size range of 2.04 to 112 µm (the validated detection limits of the particle sizer/counter) to verify the absence of unacceptable amounts of microparticulates. Triplicate determinations were again made using the light obscuration particle sizer/counter on these samples for particulate determinations. Physical instability was defined as visible particulate matter, haze, color change or a change (increase or decrease) in measured turbidity change of 0.5 nephelometric turbidity unit or more (Trissel L. A. et al., *Am J Hosp Pharm* 50:2359-63 (1993); Trissel L. A. et al., *Am J Hosp Pharm* 49:1716-9 (1992); Trissel L. A. et al., *Am J Hosp Pharm* 50:300-4 (1993)).

Cangrelor 1 mg/mL in 0.9% sodium chloride injection, USP, visually appeared in normal room light and when viewed using a Tyndall beam as a clear, colorless free-flowing liquid. The initial 1 mg/mL dilution was essentially without turbidity having a very low measured turbidity near 0.13 nephelometric turbidity units (NTU). When diluted to 0.5 mg/mL with an equal amount of 0.9% sodium chloride injection, USP, or 5% dextrose injection, USP, in a manner identical to mixing with each of the secondary test drugs, the measured turbidity level remained near 0.13 NTU.

The cangrelor dilution in sodium chloride 0.9% was found to be physically compatible with bivalirudin. The combinations exhibited no observable changes, such as visible precipitation or turbidity formation, microparticulate formation or increased measured haze, and they appeared visually to be very similar in clarity to the cangrelor solution diluted with an equal quantity of a simple aqueous solution as well as exhibiting similar measured turbidities.

Having thus described in detail embodiments of the present invention, it is to be understood that the invention defined by the above paragraphs is not to be limited to particular details set forth in the above description as many apparent variations thereof are possible without departing from the spirit or scope of the present invention.

What is claimed is:

1. A method of treating an ischemic event in a patient who is being prepared for or is undergoing percutaneous coronary intervention (PCI), wherein the ischemic event is selected from the group consisting of stent thrombosis, myocardial infarction and ischemia-driven revascularization, consisting of administering to the patient a pharmaceutical composition consisting essentially of cangrelor and a pharmaceutically acceptable excipient consisting of one or more of mannitol, sorbitol, and sodium hydroxide, wherein the pharmaceutical composition is lyophilized, the lyophilized pharmaceutical composition is dissolved in an intravenous fluid and is administered to the patient intravenously.

2. The method of claim 1, wherein the method treats an ischemic event during PCI.

3. The method of claim 1, wherein the method treats an ischemic event after PCI.

4. The method of claim 1, wherein the ischemic event is stent thrombosis.

5. The method of claim 4, wherein the stent thrombosis is intraprocedural stent thrombosis.

6. The method of claim 1, wherein the pharmaceutical composition is administered to the patient before PCI, during PCI, after PCI, or a combination thereof.

7. The method of claim 1, wherein the pharmaceutical composition is administered as a bolus, as a continuous infusion, or as a bolus followed by a continuous infusion.

8. The method of claim 7, wherein the bolus of the pharmaceutical composition is in a dose of about 20 µg/kg to about 40 µg/kg cangrelor.

9. The method of claim 8, wherein the continuous infusion of the pharmaceutical composition is in a dose of about 1 µg/kg/min to about 10 µg/kg/min cangrelor.

10. The method of claim 7, wherein the continuous infusion is administered for the longer of (a) duration of the PCI, or (b) at least about 2 hours.

11. The method of claim 1, wherein the administration of the pharmaceutical composition to the patient is not accompanied by a significant increase in severe bleeding or the need for transfusions.

12. The method of claim 1, wherein the PCI comprises stent implantation.

13. A method of treating an ischemic event in a patient who is being prepared for or is undergoing percutaneous coronary intervention (PCI), wherein the ischemic event is selected from the group consisting of stent thrombosis, myocardial infarction, and ischemia-driven revascularization, consisting of administering to the patient a pharmaceutical composition consisting essentially of cangrelor and a pharmaceutically acceptable excipient consisting of one or more of mannitol, sorbitol, and sodium hydroxide wherein the pharmaceutical composition is lyophilized, the lyophilized pharmaceutical composition is dissolved in an intravenous fluid and is administered to the patient intravenously, and administering a $P2Y_{12}$ inhibitor selected from the group consisting of clopidogrel, prasugrel, and ticagrelor.

14. The method of claim 13, further comprising administering a $P2Y_{12}$ inhibitor is prasugrel.

* * * * *